(12) United States Patent
Tanaka et al.

(10) Patent No.: US 11,370,761 B2
(45) Date of Patent: Jun. 28, 2022

(54) VOLTAGE-DEPENDENT T-TYPE CALCIUM CHANNEL INHIBITOR

(71) Applicants: Nippon Chemiphar Co., Ltd., Tokyo (JP); Kinki University, Osaka (JP)

(72) Inventors: Hiroto Tanaka, Misato (JP); Isao Ooi, Misato (JP); Kohei Hayashida, Misato (JP); Toru Ogawa, Misato (JP); Atsufumi Kawabata, Osaka (JP)

(73) Assignees: Nippon Chemiphar Co., Ltd., Tokyo (JP); Kinki University, Osaka (JP)

( * ) Notice: Subject to any disclaimer, the term of this patent is extended or adjusted under 35 U.S.C. 154(b) by 332 days.

(21) Appl. No.: 16/479,674

(22) PCT Filed: Jan. 22, 2018

(86) PCT No.: PCT/JP2018/001790
§ 371 (c)(1),
(2) Date: Jul. 22, 2019

(87) PCT Pub. No.: WO2018/135659
PCT Pub. Date: Jul. 26, 2018

(65) Prior Publication Data
US 2021/0323930 A1 Oct. 21, 2021

(30) Foreign Application Priority Data
Jan. 23, 2017 (JP) .............................. JP2017-009755

(51) Int. Cl.
| C07D 235/16 | (2006.01) |
|---|---|
| C07D 401/12 | (2006.01) |
| C07D 403/08 | (2006.01) |
| C07D 403/12 | (2006.01) |
| A61P 29/00 | (2006.01) |
| C07D 401/14 | (2006.01) |

(52) U.S. Cl.
CPC ............ *C07D 235/16* (2013.01); *A61P 29/00* (2018.01); *C07D 401/12* (2013.01); *C07D 401/14* (2013.01); *C07D 403/08* (2013.01); *C07D 403/12* (2013.01)

(58) Field of Classification Search
CPC .. C07D 235/16; C07D 401/12; C07D 403/08; C07D 403/12
See application file for complete search history.

(56) References Cited

FOREIGN PATENT DOCUMENTS

| JP | 2005529114 A | 9/2005 |
|---|---|---|
| JP | 2008535801 A | 9/2008 |
| JP | 2009500340 A | 1/2009 |
| JP | 2010503676 A | 2/2010 |
| JP | 2012528078 A | 11/2012 |
| WO | 2008043183 A1 | 4/2008 |
| WO | 2008057856 A2 | 5/2008 |
| WO | 2008110008 A1 | 9/2008 |
| WO | 2010137351 A1 | 12/2010 |
| WO | 2011032291 A1 | 3/2011 |
| WO | 2011053542 A1 | 5/2011 |
| WO | 2015093534 A1 | 6/2015 |
| WO | 2017122754 A1 | 7/2017 |

OTHER PUBLICATIONS

Chemical Abstracts Registry No. 1355924-86-5, indexed in the Registry file on STN CAS Online on Feb. 8, 2012. (Year: 2012).*
Chemical Abstracts Registry No. 1385279-54-8, indexed in the Registry file on STN CAS Online on Aug. 2, 2012. (Year: 2012).*
Chemical Abstracts Registry No. 1316765-35-1, indexed in the Registry file on STN CAS Online on Aug. 12, 2011. (Year: 2011).*
Jacus MO et al., Presynaptic Cav3.2 channels regulate excitatory neurotransmission in nociceptive dorsal horn neurons. J Neurosci. 2012, 32, 9374-82.

(Continued)

*Primary Examiner* — Laura L Stockton
(74) *Attorney, Agent, or Firm* — Wood Herron & Evans LLP

(57) ABSTRACT

A compound represented by General Formula (I), a tautomer, a stereoisomer, or a pharmaceutically acceptable salt of the compound, or a solvate thereof is used as a voltage-dependent T-type calcium channel inhibitor,

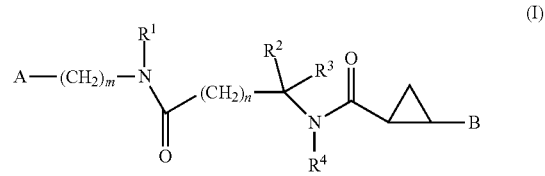

(I)

in the formula,
A represents a benzene ring which may have a substituent or the like;
B represents a hetero-fused ring consisting of a 5- or 6-membered heteroaryl ring having one to three same or different heteroatoms selected from an oxygen atom, a sulfur atom, and a nitrogen atom, and a carbon atom, as a ring-constituting atom, and a benzene ring, or the like, and the hetero-fused ring may have a substituent, and is bonded to a cyclopropyl group via a carbon atom constituting these rings;
$R^1$ represents a hydrogen atom, an alkyl group having 1 to 6 carbon atoms, or the like;
$R^2$ and $R^3$ may be the same as or different from each other, and each represents a hydrogen atom, an alkyl group having 1 to 6 carbon atoms, or the like, or $R^2$ and $R^3$ together form $CH_2CH_2$ or the like;
$R^4$ represents a hydrogen atom, an alkyl group having 1 to 6 carbon atoms, or the like;
m represents 0, 1, or 2; and
n represents 0 or 1.

22 Claims, 1 Drawing Sheet

(56) References Cited

OTHER PUBLICATIONS

Choi S et al., Attenuated pain responses in mice lacking Cav3.2 T-type channels. Genes Brain Behav. 2007, 6, 425-431.

Jagodic MM et al., Upregulation of the T-type calcium current in small rat sensory neurons after chronic constrictive injury of the sciatic nerve. J Neurophysiol. 2008, 99, 3151-6.

Messinger RB et al., In-vivo silencing of the Cav3.2 T-type calcium channels in sensory neurons alleviates hyperalgesia in rats with streptozocin-induced diabetic neuropathy. Pain. 2009, 145, 184-95.

Jagodic MM et al., Cell-specific alterations of T-type calcium current in painful diabetic neuropathy enhance excitability of sensory neurons. J Neurosci. 2007, 27, 3305-16.

Marger F et al., T-type calcium channels contribute to colonic hypersensitivity in a rat model of irritable bowel syndrome. Proc Natl Acad Sci USA. 2011, 5. 11268-73.

STN Registry file, release on Jul. 21, 2016, CA Registry No. 1957171-08-2 etc, [online], [retrieved on Mar. 22, 2018].

PCT Office, International Search Report issued in corresponding PCT/JP2018/001790 dated Apr. 3, 2018, 4 pages.

Pubchem: "N-[1-(Benzylamino)-1-oxopropan-2-yl]-2-(3-methylthiophen-2-yl)cyclopropane-1-carboxamide", 122138108, Sep. 26, 2016 (Sep. 26, 2016), XP055705007, Retrieved from the Internet: URL:https://pubchem.ncbi.nlm.nih.gov/compo und/ 122138108 [retrieved on Jun. 15, 2020].

Pubchem: "1-[2-(Furan-2-yl)cyclopropanecarbonyl]-N-(furan-2-ylmethyl)pyrrolidine-2-carboxamide", 86851726, Feb. 7, 2015 (Feb. 7, 2015), XP055705002, Retrieved from the Internet: URL:https://pubchem.ncbi.nlm.nih.gov/compound/86851726#section= Identification-and-Related-Records [retrieved on Jun. 15, 2020].

Pubchem: "N-[2-Oxo-2-(2,3,4-trifluoroanilino)ethyl]-2-(1H-1,2,4-triazol-5-yl)cyclopropane-1-carboxamide", 121546056, Sep. 7, 2016 (Sep. 7, 2016), XP055706268, Retrieved from the Internet: URL:https://pubchem.ncbi.nlm.nih.gov/compound/121546056 [retrieved on Jun. 18, 2020].

European Patent Office, Search Report issued in EP 18741980.9 dated Jun. 30, 2020.

* cited by examiner

VOLTAGE-DEPENDENT T-TYPE CALCIUM CHANNEL INHIBITOR

TECHNICAL FIELD

The present invention relates to a cyclopropanecarboxamide compound having a diamide structure, and a voltage-dependent T-type calcium channel inhibitor containing the compound as an active ingredient.

BACKGROUND ART

A voltage-dependent T-type calcium channel is expressed in a dorsal root ganglion of a primary afferent nerve fiber or posterior horn of spinal cord (Non-Patent Document 1). Since it has been reported that in a knockout mouse deficient in a T-type calcium channel (Cav3.2 channel), pain-related behaviors in acute pain, inflammatory pain, and visceral pain are decreased (Non-Patent Document 2), the Cav3.2 channel are intimately involved in the transmission of pain. In addition, it has been reported that in a dorsal root ganglion of a pathological model animal with pain such as neuropathic pain (Non-Patent Document 3), painful diabetic neuropathy (Non-Patent Document 4 and 5), and irritable bowel syndrome (Non-Patent Document 6), the current density of the T-type calcium channel is increased and overactivity occurs, and thus the T-type calcium channel may be a target for a new mechanism of a therapeutic agent for pain. Since a T-type calcium channel inhibitor has a different action mechanism from an opioid receptor agonist and a α2δ ligand, T-type calcium channel inhibitors are also expected to be effective against chronic pain that is resistant to existing agents.

Incidentally, as a cyclopropanecarboxamide compound, in Patent Document 1, a compound represented by the following General Formula (A):

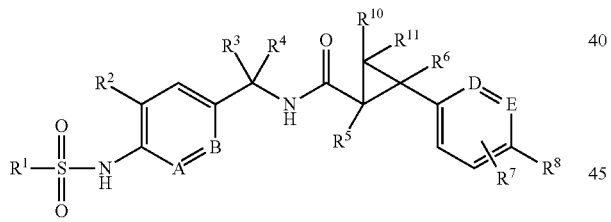

is disclosed, and in Patent Document 2, a compound represented by the following General Formula (B):

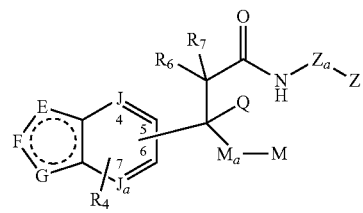

is disclosed.

However, the above-mentioned Patent Document 1 and Patent Document 2 do not describe that these compounds have a voltage-dependent T-type calcium channel inhibitory action.

On the other hand, as a compound having a voltage-dependent T-type calcium channel inhibitory action, in Patent Document 3, a compound represented by the following General Formula (C):

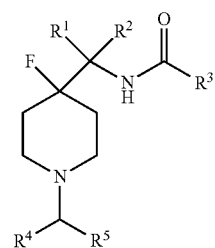

is described.

in Patent Document 4, a compound represented by the following General Formula (D):

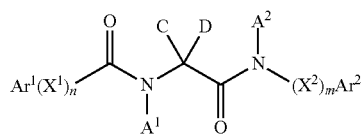

is described.

Moreover, in Patent Document 5, a compound (RQ-00311651) represented by the following Formula (E):

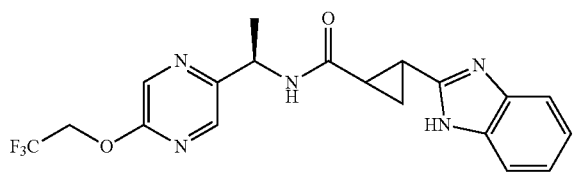 [SMILES: C[C@@H](NC(=O)C1CC1c1nc2ccccc2[nH]1)c1cnc(OCC(F)(F)F)cn1]

is described, in Patent Document 6, a compound represented by the following Formula (F):

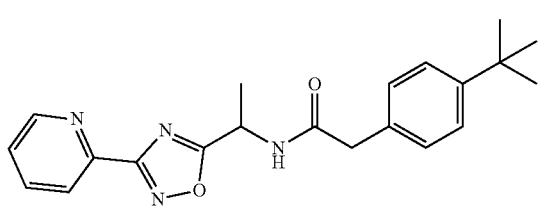 [SMILES: CC(NC(=O)Cc1ccc(C(C)(C)C)cc1)c1nc(-c2ccccn2)no1]

is described, and in Patent Document 7, a compound represented by the following General Formula (G):

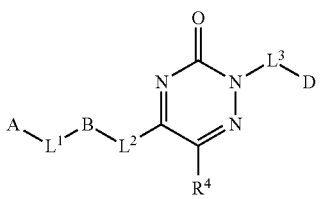

is described.

Incidentally, in the above-mentioned Patent Document 7, as a target disease of the compound having a voltage-dependent T-type calcium channel inhibitory action, pain is mentioned, as a limited target disease, chronic pain is mentioned, and as a further limited target disease, neuropathic pain is mentioned.

The Patent Document states that "the pain is classified into chronic pains and acute pains including neuropathic pain, inflammatory pain, cancer pain, and visceral pain, primary diseases of which are exemplified by diabetic neuropathy, traumatic neurological disorder, nerve compression, strangulation, spinal cord injury, cerebral apoplexy, fibromyalgia syndrome, carpal tunnel syndrome, osteoarthritis, rheumatoid arthritis and multiple sclerosis, herpes zoster, herpes simplex, syphilis, nerve disorders induced by cancer chemotherapy, HIV, and HIV treatment, chronic joint pain, postherpetic neuralgia, neuroma pain, trigeminal neuralgia, phantom limb pain, postoperative pain, stump pain, tooth pain, plexus neuropathy, glossopharyngeal neuralgia, laryngeal neuralgia, migraine, carcinomatous neuropathy, polyneuropathy, causalgia, low back pain, complex regional pain syndrome (CRPS), and thalamic pain", and describes that pain derived from causes other than the causes mentioned above is also included in the target disease of active ingredient described in the Patent Document; and the Patent Document states that "Examples of other diseases except the pain include diseases associated with central nervous system (CNS) disorders, diseases associated with bladder function disorders, cerebral apoplexy, itching, atopic dermatitis, hypertension, hyperaldosteronemia, edema, ischemic heart diseases, age-related macular degeneration, cancer, diabetes mellitus, sterility, sexual dysfunction, arrhythmia, and kidney disease. Examples of the diseases associated with central nervous system (CNS) disorders include epilepsy, essential tremor, schizophrenia, Parkinson's disease, manic-depressive illness, bipolar disorder, depression, anxiety, dementia, drug dependence, Huntington's disease, and sleep disturbance. Examples of the diseases associated with bladder function disorder include overactive bladder".

CITATION LIST

Patent Documents

[Patent Document 1] Published Japanese Translation No. 2008-535801 of the PCT International Publication
[Patent Document 2] PCT International Publication No. WO 2008/57856
[Patent Document 3] Published Japanese Translation No. 2009-500340 of the PCT International Publication
[Patent Document 4] PCT International Publication No. WO 2008/110008
[Patent Document 5] PCT International Publication No. WO 2010/137351
[Patent Document 6] PCT International Publication No. WO 2011/053542
[Patent Document 7] PCT International Publication No. WO 2015/093534

Non-Patent Documents

[Non-Patent Document 1] Jacus M O, Uebele V N, Renger J J, Todorovic S M.; Presynaptic Cav3.2 channels regulate excitatory neurotransmission in nociceptive dorsal horn neurons. J Neurosci. 2012, 32, 9374-82.
[Non-Patent Document 2] Choi S, Na H S, Kim J, Lee J, Lee S, Kim D, Park J, Chen C C, Campbell K P, Shin H S.; Attenuated pain responses in mice lacking CaV3.2 T-type channels. Genes Brain Behav. 2007, 6, 425-331.
[Non-Patent Document 3] Jagodic M M, Pathirathna S, Joksovic P M, Lee W, Nelson M T, Naik A K, Su P, Jevtovic-Todorovic V, Todorovic S M.; Upregulation of the T-type calcium current in small rat sensory neurons after chronic constrictive injury of the sciatic nerve. J Neurophysiol. 2008, 99, 3151-6.
[Non-Patent Document 4] Messinger R B, Naik A K, Jagodic M M, Nelson M T, Lee W Y, Choe W J, Orestes P, Latham J R, Todorovic S M, Jevtovic-Todorovic V.; In vivo silencing of the Ca(V)3.2 T-type calcium channels in sensory neurons alleviates hyperalgesia in rats with streptozocin-induced diabetic neuropathy. Pain. 2009, 145, 184-95.
[Non-Patent Document 5] Jagodic M M, Pathirathna S, Nelson M T, Mancuso S, Joksovic P M, Rosenberg E R, Bayliss D A, Jevtovic-Todorovic V, Todorovic S M.; Cell-specific alterations of T-type calcium current in painful diabetic neuropathy enhance excitability of sensory neurons. J Neurosci. 2007, 27, 3305-16.
[Non-Patent Document 6] Marger F, Gelot A, Alloui A, Matricon J, Ferrer J E, Barrere C, Pizzoccaro A, Muller E, Nargeot J, Snutch T P, Eschalier A, Bourinet E, Ardid D.; T-type calcium channels contribute to colonic hypersensitivity in a rat model of irritable bowel syndrome. Proc Natl Acad Sci USA. 2011, 5. 11268-73.

SUMMARY OF THE INVENTION

Problems to be Solved by the Invention

An object of the present invention is to provide a cyclopropanecarboxamide compound having a diamide structure and having a voltage-dependent T-type calcium channel inhibitory action, and to provide a voltage-dependent T-type calcium channel inhibitor containing the compound as an active ingredient.

Means to Solve the Problems

The present inventors have conducted studies on the voltage-dependent T-type calcium channel inhibitor and as a result, found that a cyclopropanecarboxamide compound having a diamide structure which is a different structure from the compounds described in the above-mentioned Patent Document 1 to Patent Document 7 has an excellent T-type calcium channel inhibitory action, and thereby the present invention has been completed.

That is, the present invention relates to a compound represented by the following General Formula (I), a tautomer, a stereoisomer, or a pharmaceutically acceptable salt of the compound, or a solvate thereof.

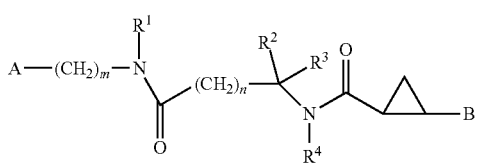

(I)

(In the formula,

A represents a benzene ring which may have a substituent; a 4- to 6-membered heterocyclic ring having one to three same or different heteroatoms selected from an oxygen atom, a sulfur atom, and a nitrogen atom, and a carbon atom, as a ring-constituting atom; or a hetero-fused ring consisting of the heterocyclic ring, and a benzene ring or a 6-membered heteroaryl ring having one or two nitrogen atoms and a carbon atom, in which the heterocyclic ring and the hetero-fused ring may have a substituent, and are bonded to $(CH_2)_m$ via a carbon atom constituting these rings;

B represents a 5- or 6-membered heteroaryl ring having one to three same or different heteroatoms selected from an oxygen atom, a sulfur atom, and a nitrogen atom, and a carbon atom, as a ring-constituting atom, or a hetero-fused ring consisting of the heteroaryl ring, and a benzene ring or a 6-membered heteroaryl ring having one or two nitrogen atoms and a carbon atom, in which the heteroaryl ring and the hetero-fused ring may have a substituent, and are bonded to a cyclopropyl group via a carbon atom constituting these rings;

$R^1$ represents a hydrogen atom or an alkyl group having 1 to 6 carbon atoms, or forms $(CH_2)_p$ together with $R^2$, in which p represents 1, 2, or 3;

$R^2$ and $R^3$ may be the same as or different from each other, and each represents a hydrogen atom, an alkyl group having 1 to 6 carbon atoms, or an alkyl group having 1 to 6 carbon atoms which is substituted with an alkoxy group having 1 to 6 carbon atoms, or $R^2$ and $R^3$ together form $CH_2$—X—$CH_2$, in which X represents a bond, $CH_2$, $CH_2CH_2$, $CH_2CH_2CH_2$, or $CH_2N(R^5)CH_2$, in which $R^5$ represents a hydrogen atom or an alkyl group having 1 to 6 carbon atoms;

$R^4$ represents a hydrogen atom or an alkyl group having 1 to 6 carbon atoms, or forms $(CH_2)_q$ together with R', in which q represents 2, 3, or 4;

m represents 0, 1, or 2; and n represents 0 or 1.)

The present invention also relates to a compound represented by the following General Formula (II), a tautomer, a stereoisomer, or a pharmaceutically acceptable salt of the compound, or a solvate thereof.

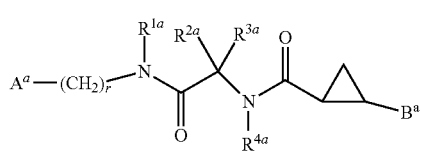

(II)

(In the formula, $A^a$ represents a phenyl group, or a heterocyclic ring which is selected from a pyridyl group, a pyrazinyl group, an azetidinyl group, a pyrrolidinyl group, and a piperidinyl group, which may be substituted with one to five same or different substituents selected from a halogen atom, a hydroxy group, a cyano group, an alkyl group having 1 to 6 carbon atoms, an alkoxy group having 1 to 6 carbon atoms, an alkyl group having 1 to 6 carbon atoms which is substituted with one to three halogen atoms, an alkoxy group having 1 to 6 carbon atoms which is substituted with one to three halogen atoms, an (alkoxy group having 1 to 6 carbon atoms) carbonyl group, an acyl group having 1 to 7 carbon atoms, an alkylsulfonyl group having 1 to 6 carbon atoms, a carbamoyl group which may be substituted with one or two alkyl groups having 1 to 6 carbon atoms, and a 4- to 6-membered cyclic aminocarbonyl group, in which $A^a$ is bonded to $(CH_2)_r$ via a carbon atom constituting a heterocyclic ring;

$B^a$ represents a benzimidazol-2-yl group which may be substituted with one to five same or different substituents selected from a halogen atom, a hydroxy group, a cyano group, an alkyl group having 1 to 6 carbon atoms, an alkoxy group having 1 to 6 carbon atoms, an alkyl group having 1 to 6 carbon atoms which is substituted with one to three halogen atoms, an alkoxy group having 1 to 6 carbon atoms which is substituted with one to three halogen atoms, an (alkoxy group having 1 to 6 carbon atoms) carbonyl group, an acyl group having 1 to 7 carbon atoms, an alkylsulfonyl group having 1 to 6 carbon atoms, a carbamoyl group which may be substituted with one or two alkyl groups having 1 to 6 carbon atoms, and a 4- to 6-membered cyclic aminocarbonyl group;

$R^{1a}$ represents a hydrogen atom or an alkyl group having 1 to 6 carbon atoms;

$R^{2a}$ and $R^{1a}$ may be the same as or different from each other, and each represents a hydrogen atom, an alkyl group having 1 to 6 carbon atoms, or an alkyl group having 1 to 6 carbon atoms which is substituted with an alkoxy group having 1 to 6 carbon atoms, or $R^{2a}$ and $R^{1a}$ together form $CH_2CH_2$ or $CH_2CH_2CH_2$;

$R^{4a}$ represents a hydrogen atom or an alkyl group having 1 to 8 carbon atoms, or represents $(CH_2)_s$ together with $R^{1a}$, in which s represents 2, 3, or 4; and r represents 0, 1, or 2.)

The present invention also relates to a compound represented by the following General Formula (III), a tautomer, a stereoisomer, or a pharmaceutically acceptable salt of the compound, or a solvate thereof.

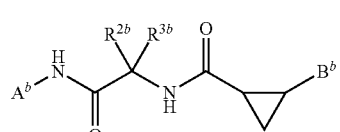

(III)

(In the formula, $A^b$ represents a phenyl group or a pyridyl group, which may be substituted with one to three same or different substituents selected from a halogen atom, an alkyl group having 1 to 6 carbon atoms, an alkoxy group having 1 to 6 carbon atoms, an alkyl group having 1 to 6 carbon atoms which is substituted with one to three halogen atoms, an alkoxy group having 1 to 6 carbon atoms which is substituted with one to three halogen atoms, a carbamoyl group which may be substituted with one or two alkyl groups having 1 to 6 carbon atoms, and a 4- to 6-membered cyclic aminocarbonyl group;

$B^b$ represents a benzimidazol-2-yl group which may be substituted with one to three same or different substituents selected from a halogen atom, an alkyl group having 1 to 6 carbon atoms, an alkoxy group having 1 to 6 carbon atoms, an alkyl group having 1 to 6 carbon atoms which is substituted with one to three halogen atoms, and an alkoxy group having 1 to 6 carbon atoms which is substituted with one to three halogen atoms; and $R^{2b}$ and $R^{3b}$ may be the same as or different from each other, and each represents a hydrogen atom, an alkyl group having 1 to 6 carbon atoms, or an alkyl group having 1 to 6 carbon atoms which is substituted with an alkoxy group having 1 to 6 carbon atoms, or $R^{2b}$ and $R^{3b}$ together form $CH_2CH_2$ or $CH_2CH_2CH_2$.)

The present invention also relates to a pharmaceutical composition containing the compound represented by General Formula (I), (II), or (III) above, a tautomer, a stereoisomer, or a pharmaceutically acceptable salt of the compound, or a solvate thereof, as an active ingredient.

The present invention also relates to a voltage-dependent T-type calcium channel inhibitor containing the compound represented by General Formula (I), (II), or (III) above, a tautomer, a stereoisomer, or a pharmaceutically acceptable salt of the compound, or a solvate thereof, as an active ingredient.

The present invention also relates to an agent for treating or preventing a disease associated with a T-type calcium channel, containing the compound represented by General Formula (I), (II), or (III) above, a tautomer, a stereoisomer, or a pharmaceutically acceptable salt of the compound, or a solvate thereof, as an active ingredient.

The present invention also relates to an agent for treating or preventing acute pain, chronic pain, or neuropathic pain, containing the compound represented by General Formula (I), (II), or (III) above, a tautomer, a stereoisomer, or a pharmaceutically acceptable salt of the compound, or a solvate thereof, as an active ingredient.

The present invention also relates to use of the compound, a tautomer, a stereoisomer, or a pharmaceutically acceptable salt of the compound represented by General Formula (I), (II), or (III) above, or a solvate thereof, for prevention or treatment of acute pain, chronic pain, or neuropathic pain.

Furthermore, the present invention relates to a method of treating acute pain, chronic pain, or neuropathic pain in a human, the method including a step of administering an effective amount of the compound represented by General Formula (I), (II), or (III) above, a tautomer, a stereoisomer, or a pharmaceutically acceptable salt of the compound, or a solvate thereof to a human.

Effects of the Invention

The compound of the present invention has an excellent voltage-dependent T-type calcium channel inhibitory action.

EMBODIMENTS FOR CARRYING OUT THE INVENTION

Figure 1:
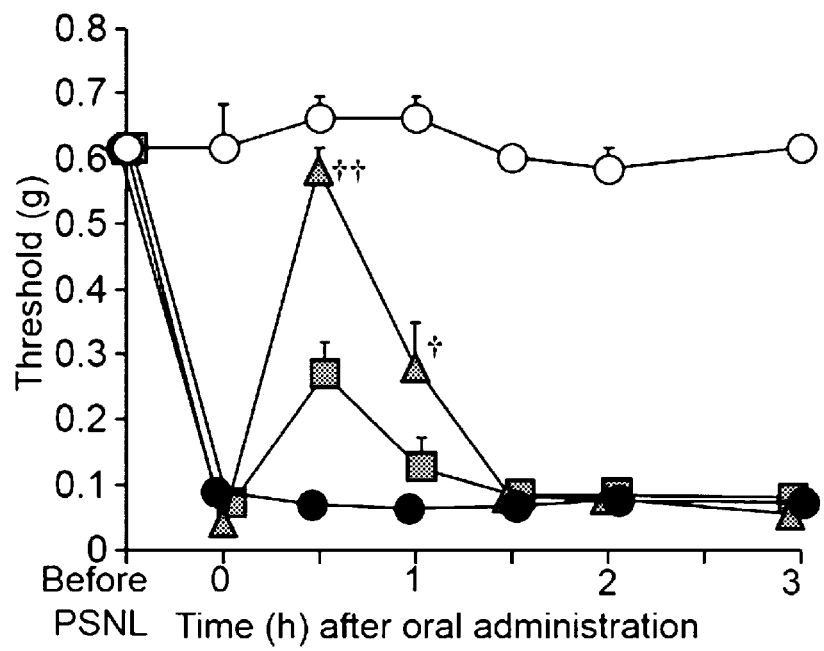
FIG. 1 shows test results of allodynia in a PSNL model using a compound described in Example 5A.

Hereinafter, the present invention will be described in more detail.

In the present specification, examples of the alkyl group having 1 to 6 carbon atoms include linear, branched, or cyclic alkyl groups such as a methyl group, an ethyl group, a propyl group, an iso-propyl group, a butyl group, a cyclopropyl group, a cyclopentyl group, a cyclohexyl group, an iso-butyl group, a tert-butyl group, a pentyl group, or a hexyl group.

Examples of the alkyl group having 1 to 6 carbon atoms which is substituted with one to three halogen atoms include a methyl group, an ethyl group, a propyl group, an iso-propyl group, a butyl group, or a tert-butyl group, which is substituted with one to three halogen atoms such as a fluorine atom, a chlorine atom, or a bromine atom, and preferred examples thereof include a trifluoromethyl group, a chloromethyl group, a 2-chloroethyl group, a 2-bromoethyl group, or a 2-fluoroethyl group.

Examples of the alkoxy group having 1 to 6 carbon atoms include a methoxy group, an ethoxy group, a propoxy group, an iso-propoxy group, a butoxy group, an iso-butoxy group, a tert-butoxy group, a pentyloxy group, or a hexyloxy group.

Examples of the alkoxy group having 1 to 6 carbon atoms which is substituted with one to three halogen atoms include a methoxy group, an ethoxy group, a propoxy group, an iso-propoxy group, a butoxy group, or a tert-butoxy group, which is substituted with one to three halogen atoms such as a fluorine atom, a chlorine atom, or a bromine atom, and preferred examples thereof include a trifluoromethoxy group, a chloromethoxy group, a 2-chloroethoxy group, a 2-bromoethoxy group, a 2-fluoroethoxy group, or a 2,2,2-trifluoroethoxy group.

Examples of the halogen atom include a fluorine atom, a chlorine atom, or a bromine atom.

Examples of the (alkoxy group having 1 to 6 carbon atoms) carbonyl group include an ethoxycarbonyl group, a butoxycarbonyl group, or a tert-butoxycarbonyl group.

Examples of the acyl group having 1 to 7 carbon atoms include an acetyl group, a propionyl group, or a benzoyl group.

Examples of the alkylsulfonyl group having 1 to 6 carbon atoms include a methylsulfonyl group or an ethylsulfonyl group.

Examples of the carbamoyl groups which may be substituted with one or two alkyl groups having 1 to 6 carbon atoms include a N,N-dimethylcarbamoyl group or a N-cyclopropylcarbamoyl group.

Examples of the 4- to 6-membered cyclic aminocarbonyl group include a pyrrolidine-1-carbonyl group, a piperidine-1-carbonyl group, a morpholine-1-carbonyl group, or a piperazine-1-carbonyl group.

Examples of the alkyl group having 1 to 6 carbon atoms which is substituted with an alkoxy group having 1 to 6 carbon atoms include linear, branched, or cyclic alkyl groups such as a methyl group, an ethyl group, a propyl group, an iso-propyl group, a butyl group, a cyclopropyl group, a cyclopentyl group, a cyclohexyl group, an iso-butyl group, a tert-butyl group, a pentyl group, or a hexyl group, which is substituted with an alkoxy group having 1 to 6 carbon atoms such as a methoxy group, an ethoxy group, a propoxy group, an iso-propoxy group, a butoxy group, an iso-butoxy group, a tert-butoxy group, a pentyloxy group, or a hexyloxy group.

As the 4- to 6-membered heterocyclic ring which is represented by A and has one to three same or different heteroatoms selected from an oxygen atom, a sulfur atom, and a nitrogen atom, and a carbon atom, as a ring-constituting atom, pyridine, pyrazine, azetidine, pyrrolidine, piperidine, oxazole, pyrimidine, furan, and thiophene are exemplary examples.

As the hetero-fused ring which is represented by A and consists of a 4- to 6-membered heterocyclic ring having one to three same or different heteroatoms selected from an oxygen atom, a sulfur atom, and a nitrogen atom, and a carbon atom, as a ring-constituting atom, and a benzene ring or a 6-membered heteroaryl ring having one or two nitrogen atoms and a carbon atom, quinoline, isoquinoline, benzimidazole, pyridopyrazine, and purine are exemplary examples.

As the 5- or 6-membered heteroaryl ring which is represented by B and has one to three same or different heteroatoms selected from an oxygen atom, a sulfur atom, and a nitrogen atom, and a carbon atom, as a ring-constituting atom, pyridine, pyrrole, and oxazole are exemplary examples.

As the hetero-fused ring which is represented by B and consists of a 5- or 6-membered heteroaryl ring having one to three same or different heteroatoms selected from an oxygen atom, a sulfur atom, and a nitrogen atom, and a carbon atom, as a ring-constituting atom, and a benzene ring or a 6-membered heteroaryl ring having one or two nitrogen atoms and a carbon atom, benzimidazole, benzoxazole, indazole, indole, and pyridopyrazine are exemplary examples.

In A, as the substituent of the benzene ring which may have a substituent and the substituent which the 4- to 6-membered heterocyclic ring having one to three same or different heteroatoms selected from an oxygen atom, a sulfur atom, and a nitrogen atom, and a carbon atom, as a ring-constituting atom, or the hetero-fused ring consisting of the heterocyclic ring, and a benzene ring or a 6-membered heteroaryl ring having one or two nitrogen atoms and a carbon atom may have, in addition to the substituent which the phenyl group represented by $A^a$ may have, a carboxy group, a nitro group, an amino group, an alkylamino group having 1 to 6 carbon atoms, and a dialkylamino group having 2 to 12 carbon atoms are exemplary examples.

In B, as the substituent which the 5- or 6-membered heteroaryl ring having one to three same or different heteroatoms selected from an oxygen atom, a sulfur atom, and a nitrogen atom, and a carbon atom, as a ring-constituting atom, or the hetero-fused ring consisting of the heteroaryl ring, and a benzene ring or a 6-membered heteroaryl ring having one or two nitrogen atoms and a carbon atom may have, in addition to the substituent which the benzimidazol-2-yl group represented by $B^a$ may have, a carboxy group, a nitro group, an amino group, an alkylamino group having 1 to 6 carbon atoms, and a dialkylamino group having 2 to 12 carbon atoms are exemplary examples.

Among compounds represented by General Formula (I) above, tautomers, stereoisomers, or pharmaceutically acceptable salts of the compounds, or solvates thereof, preferred examples thereof include the following.

(1)
The compound represented by General Formula (I) above, a tautomer, a stereoisomer, or a pharmaceutically acceptable salt of the compound, or a solvate thereof, in which A is a benzene ring which may have a substituent, or a 4- to 6-membered heterocyclic ring which may have a substituent and has one or two nitrogen atoms and a carbon atom, as a ring-constituting atom.

(2)
The compound represented by General Formula (I) above, a tautomer, a stereoisomer, or a pharmaceutically acceptable salt of the compound, or a solvate thereof, in which A is a benzene ring which may have a substituent, or a heterocyclic ring which is selected from a pyridyl group, a pyrazinyl group, an azetidinyl group, a pyrrolidinyl group, and a piperidinyl group, which may have a substituent.

(3)
The compound represented by General Formula (I) above, a tautomer, a stereoisomer, or a pharmaceutically acceptable salt of the compound, or a solvate thereof, in which A is a phenyl group, or a heterocyclic ring which is selected from a pyridyl group, a pyrazinyl group, an azetidinyl group, a pyrrolidinyl group, and a piperidinyl group, which may be substituted with one to five same or different substituents selected from a halogen atom, a hydroxy group, a cyano group, a carboxy group, an amino group, a nitro group, an alkyl group having 1 to 6 carbon atoms, an alkoxy group having 1 to 6 carbon atoms, an alkyl group having 1 to 6 carbon atoms which is substituted with one to three halogen atoms, an alkoxy group having 1 to 6 carbon atoms which is substituted with one to three halogen atoms, an (alkoxy group having 1 to 6 carbon atoms) carbonyl group, an acyl group having 1 to 7 carbon atoms, an alkylsulfonyl group having 1 to 6 carbon atoms, a carbamoyl group which may be substituted with one or two alkyl groups having 1 to 6 carbon atoms, and a 4- to 6-membered cyclic aminocarbonyl group.

(4)
The compound represented by General Formula (I) above or described in any one of (1) to (3) above, a tautomer, a stereoisomer, or a pharmaceutically acceptable salt of the compound, or a solvate thereof, in which B is a hetero-fused ring which may be substituted with a substituent and consists of a 5-membered heteroaryl ring having one or two nitrogen atoms and a carbon atom, as a ring-constituting atom, and a benzene ring.

(5)
The compound represented by General Formula (I) above or described in any one of (1) to (3) above, a tautomer, a stereoisomer, or a pharmaceutically acceptable salt of the compound, or a solvate thereof, in which B is a benzimidazol-2-yl group, an indol-3-yl group, a benzoxazol-2-yl group, or an indazol-6-yl group, which may be substituted with one to five same or different substituents selected from a halogen atom, a hydroxy group, a cyano group, a carboxy group, an amino group, a nitro group, an alkyl group having 1 to 6 carbon atoms, an alkoxy group having 1 to 6 carbon atoms, an alkyl group having 1 to 6 carbon atoms which is substituted with one to three halogen atoms, an alkoxy group having 1 to 6 carbon atoms which is substituted with one to three halogen atoms, an (alkoxy group having 1 to 6 carbon atoms) carbonyl group, an acyl group having 1 to 7 carbon atoms, an alkylsulfonyl group having 1 to 6 carbon atoms, a carbamoyl group which may be substituted with one or two alkyl groups having 1 to 6 carbon atoms, and a 4- to 6-membered cyclic aminocarbonyl group.

(6)
The compound represented by General Formula (I) above or described in any one of (1) to (3) above, a tautomer, a stereoisomer, or a pharmaceutically acceptable salt of the compound, or a solvate thereof, in which B is a benzimidazol-2-yl group.

(7)
The compound represented by General Formula (I) above or described in any one of (1) to (6) above, a tautomer, a stereoisomer, or a pharmaceutically acceptable salt of the compound, or a solvate thereof, in which $R^1$ is a hydrogen atom.

(8)
The compound represented by General Formula (I) above or described in any one of (1) to (7) above, a tautomer, a stereoisomer, or a pharmaceutically acceptable salt of the compound, or a solvate thereof, in which $R^2$ and $R^3$ may be the same as or different from each other, and each represents a hydrogen atom or an alkyl group having 1 to 6 carbon atoms.

(9)

The compound represented by General Formula (I) above or described in any one of (1) to (7) above, a tautomer, a stereoisomer, or a pharmaceutically acceptable salt of the compound, or a solvate thereof, in which $R^2$ and $R^3$ together form $CH_2CH_2$ or $CH_2CH_2CH_2$.

(10)

The compound represented by General Formula (I) above or described in any one of (1) to (9) above, a tautomer, a stereoisomer, or a pharmaceutically acceptable salt of the compound, or a solvate thereof, in which $R^4$ is a hydrogen atom.

(11)

The compound represented by General Formula (I) above or described in any one of (1) to (10) above, a tautomer, a stereoisomer, or a pharmaceutically acceptable salt of the compound, or a solvate thereof, in which m is 0.

(12)

The compound represented by General Formula (I) above or described in any one of (1) to (11) above, a tautomer, a stereoisomer, or a pharmaceutically acceptable salt of the compound, or a solvate thereof, in which n is 0.

Among compounds represented by General Formula (II) above, tautomers, stereoisomers, or pharmaceutically acceptable salts of the compounds, or solvates thereof, preferred examples thereof include the following.

(13)

The compound represented by General Formula (II) above, a tautomer, a stereoisomer, or a pharmaceutically acceptable salt of the compound, or a solvate thereof, in which $A^a$ is a phenyl group or a pyridyl group, which may be substituted with one to three same or different substituents selected from a halogen atom, an alkyl group having 1 to 6 carbon atoms, an alkoxy group having 1 to 6 carbon atoms, an alkyl group having 1 to 6 carbon atoms which is substituted with one to three halogen atoms, and an alkoxy group having 1 to 6 carbon atoms which is substituted with one to three halogen atoms.

(14)

The compound represented by General Formula (II) above, a tautomer, a stereoisomer, or a pharmaceutically acceptable salt of the compound, or a solvate thereof, in which $A^a$ is a phenyl group or a pyridyl group, which may be substituted with one to three same or different substituents selected from a trifluoromethyl group, a trifluoromethoxy group, a fluorine atom, and an alkyl group having 1 to 4 carbon atoms.

(15)

The compound represented by General Formula (II) above or described in (13) or (14) above, a tautomer, a stereoisomer, or a pharmaceutically acceptable salt of the compound, or a solvate thereof, in which $B^a$ is a benzimidazol-2-yl group.

(16)

The compound represented by General Formula (II) above or described in any one of (13) to (15) above, a tautomer, a stereoisomer, or a pharmaceutically acceptable salt of the compound, or a solvate thereof, in which $R^{1a}$ is a hydrogen atom.

(17)

The compound represented by General Formula (II) above or described in any one of (13) to (16) above, a tautomer, a stereoisomer, or a pharmaceutically acceptable salt of the compound, or a solvate thereof, in which $R^{2a}$ is a hydrogen atom and $R^{3a}$ is a methyl group.

(18)

The compound represented by General Formula (II) above or described in any one of (13) to (16) above, a tautomer, a stereoisomer, or a pharmaceutically acceptable salt of the compound, or a solvate thereof, in which $R^{2a}$ and $R^{3a}$ together form $CH_2CH_2$ or $CH_2CH_2$.

(19)

The compound represented by General Formula (II) above or described in any one of (13) to (18) above, a tautomer, a stereoisomer, or a pharmaceutically acceptable salt of the compound, or a solvate thereof, in which $R^{4a}$ is a hydrogen atom.

(20)

The compound represented by General Formula (II) above or described in any one of (13) to (19) above, a tautomer, a stereoisomer, or a pharmaceutically acceptable salt of the compound, or a solvate thereof, in which r is 0.

Among compounds represented by General Formula (III) above, tautomers, stereoisomers, or pharmaceutically acceptable salts of the compounds, or solvates thereof, preferred examples thereof include the following.

(21)

The compound represented by General Formula (III) above, a tautomer, a stereoisomer, or a pharmaceutically acceptable salt of the compound, or a solvate thereof, in which $A^b$ is a phenyl group or a pyridyl group, which may be substituted with one to three same or different substituents selected from a trifluoromethyl group, a trifluoromethoxy group, a fluorine atom, and an alkyl group having 1 to 4 carbon atoms.

(22)

The compound represented by General Formula (III) above or described in (21) above, a tautomer, a stereoisomer, or a pharmaceutically acceptable salt of the compound, or a solvate thereof, in which $B^b$ is a benzimidazol-2-yl group.

(23)

The compound represented by General Formula (III) above or described in (21) or (22) above, a tautomer, a stereoisomer, or a pharmaceutically acceptable salt of the compound, or a solvate thereof, in which $R^{2b}$ is a hydrogen atom and $R^{3b}$ is a methyl group.

(24)

The compound represented by General Formula (III) above or described in (21) or (22) above, or any one of claims 23 to 25, a tautomer, a stereoisomer, or a pharmaceutically acceptable salt of the compound, or a solvate thereof, in which $R^{2b}$ and $R^{3b}$ together form $CH_2CH_2$ or $CH_2CH_2CH_2$.

Furthermore, as the compound of the present invention, the following compounds, tautomers, stereoisomers, or pharmaceutically acceptable salts of the compounds, or solvates thereof are preferable.

A compound, a tautomer, a stereoisomer, or a pharmaceutically acceptable salt of the compound, or a solvate thereof, in which the compound is selected from (1S, 2S)-2-(1H-benzo[d]imidazol-2-yl)-N—((R)-1-oxo-1-((4-propylphenyl)amino)propan-2-yl) cyclopropane-1-carboxamide, (1S, 2S)-2-(1H-benzo[d]imidazol-2-yl)-N—((S)-1-oxo-1-((4-propylphenyl)amino)propan-2-yl) cyclopropane-1-carboxamide, (1R, 2R)-2-(1H-benzo[d]imidazol-2-yl)-N—((R)-1-oxo-1-((4-propylphenyl)amino)propan-2-yl) cyclopropane-1-carboxamide, (1R, 2R)-2-(1H-benzo[d]imidazol-2-yl)-N—((S)-1-oxo-1-((4-propylphenyl)amino)propan-2-yl) cyclopropane-1-carboxamide, (1S, 2S)-2-(1H-benzo[d]imidazol-2-yl)-N—((R)-1-((4-isopropoxyphenyl)amino)-1-oxopropan-2-yl) cyclopropane-1-carboxamide,
(1S, 2S)-2-(1H-benzo[d]imidazol-2-yl)-N—((S)-1-((4-isopropoxyphenyl)amino)-1-oxopropan-2-yl) cyclopropane-1-carboxamide,
(1S, 2S)-2-(1H-benzo[d]imidazol-2-yl)-N—((R)-1-oxo-1-((4-(trifluoromethyl)phenyl)amino)propan-2-yl) cyclopropane-1-carboxamide,
(1S, 2S)-2-(1H-benzo[d]imidazol-2-yl)-N—((S)-1-oxo-1-((4-(trifluoromethyl)phenyl)amino)propan-2-yl) cyclopropane-1-carboxamide,
(1S, 2S)-2-(1H-benzo[d]imidazol-2-yl)-N—((R)-1-oxo-1-((6-(trifluoromethyl)pyridin-3-yl)amino)propan-2-yl) cyclopropane-1-carboxamide,
(1S, 2S)-2-(1H-benzo[d]imidazol-2-yl)-N—((S)-1-oxo-1-((6-(trifluoromethyl)pyridin-3-yl)amino)propan-2-yl) cyclopropane-1-carboxamide,
(1S, 2S)-2-(1H-benzo[d]imidazol-2-yl)-N—((R)-1-((4-cyanophenyl)amino)-1-oxopropan-2-yl) cyclopropane-1-carboxamide,
(1S, 2S)-2-(1H-benzo[d]imidazol-2-yl)-N—((S)-1-((4-cyanophenyl)amino)-1-oxopropan-2-yl) cyclopropane-1-carboxamide,
(1S, 2S)-2-(1H-benzo[d]imidazol-2-yl)-N—((R)-1-((4-(tert-butyl)phenyl)amino)-1-oxopropan-2-yl) cyclopropane-1-carboxamide,
(1S, 2S)-2-(1H-benzo[d]imidazol-2-yl)-N—((S)-1-((4-(tert-butyl)phenyl)amino)-1-oxopropan-2-yl) cyclopropane-1-carboxamide,
(1S, 2S)-2-(1H-benzo[d]imidazol-2-yl)-N—((R)-1-(methyl (4-(trifluoromethyl)phenyl)amino)-1-oxopropan-2-yl) cyclopropane-1-carboxamide,
(1S, 2S)-2-(1H-benzo[d]imidazol-2-yl)-N—((S)-1-(methyl (4-(trifluoromethyl)phenyl)amino)-1-oxopropan-2-yl) cyclopropane-1-carboxamide,
(1S, 2S)-2-(1H-benzo[d]imidazol-2-yl)-N—((R)-1-((4-(methylsulfonyl)benzyl)amino)-1-oxopropan-2-yl) cyclopropane-1-carboxamide,
(1S, 2S)-2-(1H-benzo[d]imidazol-2-yl)-N—((S)-1-((4-(methylsulfonyl)benzyl)amino)-1-oxopropan-2-yl) cyclopropane-1-carboxamide,
tert-butyl 3-((R)-2-((1S, 2S)-2-(1H-benzo[d]imidazol-2-yl) cyclopropane-1-carboxamido)propanamido) azetidine-1-carboxylate,
tert-butyl 3-((S)-2-((1S, 2S)-2-(1H-benzo[d]imidazol-2-yl) cyclopropane-1-carboxamido)propanamido) azetidine-1-carboxylate,
tert-butyl 4-((R)-2-((1S, 2S)-2-(1H-benzo[d]imidazol-2-yl) cyclopropane-1-carboxamido)propanamido) piperidine-1-carboxylate,
tert-butyl 4-((S)-2-((1S, 2S)-2-(1H-benzo[d]imidazol-2-yl) cyclopropane-1-carboxamido)propanamido) piperidine-1-carboxylate,
(1S, 2S)-2-(1H-benzo[d]imidazol-2-yl)-N—((R)-1-oxo-1-(piperidin-4-ylamino)propan-2-yl) cyclopropane-1-carboxamide,
(1S, 2S)-2-(1H-benzo[d]imidazol-2-yl)-N—((S)-1-oxo-1-(piperidin-4-ylamino)propan-2-yl) cyclopropane-1-carboxamide,
(1S, 2S)-2-(1H-benzo[d]imidazol-2-yl)-N—((R)-1-oxo-1-((1-propionylpiperidin-4-yl)amino)propan-2-yl) cyclopropane-1-carboxamide,
(1S, 2S)-2-(1H-benzo[d]imidazol-2-yl)-N—((S)-1-oxo-1-((1-propionylpiperidin-4-yl)amino)propan-2-yl) cyclopropane-1-carboxamide,
(1S, 2S)-2-(1H-benzo[d]imidazol-2-yl)-N—((R)-1-oxo-1-((4-(trifluoromethyl)benzyl)amino)propan-2-yl) cyclopropane-1-carboxamide,
(1S, 2S)-2-(1H-benzo[d]imidazol-2-yl)-N—((S)-1-oxo-1-((4-(trifluoromethyl)benzyl)amino)propan-2-yl) cyclopropane-1-carboxamide,
(1S, 2S)-2-(1H-benzo[d]imidazol-2-yl)-N—((R)-1-oxo-1-(((6-(trifluoromethyl)pyridin-3-yl)methyl)amino)propan-2-yl) cyclopropane-1-carboxamide,
(1S, 2S)-2-(1H-benzo[d]imidazol-2-yl)-N—((S)-1-oxo-1-(((6-(trifluoromethyl)pyridin-3-yl)methyl)amino)propan-2-yl) cyclopropane-1-carboxamide,
(1S, 2S)-2-(1H-benzo[d]imidazol-2-yl)-N—((R)-1-((4-chlorophenyl)amino)-1-oxopropan-2-yl) cyclopropane-1-carboxamide,
(1S, 2S)-2-(1H-benzo[d]imidazol-2-yl)-N—((S)-1-((4-chlorophenyl)amino)-1-oxopropan-2-yl) cyclopropane-1-carboxamide,
(1S, 2S)-2-(1H-benzo[d]imidazol-2-yl)-N—((R)-1-oxo-1-(pyrazin-2-ylamino)propan-2-yl) cyclopropane-1-carboxamide,
(1S, 2S)-2-(1H-benzo[d]imidazol-2-yl)-N—((S)-1-oxo-1-(pyrazin-2-ylamino)propan-2-yl) cyclopropane-1-carboxamide,
(1R, 2R)-2-(1H-benzo[d]imidazol-2-yl)-N—((R)-1-oxo-1-(pyrazin-2-ylamino)propan-2-yl) cyclopropane-1-carboxamide,
(1R, 2R)-2-(1H-benzo[d]imidazol-2-yl)-N—((S)-1-oxo-1-(pyrazin-2-ylamino)propan-2-yl) cyclopropane-1-carboxamide,
(1S, 2S)-2-(1H-benzo[d]imidazol-2-yl)-N—((R)-1-((5-bromopyrazin-2-yl)amino)-1-oxopropan-2-yl) cyclopropane-1-carboxamide,
(1S, 2S)-2-(1H-benzo[d]imidazol-2-yl)-N—((S)-1-((5-bromopyrazin-2-yl)amino)-1-oxopropan-2-yl) cyclopropane-1-carboxamide,
(1R, 2R)-2-(1H-benzo[d]imidazol-2-yl)-N—((R)-1-((5-bromopyrazin-2-yl)amino)-1-oxopropan-2-yl) cyclopropane-1-carboxamide,
(1R, 2R)-2-(1H-benzo[d]imidazol-2-yl)-N—((S)-1-((5-bromopyrazin-2-yl)amino)-1-oxopropan-2-yl) cyclopropane-1-carboxamide,
(R)-1-((1S, 2S)-2-(1H-benzo[d]imidazol-2-yl) cyclopropane-1-carbonyl)-N-(4-(trifluoromethyl)phenyl) pyrrolidine-2-carboxamide,
(S)-1-((1S, 2S)-2-(1H-benzo[d]imidazol-2-yl) cyclopropane-1-carbonyl)-N-(4-(trifluoromethyl)phenyl) pyrrolidine-2-carboxamide,
(R)-1-((1R, 2R)-2-(1H-benzo[d]imidazol-2-yl) cyclopropane-1-carbonyl)-N-(4-(trifluoromethyl)phenyl) pyrrolidine-2-carboxamide,
(S)-1-((1R, 2R)-2-(1H-benzo[d]imidazol-2-yl) cyclopropane-1-carbonyl)-N-(4-(trifluoromethyl)phenyl) pyrrolidine-2-carboxamide,
(1S, 2S)-2-(1H-benzo[d]imidazol-2-yl)-N-(2-oxo-2-((4-(trifluoromethyl)phenyl)amino)ethyl) cyclopropane-1-carboxamide,
(1R, 2R)-2-(1H-benzo[d]imidazol-2-yl)-N-(2-oxo-2-((4-(trifluoromethyl)phenyl)amino)ethyl) cyclopropane-1-carboxamide,
1-((1S, 2S)-2-(1H-benzo[d]imidazol-2-yl) cyclopropane-1-carboxamido)-N-(4-(trifluoromethyl)phenyl) cyclopropane-1-carboxamide,
1-((1R, 2R)-2-(1H-benzo[d]imidazol-2-yl) cyclopropane-1-carboxamido)-N-(4-(trifluoromethyl)phenyl) cyclopropane-1-carboxamide, 1-((1S, 2S)-2-(1H-benzo[d]imidazol-2-yl) cyclopropane-1-carboxamido)-N-(3-(trifluoromethyl)phenyl) cyclopropane-1-carboxamide, (1S, 2S)-2-(1H-benzo[d]imidazol-2-yl)-N—((R)-2-oxo-1-((4-(trifluoromethyl)phenyl)pyrrolidin-3-yl) cyclopropane-1-carboxamide, (1S, 2S)-2-(1H-benzo[d]imidazol-2-yl)-N—((S)-2-oxo-1-((4-(trifluoromethyl)phenyl)pyrrolidin-3-yl) cyclopropane-1-carboxamide, 1-((1S, 2S)-2-(1H-benzo[d]imidazol-2-yl) cyclopropane-1-carboxamido)-N-(4-(trifluoromethoxy)phenyl) cyclopropane-1-carboxamide, 1-((1S, 2S)-2-(1H-benzo[d]imidazol-2-yl) cyclopropane-1-carboxamido)-N-(2-(trifluoromethyl)phenyl) cyclopropane-1-carboxamide, 1-((1S, 2S)-2-(1-ethyl-1H-benzo[d]imidazol-2-yl) cyclopropane-1-carboxamido)-N-(6-(trifluoromethyl)pyridin-3-yl) cyclopropane-1-carboxamide, 1-((1S, 2S)-2-(1H-benzo[d]imidazol-2-yl) cyclopropane-1-carboxamido)-N-(2-fluoro-4-(trifluoromethyl)phenyl) cyclopropane-1-carboxamide, 1-((1S, 2S)-2-(1H-benzo[d]imidazol-2-yl) cyclopropane-1-carboxamido)-N-(5-(trifluoromethyl)pyridin-3-yl) cyclopropane-1-carboxamide, (1S, 2S)-2-(1H-benzo[d]imidazol-2-yl)-N-(2-(isopropyl(6-(trifluoromethyl)pyridin-3-yl)amino)-2-oxoethyl) cyclopropane-1-carboxamide, 1-((1S, 2S)-2-(1H-benzo[d]imidazol-2-yl) cyclopropane-1-carboxamido)-N-(4-fluoro-3-(trifluoromethyl)phenyl) cyclopropane-1-carboxamide, (1S, 2S)-2-(1H-benzo[d]imidazol-2-yl)-N—((R)-1-((4-fluoro-3-(trifluoromethyl)phenyl)amino)-3-methoxy-1-oxopropan-2-yl) cyclopropane-1-carboxamide, (1S, 2S)-2-(1H-benzo[d]imidazol-2-yl)-N—((S)-1-((4-fluoro-3-(trifluoromethyl)phenyl)amino)-3-methoxy-1-oxopropan-2-yl) cyclopropane-1-carboxamide, (1S, 2S)-2-(1H-benzo[d]imidazol-2-yl)-N—((R)-5-oxo-1-(6-(trifluoromethyl)pyridin-3-yl)pyrrolidin-3-yl) cyclopropane-1-carboxamide, (1S, 2S)-2-(1H-benzo[d]imidazol-2-yl)-N—((S)-5-oxo-1-(6-(trifluoromethyl)pyridin-3-yl)pyrrolidin-3-yl) cyclopropane-1-carboxamide, 1-((1S, 2S)-2-(5-chloro-1H-benzo[d]imidazol-2-yl) cyclopropane-1-carboxamido)-N-(4-fluoro-3-(trifluoromethyl)phenyl) cyclopropane-1-carboxamide, 1-((1S, 2S)-2-(1H-benzo[d]imidazol-2-yl) cyclopropane-1-carboxamido)-N-(3,5-dichlorophenyl) cyclopropane-1-carboxamide, 1-((1S, 2S)-2-(1H-benzo[d]imidazol-2-yl) cyclopropane-1-carboxamido)-N-(3-(trifluoromethyl)phenyl) cyclobutane-1-carboxamide, (1S, 2S)-2-(1H-benzo[d]imidazol-2-yl)-N—((R)-4-methyl-1-oxo-1-((3-(trifluoromethyl)phenyl)amino)pentan-2-yl) cyclopropane-1-carboxamide, (1S, 2S)-2-(1H-benzo[d]imidazol-2-yl)-N—((R)-1-oxo-1-((3-(trifluoromethyl)phenyl)amino)propan-2-yl) cyclopropane-1-carboxamide, (1S, 2S)-2-(1H-benzo[d]imidazol-2-yl)-N—((S)-1-oxo-1-((3-(trifluoromethyl)phenyl)amino)propan-2-yl) cyclopropane-1-carboxamide, 1-((1S, 2S)-2-(1H-benzo[d]imidazol-2-yl) cyclopropane-1-carboxamido)-N-(3-(trifluoromethyl)phenyl) cyclobutane-1-carboxamide, (1S, 2S)-2-(1H-benzo[d]imidazol-2-yl)-N—((R)-4-methyl-1-oxo-1-((3-(trifluoromethyl)phenyl)amino)pentan-2-yl) cyclopropane-1-carboxamide, (1S, 2S)-2-(1H-benzo[d]imidazol-2-yl)-N—((R)-1-oxo-1-((3-(trifluoromethyl)phenyl)amino)propan-2-yl) cyclopropane-1-carboxamide, (1S, 2S)-2-(1H-benzo[d]imidazol-2-yl)-N—((S)-1-oxo-1-((3-(trifluoromethyl)phenyl)amino)propan-2-yl) cyclopropane-1-carboxamide, (1S, 2S)-2-(1H-benzo[d]imidazol-2-yl)-N-(2-oxo-2-((3-(trifluoromethyl)phenyl)amino)ethyl) cyclopropane-1-carboxamide, 1-((1S, 2S)-2-(1-cyclopropyl-1H-benzo[d]imidazol-2-yl) cyclopropane-1-carboxamido)-N-(3-(trifluoromethyl)phenyl) cyclopropane-1-carboxamide, 1-((1S, 2S)-2-(1H-benzo[d]imidazol-2-yl) cyclopropane-1-carboxamido)-N-(2-fluoro-3-(trifluoromethyl)phenyl) cyclopropane-1-carboxamide, 1-((1S, 2S)-2-(1H-benzo[d]imidazol-2-yl) cyclopropane-1-carboxamido)-N-(3-fluoro-5-(trifluoromethyl)phenyl) cyclopropane-1-carboxamide, and 1-((1S, 2S)-2-(1H-benzo[d]imidazol-2-yl) cyclopropane-1-carboxamido)-N-(3-(trifluoromethoxy)phenyl) cyclopropane-1-carboxamide.

Examples of the pharmacologically acceptable salt of the compound represented by General Formula (I), (II), or (III) above include an acid addition salt with mineral acids such as hydrochloric acid, sulfuric acid, and phosphoric acid, an acid addition salt with organic acids such as formic acid, acetic acid, citric acid, tartaric acid, and methanesulfonic acid, salts with inorganic bases such as a sodium salt, a potassium salt, a lithium salt, and a calcium salt, and an addition salt with organic bases such as arginine and piperazine.

The compound of the present invention may have stereoisomers such as a cis or trans isomer, an optically active substance, and a racemate, all are included in the present invention, and furthermore, mixtures of an enantiomer and a diastereomer are also included in the present invention.

Moreover, the compound of the present invention also includes a stable isotope.

The compound of the present invention may be a tautomer, a hydrate, a solvate with an organic solvent such as alcohol, a derivative substituted with a stable isotope such as deuterium, or a prodrug.

Subsequently, a method for producing the compound represented by General Formula (I), (II), or (III) above according to the present invention will be described below, but the method for producing the compound of the present invention is not limited to the following method.

The compounds of the present invention can be produced by using a commercially available compound as a raw material and using a known method or a method described below. Examples of the known method include methods described in the 5th series of Experimental Chemistry (Maruzen Publishing Co., Ltd.), new edition heterocyclic compounds (Kodansha Ltd.), Protective Groups in Organic Synthesis (Wiely), and the like.

Depending on the compound produced using the present production method, protection or deprotection, and conversion or introduction of functional groups may be effective at each stage of the production. In such a case, the method is not limited to the operation or order of the described production method, an appropriate operation or order can be applied using a known method.

The prodrug of the compound according to the present invention can be produced by applying known methods such as amidation, esterification, and alkylation at each step of production.

Depending on the compound produced using the present production method, various salts, hydrates, and crystal polymorphs may be contained. In addition, in a case where an optical isomer, a geometrical isomer, or a tautomer can exist, unless otherwise limited, a mixture in any ratio may be contained. A mixture of these isomers can be separated by known methods.

A method for producing the compound of the present invention will be described below, but the method for producing the compound of the present invention is not limited to the following method.

The following abbreviations may be used in the present specification.

M: molar concentration, N: normal, MS: mass spectrum, [M+H]$^+$: protonated molecular ion peak, [M−H]$^-$: deprotonated molecular ion peak, CDCl$_3$: deuterated chloroform, DMSO-d$_6$: deuterated dimethyl sulfoxide, CD$_3$OD: deuterated methanol, $^1$H NMR: proton nuclear magnetic resonance, Me: methyl group, Et: ethyl group, t-Bu: tert-butyl group, CN: cyano group, CF$_3$: trifluoromethyl group, Ts: p-toluenesulfonyl group, Boc: tert-butoxycarbonyl group, DMF: N,N-dimethylformamide, THF: tetrahydrofuran, DME: 1,2-dimethoxyethane, HATU: O-(7-azabenzotriazol-1-yl)-N,N,N',N'-tetramethyluronium hexafluorophosphate, HOBT: 1-hydroxybenzotriazole, WSC: 1-ethyl-3-(dimethylaminopropyl) carbodiimide, DMT-MM: 4-(4,6-dimethoxy-1,3,5-triazin-2-yl)-4-methylmorpholinium chloride, DMAP: N,N-dimethyl-4-aminopyridine, DIBAL-H: diisobutylaluminium hydride, L-selectride: lithium tri(sec-butyl)borohydride, DIPEA: N,N-diisopropylethylamine, BINAP: 2,2'-bis(diphenylphosphino)-1,1'-binaphthyl, DMSO: dimethyl sulfoxide, FBS: fetal bovine serum, DMEM: Dulbecco's modified Eagle's medium, CO$_2$: carbon dioxide, NaCl: sodium chloride, KCl: Potassium chloride, MgCl$_2$: magnesium chloride, CaCl$_2$: calcium chloride, CsCl: cesium chloride, CsF: cesium fluoride, HEPES: 4-(2-hydroxyethyl)-1-piperazineethanesulfonic acid, EGTA: glycol ether diamine tetraacetic acid, CYP: cytochrome P450, NADP or NADP$^+$: nicotinamide adenine dinucleotide phosphate, G-6-P DH (Y): glucose-6-phosphate, G-6-P DH (Y): glucose-6-phosphate dehydrogenase (derived from yeast), and PSNL: partial sciatic nerve ligation The compound represented by General Formula (I) above, that is, the compound represented by the following general formula may be referred to as Compound (I).

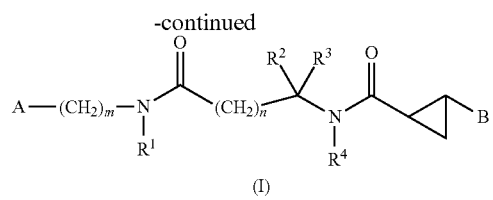

(I)

[Symbols in the formulae are as defined above.]

Compound (I) of the present invention can be produced by reacting Compound (I-A) with Compound (I-B) in a suitable solvent such as DMF at 0° C. to 100° C., in the presence of a condensing agent such as HATU or WSC, as necessary, an additive such as HOBT or DMAP, and as necessary, a base such as triethylamine or DIPEA.

In addition, Compound (I) can be produced by reacting Compound (I-B) with the corresponding carboxylic acid chloride or carboxylic acid anhydride in a suitable solvent such as tetrahydrofuran at 0° C. to 100° C., as necessary, in the presence of a base such as triethylamine, DIPEA, or pyridine.

Moreover, Compound (I) can be produced from Compound (I-A) and Compound (I-B), or derivatives corresponding to the compounds by using a condensation reaction described in Christian A. G. N. Montalbetti, et al, Tetrahedron, 61 (46), 2005, 10827-10852 or a condensation reaction equivalent thereto.

Compound (I-A) can be produced, for example, by the following method.

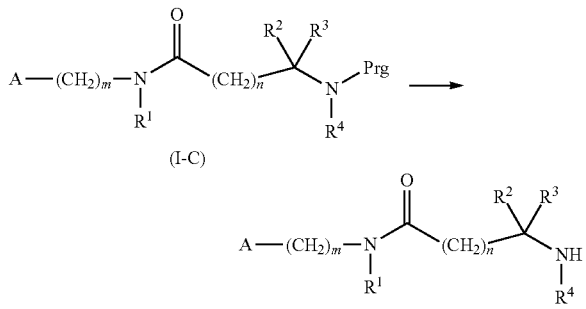

[In the formulae, Prg means a protective group, and represents any functional group capable of being converted to hydrogen by a deprotection reaction. Other symbols are as defined above.]

Compound (I-A) can be produced by reacting Compound (I-C) with an acid such as hydrogen chloride or trifluoroacetic acid in a suitable solvent such as methanol or in the absence of a solvent at −10° C. to 100° C.

In addition, Compound (I-A) can be produced by subjecting Compound (I-C) to a hydrogenation reaction using a catalyst such as palladium carbon or palladium hydroxide, in a suitable solvent such as methanol at 0° C. to 100° C.

Moreover, Compound (I-A) can be produced from Compound (I-C) by using a deprotection reaction of a protective group described in Protective Groups in Organic Synthesis (Wiely) or the like or a deprotection reaction of a protective group equivalent thereto.

In a case where R$^1$ represents a hydrogen atom or an alkyl group having 1 to 6 carbon atoms, Compound (I-C) can be produced, for example, by the following method.

Method for Producing Compound (I)

Compound (I) of the present invention can be produced, for example, by the following method.

(Production Method 1)

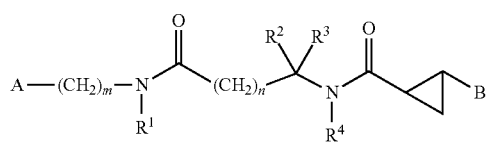

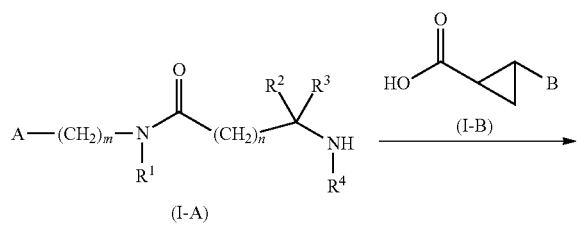

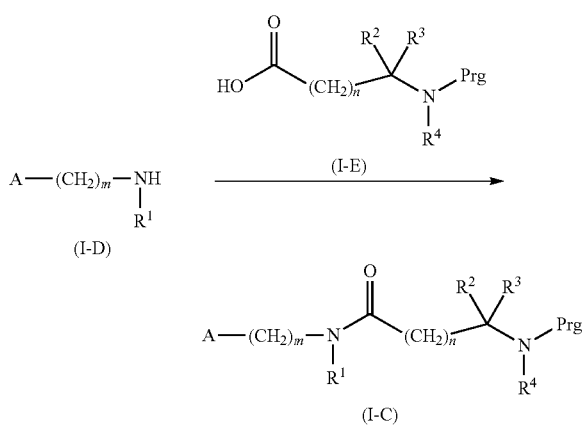

[In the formulae, Prg means a protective group, and represents any functional group capable of being converted to hydrogen by a deprotection reaction. Other symbols are as defined above.]

Compound (I-C) can be produced from (I-D) using Compound (I-E) by the same method as that described in the above-mentioned production method in which Compound (I) is obtained from Compound (I-A) and Compound (I-B).

Compound (I-D) may be a commercially available product or can be produced from a commercially available product by a known method. For example, Compound (I-D) can be produced from a suitable starting material by combining known methods, according to a synthesis method described in Amir E Wahba, et al, J. Org. Chem. 77 (10), 2012, 4578-4585 or known PCT International Publication No. WO 2013/186692, or a synthesis method equivalent thereto.

Compound (I-E) may be a commercially available product or can be produced from a commercially available product by a known method. For example, Compound (I-E) can be produced from a suitable starting material by combining known methods, according to a synthesis method described in PCT International Publication No. WO 2013/072933 or PCT International Publication No. WO 2006/102243 which is known, or a synthesis method equivalent thereto.

In a case where $R^1$ and $R^2$ together represent $(CH_2)p$, Compound (I-C) can be produced, for example, by the following method.

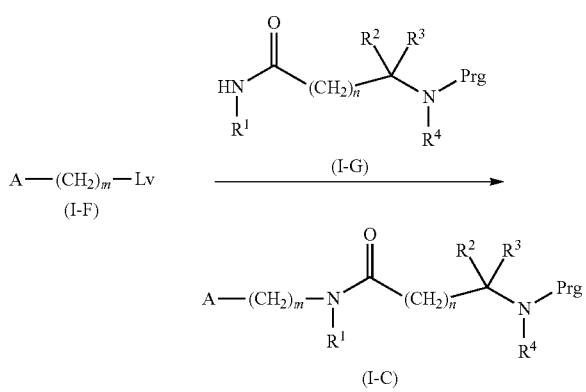

[In the formulae, Prg means a protective group, and represents any functional group capable of being converted to hydrogen by a deprotection reaction. Lv represents a leaving group. Other symbols are as defined above.]

Compound (I-C) of the present invention can be produced by reacting Compound (I-F) with Compound (I-G) in a suitable solvent such as DMF at 0° C. to 200° C., in the presence of a metal catalyst such as tris(dibenzylideneacetone) dipalladium or copper iodide, as necessary, a ligand such as BINAP or ethylenediamine, and as necessary, a base such as triethylamine or DIPEA. As the leaving group, a suitable functional group such as halogen or a tosyl group is used.

Moreover, Compound (I-C) can be produced by reacting Compound (I-F) with Compound (I-G) in a suitable solvent such as DMF at 0° C. to 200° C., in the presence of a base such as sodium hydride or cesium carbonate.

In addition, Compound (I-C) can be produced from Compound (I-F) and Compound (I-G), or derivatives corresponding to the compounds by using a reaction equivalent to the above reaction.

Compound (I-F) may be a commercially available product or can be produced from a commercially available product by a known method.

Compound (I-G) may be a commercially available product or can be produced from a commercially available product by a known method.

Compound (I-B) can be produced, for example, by the following method.

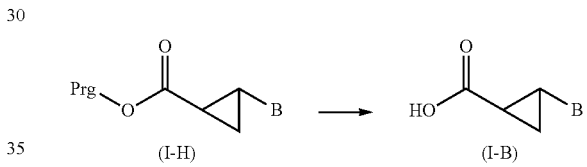

[In the formulae, Prg means a protective group, and represents any functional group capable of being converted to hydrogen by a deprotection reaction. Other symbols are as defined above.]

Compound (I-B) can be produced from Compound (I-H) by reacting Compound (1-H) with a base such as lithium hydroxide or sodium hydroxide in a suitable solvent such as a mixed solvent of water and methanol or tetrahydrofuran at 0° C. to 100° C.

Moreover, Compound (I-B) can be produced from Compound (I-H) by using a deprotection reaction of a protective group described in Protective Groups in Organic Synthesis (Wiely) or the like or a deprotection reaction of a protective group equivalent thereto.

Compound (I-H) may be a commercially available product or can be produced from a commercially available product by a known method. For example, Compound (I-H) can be produced from a suitable starting material by combining known methods, according to a synthesis method described in PCT International Publication No. WO 2010/137351 or PCT International Publication No. WO 2005/016883 which is known or scientific literature Jason A. Miller, J. Org. Chem, 68 (20), 2003, 7884-7886, or a synthesis method equivalent thereto.

(Production Method 2)

In a case where $R^1$ represents a hydrogen atom or an alkyl group having 1 to 6 carbon atoms, Compound (I) of the present invention can be produced, for example, by the following method.

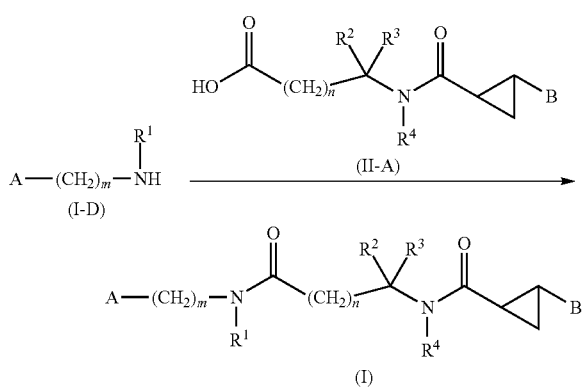

[Symbols in the formulae are as defined above.]

Compound (I) of the present invention can be produced from (I-D) using Compound (II-A) by the same method as that described in the above-mentioned Production method 1 in which Compound (I) is obtained from Compound (I-A) and Compound (I-B).

Compound (II-A) can be produced, for example, by the following method.

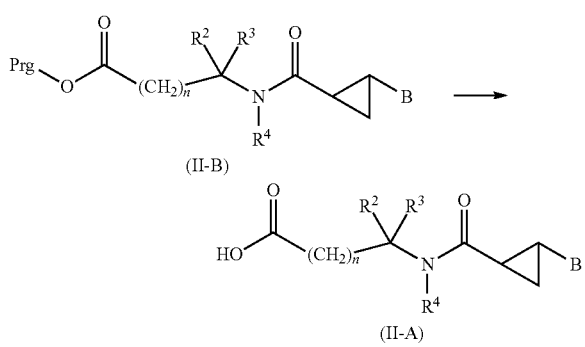

[In the formulae, Prg means a protective group, and represents any functional group capable of being converted to hydrogen by a deprotection reaction. Other symbols are as defined above.]

Compound (II-A) can be produced from (II-B) by the same method as the method for producing Compound (I-B).

Compound (II-B) can be produced, for example, by the following method.

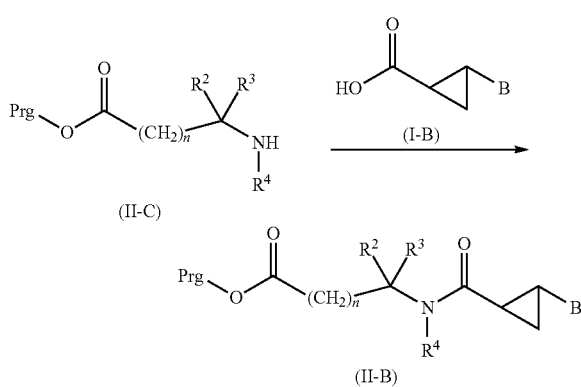

[In the formulae, Prg means a protective group, and represents any functional group capable of being converted to hydrogen by a deprotection reaction. Other symbols are as defined above.]

Compound (II-B) can be produced from (II-C) by the same method as that described in the above-mentioned Production method 1 in which Compound (I) is obtained from Compound (I-A) and Compound (I-B).

Compound (II-C) may be a commercially available product or can be produced from a commercially available product by a known method.

Furthermore, the compound represented by General Formula (II) above, that is, the compound represented by the following general formula:

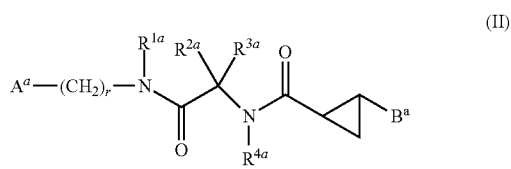

can also be produced by the above-mentioned Production method 1 and Production method 2.

Furthermore, similarly, the compound represented by General Formula (III) above, that is, the compound represented by the following general formula:

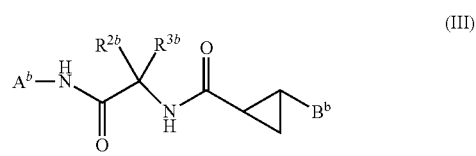

can also be produced by the above-mentioned Production method 1 and Production method 2.

Hereinafter, the pharmacological action of the compound of the present invention will be described.

In Example 44 described later, results of a pharmacological test on a voltage-dependent T-type calcium inhibitory action of the compound of the present invention by measuring an intracellular calcium concentration using a human Cav3.2 channel-stably expressed cell are described.

As is clear from Tables 1 to 3, the compound of the present invention was found to have an excellent voltage-dependent T-type calcium inhibitory action.

In addition, in an electrophysiological evaluation using an automated patch clamp system of Example 45 described later, as is clear from Table 4, it was found that the compound of the present invention had an excellent voltage-dependent T-type calcium inhibitory action.

Incidentally, it is known that a calcium channel has a property called state dependence.

That is, the calcium channel takes three states of a stationary (closed) state, an activation (activated or open) state, and an inactivation (inactivated) state according to a difference in membrane potential.

Among the compounds of the present invention, some compounds have a superior voltage-dependent T-type calcium channel inhibitory action in an inactivation state compared to a stationary state or a closed state, and thus these compounds are expected to have a selective voltage-dependent T-type calcium channel inhibitory action.

In neuropathic pain, depolarization is repeated, but among the compounds of the present invention, a compound having a property (frequency dependence) in which the blocking action is enhanced in such a state also exists.

Furthermore, in Example 46 described later, in a pharmacological test on mechanical allodynia in a mouse partial sciatic nerve ligation (PSNL) model, as is clear from FIGS. 1 and 2, by orally administering 30 mg/kg of each of a compound described in Example 5A and a compound described in Example 26, mechanical allodynia can be statistically significantly suppressed compared to a vehicle group.

Therefore, the compound of the present invention is a voltage-dependent T-type calcium channel inhibitor which has an excellent voltage-dependent T-type calcium channel inhibitory action, exhibits a stronger affinity in the inactivation state than in the stationary state, does not cause serious side effects such as cardiotoxicity (hERG), and has a high safety, and can be used for diseases such as neuropathic pain.

That is, as described in Patent Document 7, as the target disease of the compound of the present invention includes pain, pain is mentioned, as a limited target disease, chronic pain is mentioned, and as a further limited target disease, neuropathic pain is mentioned.

Furthermore, as described in the Patent Document, "the pain is classified into chronic pains and acute pains including neuropathic pain, inflammatory pain, cancer pain, and visceral pain, primary diseases of which are exemplified by diabetic neuropathy, traumatic neurological disorder, nerve compression, strangulation, spinal cord injury, cerebral apoplexy, fibromyalgia syndrome, carpal tunnel syndrome, osteoarthritis, rheumatoid arthritis and multiple sclerosis, herpes zoster, herpes simplex, syphilis, nerve disorders induced by cancer chemotherapy, HIV, and HIV treatment, chronic joint pain, postherpetic neuralgia, neuroma pain, trigeminal neuralgia, phantom limb pain, postoperative pain, stump pain, tooth pain, plexus neuropathy, glossopharyngeal neuralgia, laryngeal neuralgia, migraine, carcinomatous neuropathy, polyneuropathy, causalgia, low back pain, complex regional pain syndrome (CRPS), and thalamic pain", and pain derived from causes other than the causes mentioned above is also included in the target disease of the present invention. As described in the Patent Document, examples of target diseases other than pain include "diseases associated with central nervous system (CNS) disorders, diseases associated with bladder function disorders, cerebral apoplexy, itching, atopic dermatitis, hypertension, hyperaldosteronemia, edema, ischemic heart diseases, age-related macular degeneration, cancer, diabetes mellitus, sterility, sexual dysfunction, arrhythmia, and kidney disease. Examples of the diseases associated with central nervous system (CNS) disorders include epilepsy, essential tremor, schizophrenia, Parkinson's disease, manic-depressive illness, bipolar disorder, depression, anxiety, dementia, drug dependence, Huntington's disease, and sleep disturbance. Examples of the diseases associated with bladder function disorder include overactive bladder".

In addition, the compound of the present invention can also be used in combination with a known pain therapeutic agent.

The compound of the present invention can be administered to a human by an appropriate administration method such as oral administration or parenteral administration, but oral administration is preferred.

For formulation, the compound can be produced in a dosage form such as a tablet, a granule, a powder, a capsule, a suspension, an injection, or a suppository by an ordinary method in a technical field of a pharmaceutical preparation.

In such preparation, for example, in a case of the tablet, an ordinary excipient, a disintegrator, a binder, a lubricant, or a dye is used. Here, examples of the excipient include lactose, D-mannitol, crystalline cellulose, and glucose, examples of the disintegrator include starch and carboxy methylcellulose calcium (CMC-Ca), examples of the lubricant include magnesium stearate and talc, and examples of the binder include hydroxypropyl cellulose (HPC), gelatin, and polyvinyl pyrrolidone (PVP). For adjustment of the injection, a solvent, a stabilizer, a solubilizer, a suspension, an emulsifier, a soothing agent, a buffer agent, or a preservative is used.

In a case of an adult, a dosage of the compound of the present invention which is the active ingredient is usually about 0.01 mg to 100 mg per day by the injection, and 1 mg to 2000 mg per day by the oral administration, but can be increased or decreased depending on an age or a symptom.

Next, the present invention will be described in more detail with reference to Reference Examples and Examples, but the present invention is not limited thereto.

In columns, PLC, and TLC used in Reference Examples and Examples, unless otherwise stated, either silica gel or NH silica gel, or both were used. For analysis of a synthesized compound, $^1$H-NMR (400 MHz), an atmospheric pressure ionization high resolution time-of-flight mass spectrometer (ESI), and other appropriate analysis methods were used.

Names of compounds in Reference Examples and Examples are named based on names obtained by converting structural formulas drawn using ChemDraw ver. 14 manufactured by Cambridge Soft Inc. using naming algorithm installed in the same software.

Reference Example 1-1

Trans-(2-(1H-benzo[d]imidazol-2-yl) cyclopropane-1-carbonyl)-D-alanine benzyl

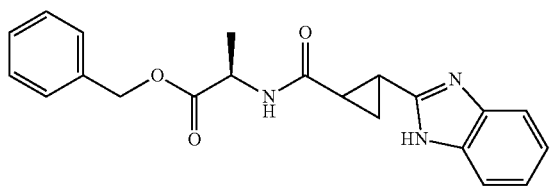 [SMILES: C[C@@H](NC(=O)C1CC1c1nc2ccccc2[nH]1)C(=O)OCc1ccccc1]

D-Alanine benzyl tosylate (1.75 g, 5.0 mmol), trans-2-(1H-benzo[d]imidazol-2-yl) cyclopropane-1-carboxylic acid (1.11 g, 5.5 mmol), and HATU (2.09 g, 5.5 mmol) were dissolved in DMF (30 mL), and then DIPEA (2.61 mL, 15 mmol) was added thereto, followed by stirring at room temperature for two hours. A saturated aqueous sodium hydrogen carbonate solution was added to a reaction liquid, the mixture was stirred for a while, and then extraction was performed with ethyl acetate. A separated organic layer was washed with a saturated saline solution and dried over anhydrous sodium sulfate, an insoluble substance was filtered, and then a solvent was distilled off under reduced pressure. The obtained residue was purified by silica gel column chromatography (ethyl acetate) to obtain Diastereomer A (upper spot on TLC (ethyl acetate), white amorphous, 562 mg, 31%) and Diastereomer B (lower spot on TLC (ethyl acetate), white amorphous, 401 mg, 22%) of a title compound.

Diastereomer A $^{1}$H NMR (CD$_{3}$OD, 400 MHz): δ=1.39 (d, 3H, J=7 Hz), 1.5-1.7 (m, 2H), 2.3-2.4 (m, 1H), 2.5-2.6 (m, 1H), 4.47 (q, 1H, J=8 Hz), 5.13 (d, 1H, J=12 Hz), 5.19 (d, 1H, J=12 Hz), 7.1-7.2 (m, 2H), 7.3-7.6 (m, 7H). 2H cannot be observed.

Diastereomer B $^{1}$H NMR (CD$_{3}$OD, 400 MHz): δ=1.39 (d, 3H, J=7 Hz), 1.5-1.7 (m, 2H), 2.3-2.4 (m, 1H), 2.5-2.6 (m, 1H), 4.47 (q, 1H, J=8 Hz), 5.13 (s, 2H), 7.1-7.4 (m, 7H), 7.4-7.5 (m, 2H). 2H cannot be observed.

Reference Example 1-2

Trans-(2-(1H-benzo[d]imidazol-2-yl) cyclopropane-1-carbonyl)-D-alanine

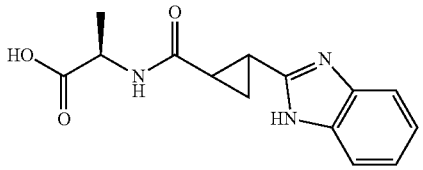 [SMILES: C[C@@H](NC(=O)C1CC1c1nc2ccccc2[nH]1)C(=O)O]

Diastereomer A (562 mg, 1.5 mmol) of trans-(2-(1H-benzo[d]imidazol-2-yl) cyclopropane-1-carbonyl)-D-alanine benzyl synthesized in Reference Example 1-1 was dissolved in methanol (20 mL), and then 10% palladium-carbon (329 mg, 0.15 mmol) was added thereto, followed by stirring at room temperature for 30 minutes under a hydrogen atmosphere. A reaction liquid was filtered through celite, and filtrate was concentrated to obtain a title compound (white powders, 270 mg, 64%).

$^{1}$H NMR (DMSO-d$_{6}$, 400 MHz): δ=1.26 (d, 3H, J=7 Hz), 1.4-1.6 (m, 2H), 2.2-2.5 (m, 2H), 4.22 (quint, 1H, J=7 Hz), 7.0-7.2 (m, 2H), 7.3-7.5 (m, 2H), 8.57 (d, 2H, J=7 Hz), 12.4 (brs, 1H). 1H cannot be observed.

Reference Example 2

Trans-(2-(1H-benzo[d]imidazol-2-yl) cyclopropane-1-carbonyl)-D-alanine

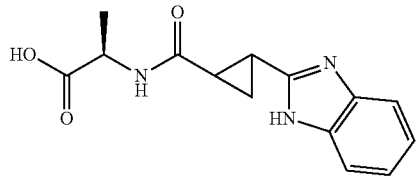 [SMILES: C[C@@H](NC(=O)C1CC1c1nc2ccccc2[nH]1)C(=O)O]

A title compound (white powders, 254 mg, 97%) was obtained in the same manner as in Reference Example 1-2, by using Diastereomer B (350 mg, 0.96 mmol) of trans-(2-(1H-benzo[d]imidazol-2-yl) cyclopropane-1-carbonyl)-D-alanine benzyl synthesized in Reference Example 1-1.

Reference Example 3-1

Benzyl 1-((2-fluoro-4-(trifluoromethyl)phenyl)carbamoyl)cyclopropyl)carbamate

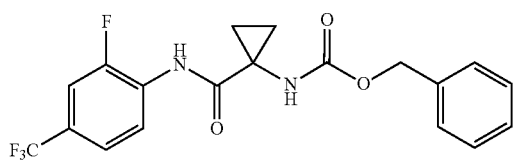 [SMILES: O=C(NC1(C(=O)Nc2ccc(C(F)(F)F)cc2F)CC1)OCc1ccccc1]

A title compound (white powders, 144 mg, 43%) was obtained in the same manner as in Reference Example 1-1, by using 1-(((benzyloxy)carbonyl)amino) cyclopropane-1-carboxylic acid (200 mg, 0.85 mmol) and 2-fluoro-4-(trifluoromethyl)aniline (459 mg, 2.55 mmol).

1H NMR (CD$_{3}$OD, 400 MHz): δ=1.18 (dd, 2H, J=4, 8 Hz), 1.56 (dd, 2H, J=5, 8 Hz), 5.14 (s, 2H), 7.2-7.4 (m, 5H), 7.4-7.6 (m, 2H), 8.0-8.2 (m, 1H). 2H cannot be observed.

Reference Example 3-2

1-Amino-N-(2-fluoro-4-(trifluoromethyl)phenyl) cyclopropane-1-carboxamide

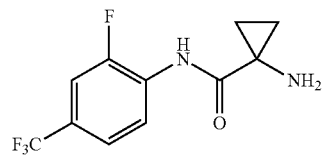 [SMILES: NC1(C(=O)Nc2ccc(C(F)(F)F)cc2F)CC1]

A title compound (white powders, 46 mg, 99%) was obtained in the same manner as in Reference Example 1-2, by using benzyl 1-((2-fluoro-4-(trifluoromethyl)phenyl)carbamoyl)cyclopropyl)carbamate (70 mg, 0.18 mmol) synthesized in Reference Example 3-1.

1H NMR (DMSO-d$_{6}$, 400 MHz): δ=1.02 (dd, 2H, J=4, 7 Hz), 1.26 (dd, 2H, J=4, 7 Hz), 7.59 (d, 1H, J=9 Hz), 7.79 (dd, 1H, J=2, 11 Hz), 8.45 (t, 1H, J=8 Hz). 3H cannot be observed.

Reference Example 4

1-Amino-N-(5-(trifluoromethyl)pyridin-3-yl) cyclopropane-1-carboxamide

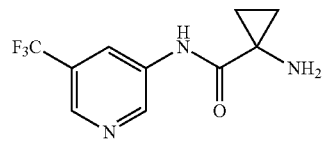 [SMILES: NC1(C(=O)Nc2cncc(C(F)(F)F)c2)CC1]

1-(((Benzyloxy)carbonyl)amino) cyclopropane-1-carboxylic acid (50 mg, 0.21 mmol), 5-(trifluoromethyl)pyridin-3-amine (104 mg, 0.64 mmol), and DIPEA (111 μL, 0.64 mmol) were dissolved in DMF (1 mL), and then HATU (97 mg, 0.26 mmol) was added thereto, followed by stirring at room temperature overnight. A saturated aqueous sodium hydrogen carbonate solution was added to a reaction liquid, the mixture was stirred for a while, and then extraction was performed with ethyl acetate. A separated organic layer was washed with a saturated saline solution and dried over anhydrous sodium sulfate, an insoluble substance was filtered, and then a solvent was distilled off under reduced pressure. The obtained residue was purified by silica gel column chromatography (hexane:ethyl acetate) (concentration gradient: 40% to 60%) to obtain a crude product (white powders, 126 mg) of benzyl (1-((5-(trifluoromethyl)pyridin-3-yl)carbamoyl)cyclopropyl)carbamate.

The obtained crude product (126 mg) was dissolved in methanol (2 mL), and then 10% palladium-carbon (12.6 mg) was added thereto, followed by stirring at room temperature for one hour under a hydrogen atmosphere. A reaction liquid was filtered through celite, and then a solvent was distilled off under reduced pressure. The obtained residue was purified by silica gel column chromatography (hexane: ethyl acetate) (concentration gradient: 50% to 80%) to obtain a title compound (white powders, 20 mg, 38%).

1H NMR (CD$_3$OD, 400 MHz): δ=1.03 (dd, 2H, J=4, 7 Hz), 1.39 (dd, 2H, J=4, 7 Hz), 8.5-8.6 (m, 2H), 9.00 (d, 1H, J=2 Hz). 3H cannot be observed.

Reference Example 5

2-Amino-N-isopropyl-N-(6-(trifluoromethyl)pyridin-3-yl)acetamide

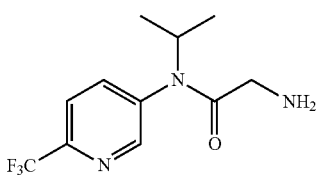 [SMILES: CC(C)N(C(=O)CN)c1ccc(C(F)(F)F)nc1]

N-Isopropyl-6-(trifluoromethyl)pyridin-3-amine (102 mg, 0.50 mmol) and pyridine (200 µL, 2.50 mmol) were dissolved in THF (4 mL) and then benzyl (2-chloro-2-oxoethyl)carbamate (0.19 M, 13.5 ml, 2.50 mmol) dissolved in THF was added thereto. After stirring at room temperature for one hour, DMAP (6.7 mg, 0.06 mmol) was added thereto, followed by stirring overnight. Water was added to a reaction liquid and then extraction was performed with ethyl acetate. A separated organic layer was washed with a saturated aqueous sodium hydrogen carbonate solution and dried over anhydrous sodium sulfate, then an insoluble substance was filtered, and a solvent was distilled off under reduced pressure. The obtained residue was purified by silica gel column chromatography (hexane:ethyl acetate) (concentration gradient: 40% to 60%) to obtain a crude product (colorless oil, 82 mg) of benzyl (2-(isopropyl(6-(trifluoromethyl)pyridin-3-yl)amino)-2-oxoethyl)carbamate.

The obtained crude product (82 mg) was dissolved in methanol (3 mL), and then 10% palladium-carbon (8.2 mg) was added thereto, followed by stirring at room temperature for 16 hours under a hydrogen atmosphere. A reaction liquid was filtered through celite, and then a solvent was distilled off under reduced pressure. The obtained residue was purified by silica gel column chromatography (ethyl acetate: methanol) (concentration gradient: 25% to 50%) to obtain a title compound (colorless oil, 49 mg, 37%).

1H NMR (CD$_3$OD, 400 MHz): δ=1.10 (d, 6H, J=6 Hz), 2.93 (brs, 2H), 4.62 (brs, 1H), 7.9-8.0 (m, 2H), 8.62 (s, 1H). 2H cannot be observed.

Reference Example 6 tert-Butyl (5-oxo-1-(6-(trifluoromethyl)pyridin-3-yl)pyrrolidin-3-yl)carbamate

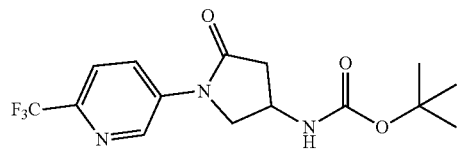 [SMILES: CC(C)(C)OC(=O)NC1CC(=O)N(c2ccc(C(F)(F)F)nc2)C1]

tert-Butyl (5-oxopyrrolidin-3-yl)carbamate (60 mg, 0.30 mmol), 5-bromo-2-(trifluoromethyl)pyridine (81 mg, 0.36 mmol), tris(dibenzylideneacetone)dipalladium(0) (28 mg, 0.03 mmol), BINAP (41 mg, 0.07 mmol), and potassium tert-butoxide (58 mg, 0.60 mmol) were dissolved in toluene (1.5 mL), followed by stirring at 85° C. overnight under a nitrogen atmosphere. A saturated aqueous sodium hydrogen carbonate solution was added to a reaction liquid, and then extraction was performed with ethyl acetate. A separated organic layer was dried over anhydrous sodium sulfate, an insoluble substance was filtered, and then a solvent was distilled off under reduced pressure. The obtained residue was purified by silica gel column chromatography (hexane: ethyl acetate) (concentration gradient: 31% to 50%) to obtain a title compound (yellow powders, 9 mg, 8%).

1H NMR (CDCl$_3$, 400 MHz): δ=1.46 (s, 9H), 2.56 (dd, 1H, J=5, 17 Hz), 3.02 (dd, 1H, J=8, 17 Hz), 3.82 (dd, 1H, J=4, 10 Hz), 4.23 (dd, 1H, J=6, 10 Hz), 4.49 (brs, 1H), 4.86 (brs, 1H), 7.70 (d, 1H, J=9 Hz), 8.41 (dd, 1H, J=2, 9 Hz), 8.82 (brs, 1H).

Reference Example 7-1

(1R, 2S, 5R)-2-Isopropyl-5-methylcyclohexyl (1S, 2S)-2-(1H-benzo[d]imidazol-2-yl) cyclopropane-1-carboxylate

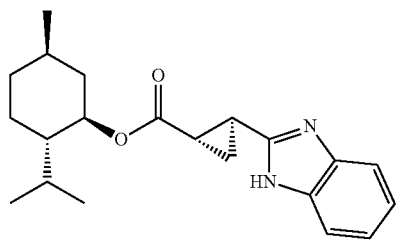 [SMILES: CC(C)[C@@H]1CC[C@@H](C)C[C@H]1OC(=O)[C@H]1C[C@@H]1c1nc2ccccc2[nH]1]

(1S, 2S)-2-((((1R, 2S, 5R)-2-Isopropyl-5-methylcyclohexyl)oxy)carbonyl) cyclopropane-1-carboxylic acid (9.51 g, 35.4 mmol), 1,2-phenylenediamine (4.60 g, 42.5 mmol), and DIPEA (30.6 mL, 177.6 mmol) were added into a 200 mL round-bottom flask, the resultant was suspended in DMF (119 mL), and then HATU (17.5 g, 46.0 mmol) was added thereto, followed by stirring at room temperature for 23 hours. A saturated aqueous sodium hydrogen carbonate solution was added to a reaction liquid, and then extraction was performed four times with ethyl acetate. A collected organic layer was dried over sodium sulfate, an insoluble substance was filtered, and then filtrate was concentrated under reduced pressure. After adding toluene to the obtained residue and azeotroping water, acetic acid (62 mL) was added thereto, followed by stirring at 80° C. for three hours. After distilling off acetic acid under reduced pressure, an aqueous potassium carbonate solution was added to the obtained residue to perform neutralization, and extraction was performed three times with ethyl acetate. A collected organic layer was dried over sodium sulfate, an insoluble substance was filtered, and then filtrate was concentrated under reduced pressure. The obtained residue was subjected to origin removal by silica gel and hexane:ethyl acetate of 1:1 and similarly a solid was precipitated using hexane:ethyl acetate of 1:1. The obtained solid was collected by filtration to obtain a title compound (8.34 g, 70%).

$^1$H NMR (CD$_3$OD, 400 MHz): δ=0.80 (d, 3H, J=7 Hz), 0.8-1.6 (m, 11H), 1.6-1.8 (m, 4H), 1.8-2.0 (m, 2H), 2.2-2.3 (m, 1H), 2.6-2.7 (m, 1H), 4.74 (dt, 1H, J=4, 10 Hz), 7.1-7.3 (m, 2H), 7.4-7.6 (m, 2H). 1H was not observed.

Reference Example 7-2

(1S, 2S)-2-(1H-Benzo[d]imidazol-2-yl) cyclopropane-1-carboxylic acid

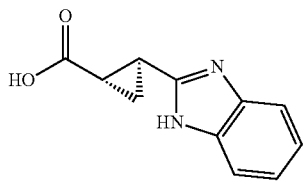 [SMILES: O=C(O)[C@H]1C[C@@H]1c1nc2ccccc2[nH]1]

(1R, 2S, 5R)-2-Isopropyl-5-methylcyclohexyl (1S, 2S)-2-(1H-benzo[d]imidazol-2-yl) cyclopropane-1-carboxylate (7.34 g, 21.6 mmol) synthesized in Reference Example 7-1 was added into a 200 mL round-bottom flask, the resultant was suspended in isopropanol (58 mL) and water (4.6 mL), and then sodium hydroxide (1.72 g, 43.0 mmol) was added thereto, followed by stirring at 80° C. overnight. After distilling off a solvent under reduced pressure, water was added to the obtained residue, and the resultant was washed twice with diethyl ether. An aqueous layer was acidified by adding 3N hydrochloric acid (17 mL), and then the residue obtained by distilling off the solvent was suspended by adding ethyl acetate and water. The obtained solid was collected by filtration and dried at room temperature under reduced pressure to obtain a title compound (light brown powders, 2.44 g, 56%).

$^1$H NMR (DMSO-d$_6$, 400 MHz): δ=1.4-1.7 (m, 2H), 2.0-2.2 (m, 1H), 2.5-2.6 (m, 1H), 7.0-7.2 (m, 2H), 7.3-7.6 (m, 2H), 12.41 (brs, 1H). 1H was not observed.

Reference Example 8-1

(1R, 2S, 5R)-2-Isopropyl-5-methylcyclohexyl (1S, 2S)-2-(1-ethyl-1H-benzo[d]imidazol-2-yl) cyclopropane-1-carboxylate

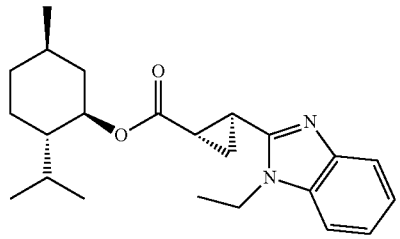 [SMILES: CCn1c([C@H]2C[C@@H]2C(=O)O[C@@H]2C[C@H](C)CC[C@H]2C(C)C)nc2ccccc21]

(1R, 2S, 5R)-2-Isopropyl-5-methylcyclohexyl (1S, 2S)-2-(1H-benzo[d]imidazol-2-yl) cyclopropane-1-carboxylate (400 mg, 1.2 mmol) synthesized in Reference Example 7-1 and cesium carbonate (612 mg, 1.9 mmol) were dissolved in DMF (4 mL), and then bromoethane (154 µL, 1.4 mmol) was added thereto, followed by stirring at room temperature for one day. A saturated aqueous ammonium chloride solution and water were added to a reaction liquid, and then extraction was performed with ethyl acetate. A separated organic layer was washed with a saturated saline solution and dried over anhydrous sodium sulfate, an insoluble substance was filtered, and then a solvent was distilled off under reduced pressure. The obtained residue was purified by silica gel column chromatography (hexane:ethyl acetate) (concentration gradient: 5% to 40%) to obtain a title compound (colorless oily substance, 451 mg, 104%).

$^1$H NMR (CDCl$_3$, 400 MHz): δ=0.80 (d, 3H, J=7 Hz), 0.8-1.2 (m, 9H), 1.4-1.6 (m, 2H), 1.45 (t, 3H, J=7 Hz), 1.6-1.8 (m, 3H), 1.8-2.1 (m, 3H), 2.3-2.4 (m, 1H), 2.5-2.7 (m, 1H), 4.29 (q, 2H, J=7 Hz), 4.74 (dt, 1H, J=4, 11 Hz), 7.2-7.4 (m, 3H), 7.6-7.7 (m, 1H).

Reference Example 8-2

(1S, 2S)-2-(1-Ethyl-1H-benzo[d]imidazol-2-yl) cyclopropane-1-carboxylic acid

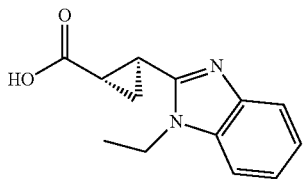 [SMILES: CCn1c([C@H]2C[C@@H]2C(=O)O)nc2ccccc21]

A title compound (white powders, 433 mg) was obtained in the same manner as in Reference Example 7-2, by using (1R, 2S, 5R)-2-isopropyl-5-methylcyclohexyl (1S, 2S)-2-(1-ethyl-1H-benzo[d]imidazol-2-yl) cyclopropane-1-carboxylate (451 mg) synthesized in Reference Example 8-1.

$^1$H NMR (DMSO-d$_6$, 400 MHz): δ=1.42 (t, 3H, J=7 Hz), 1.7-1.8 (m, 1H), 2.0-2.1 (m, 1H), 2.5-2.7 (m, 1H), 2.9-3.0 (m, 1H), 4.5-4.7 (m, 2H), 7.5-7.6 (m, 2H), 7.7-7.8 (m, 1H), 7.9-8.0 (m, 1H), 12.94 (brs, 1H).

Reference Example 9-1

(1R, 2S, 5R)-2-Isopropyl-5-methylcyclohexyl (1S, 2S)-2-(5-chloro-1H-benzo[d]imidazol-2-yl) cyclopropane-1-carboxylate

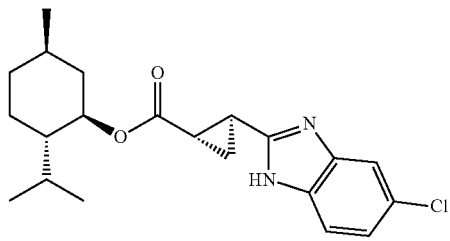 [SMILES: CC(C)[C@@H]1CC[C@@H](C)C[C@H]1OC(=O)[C@H]1C[C@@H]1c1nc2cc(Cl)ccc2[nH]1]

A title compound (light yellow crystals, 890 mg, 77%) was obtained in the same manner as in Reference Example 7-1, by using (1S, 2S)-2-((((1R, 2S, 5R)-2-isopropyl-5-methylcyclohexyl)oxy)carbonyl) cyclopropane-1-carboxylic acid (830 mg, 3.1 mmol) and 4-chloro-1,2-phenylenediamine (529 mg, 3.7 mmol).

1H NMR (DMSO-$d_6$, 400 MHz): δ=0.75 (d, 3H, J=7 Hz), 0.8-1.2 (m, 9H), 1.2-1.3 (m, 1H), 1.3-1.7 (m, 6H), 1.7-2.0 (m, 1H), 2.1-2.3 (m, 1H), 2.5-2.6 (m, 1H), 4.64 (dt, 1H, J=4, 11 Hz), 7.15 (dd, 1H, J=2, 8 Hz), 7.46 (d, 1H, J=8 Hz), 7.52 (d, 1H, J=2 Hz). 1H cannot be observed.

Reference Example 9-2

(1S, 2S)-2-(5-Chloro-1H-benzo[d]imidazol-2-yl) cyclopropane-1-carboxylic acid

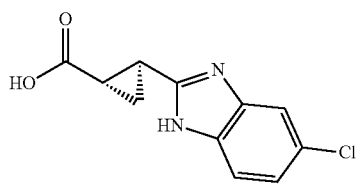 [SMILES: O=C(O)[C@H]1C[C@@H]1c1nc2cc(Cl)ccc2[nH]1]

A title compound (white crystals, 225 mg, 40%) was obtained in the same manner as in Reference Example 7-2, by using (1R, 2S, 5R)-2-isopropyl-5-methylcyclohexyl (1S, 2S)-2-(5-chloro-1H-benzo[d]imidazol-2-yl) cyclopropane-1-carboxylate (890 mg, 2.4 mmol) synthesized in Reference Example 9-1.

1H NMR (DMSO-$d_6$, 400 MHz): δ=1.5-1.7 (m, 2H), 2.1-2.2 (m, 1H), 2.5-2.6 (m, 1H), 7.15 (dd, 1H, J=2, 8 Hz), 7.46 (d, 1H, J=8 Hz), 7.52 (s, 1H), 12.61 (brs, 2H).

Reference Example 10-1

(1R, 2S, 5R)-2-Isopropyl-5-methylcyclohexyl (1S, 2S)-2-(1-cyclopropyl-1H-benzo[d]imidazol-2-yl) cyclopropane-1-carboxylate

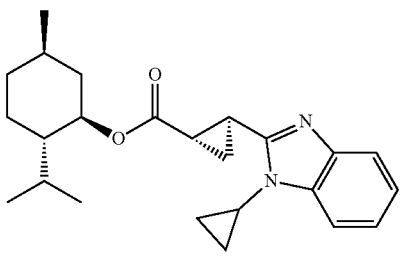 [SMILES: CC(C)[C@@H]1CC[C@@H](C)C[C@H]1OC(=O)[C@H]1C[C@@H]1c1nc2ccccc2n1C1CC1]

(1R, 2S, 5R)-2-Isopropyl-5-methylcyclohexyl (1S, 2S)-2-(1H-benzo[d]imidazol-2-yl) cyclopropane-1-carboxylate (408 mg, 1.1 mmol) synthesized in Reference Example 7-1, cyclopropylboronic acid (184 mg, 2.1 mmol), and sodium carbonate (227 mg, 2.1 mmol) were dissolved in toluene (4 mL), and then copper(II) acetate monohydrate (214 mg, 1.1 mmol) suspended in toluene (7 nil) and 2,2'-bipyridyl (167 mg, 1.1 mmol) was added thereto, followed by stirring at 70° C. overnight. A saturated aqueous ammonium chloride solution and water were added to a reaction liquid, and then extraction was performed with ethyl acetate. A separated organic layer was washed with a saturated saline solution and dried over anhydrous sodium sulfate, an insoluble substance was filtered, and then a solvent was distilled off under reduced pressure. The obtained residue was purified by silica gel column chromatography (hexane:ethyl acetate) (concentration gradient: 10% to 25%) to obtain a title compound (colorless oily substance, 270 mg, 66%).

$^1$H NMR (CDCl$_3$, 400 MHz): δ=0.80 (d, 3H, J=7 Hz), 0.9-1.5 (m, 15H), 1.6-2.1 (m, 6H), 2.32 (ddd, 1H, J=4, 6, 9 Hz), 2.87 (ddd, 1H, J=4, 6, 9 Hz), 3.30 (ddd, 1H, J=4, 7, 11 Hz), 4.73 (td, 1H, J=4, 11 Hz), 7.2-7.3 (m, 2H), 7.4-7.7 (m, 2H).

Reference Example 10-2

(1S, 2S)-2-(1-Cyclopropyl-1H-benzo[d]imidazol-2-yl) cyclopropane-1-carboxylic acid

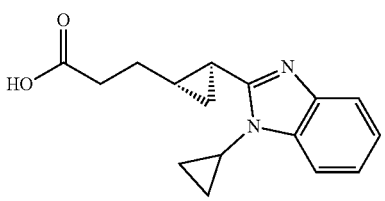 [SMILES: O=C(O)CC[C@H]1C[C@@H]1c1nc2ccccc2n1C1CC1]

A title compound (white powders, 209 mg) was obtained in the same manner as in Reference Example 7-2, by using (1R, 2S, 5R)-2-isopropyl-5-methylcyclohexyl (1S, 2S)-2-(1-cyclopropyl-1H-benzo[d]imidazol-2-ye cyclopropane-1-carboxylate (270 mg) synthesized in Reference Example 10-1.

$^1$H NMR (DMSO-$d_6$, 400 MHz): δ=1.1-1.4 (m, 4H), 1.71 (quint, 1H, J=5 Hz), 1.8-1.9 (m, 1H), 2.3-2.5 (m, 1H), 2.93

(ddd, 1H, J=4, 6, 9 Hz), 3.5-3.7 (m, 1H), 7.44 (quint, J=2H, 8 Hz), 7.67 (d, 1H, J=8 Hz), 7.77 (d, 1H, J=8 Hz). 1H cannot be observed.

Reference Example 11 tert-Butyl (1-((2-fluoro-3-(trifluoromethyl)phenyl)carbamoyl)cyclopropyl)carbamate

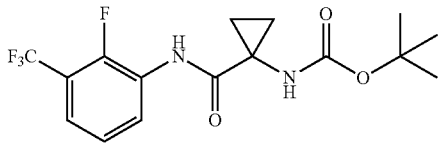 [SMILES: CC(C)(C)OC(=O)NC1(C(=O)Nc2cccc(C(F)(F)F)c2F)CC1]

A title compound (light yellow oil, 12 mg, 13%) was obtained in the same manner as in Reference Example 1-1, by using 2-fluoro-3-(trifluoromethyl)aniline (45 mg, 0.25 mmol) and 1-((tert-butoxycarbonyl)amino) cyclopropane-1-carboxylic acid (101 mg, 0.50 mmol).

1H NMR (CDCl$_3$, 400 MHz): δ=1.16 (dd, 2H, J=5, 8 Hz), 1.50 (s, 9H), 1.70 (dd, 2H, J=5, 8 Hz), 5.14 (s, 1H), 7.1-7.4 (m, 2H), 8.5-8.6 (m, 1H), 8.82 (s, 1H).

Reference Example 12 tert-Butyl (1-((3-fluoro-5-(trifluoromethyl)phenyl)carbamoyl)cyclopropyl)carbamate

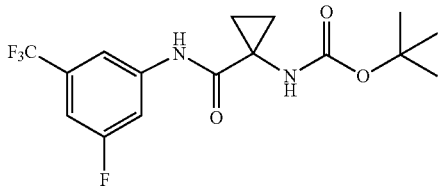 [SMILES: CC(C)(C)OC(=O)NC1(C(=O)Nc2cc(F)cc(C(F)(F)F)c2)CC1]

A title compound (white powders, 25 mg, 27%) was obtained in the same manner as in Reference Example 1-1, by using 3-fluoro-5-(trifluoromethyl)aniline (45 mg, 0.25 mmol) and 1-((tert-butoxycarbonyl)amino) cyclopropane-1-carboxylic acid (101 mg, 0.50 mmol).

1H NMR (CDCl$_3$, 400 MHz): δ=1.13 (dd, 2H, J=5, 8 Hz), 1.50 (s, 9H), 1.67 (dd, 2H, J=5, 8 Hz), 5.11 (s, 1H), 7.06 (d, 1H, J=8 Hz), 7.46 (s, 1H), 7.6-7.7 (m, 1H), 8.81 (s, 1H).

Example 1

Trans-2-(1H-benzo[d]imidazol-2-yl)-N-(1-oxo-1-((4-propylphenyl)amino)propan-2-yl) cyclopropane-1-carboxamide

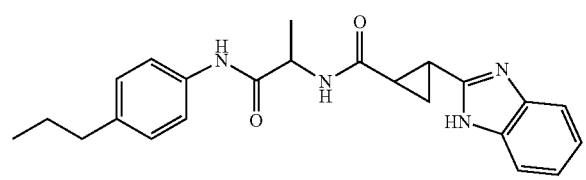 [SMILES: CCCc1ccc(NC(=O)C(C)NC(=O)C2CC2c2nc3ccccc3[nH]2)cc1]

Trans-(2-(1H-benzo[d]imidazol-2-yl) cyclopropane-1-carbonyl)-D-alanine (14 mg, 0.05 mmol) synthesized in Reference Example 1-2 and 4-propylaniline (17 µL, 0.10 mmol) were dissolved in DMF (500 µL), and then DIPEA (17 µL, 0.10 mmol) and HATU (23 mg, 0.06 mmol) were added thereto, followed by stirring at room temperature for four hours. A saturated aqueous sodium hydrogen carbonate solution was added to a reaction liquid, the mixture was stirred for a while, and then extraction was performed with chloroform. A separated organic layer was dried over anhydrous sodium sulfate, an insoluble substance was filtered, and then a solvent was distilled off under reduced pressure. The obtained residue was purified by PLC (chloroform/methanol=25/2) to obtain Diastereomer A (upper spot on TLC (chloroform/methanol=10/1), white powders, 11 mg, 55%) and Diastereomer B (lower spot on TLC (chloroform/methanol=10/1), white powders, 4 mg, 20%) of a title compound.

Diastereomer A $^1$H NMR (DMSO-d$_6$, 400 MHz): δ=0.87 (t, 3H, J=7 Hz), 1.29 (d, 3H, J=7 Hz), 1.3-1.7 (m, 4H), 2.3-2.6 (m, 4H), 4.45 (quint, 1H, J=7 Hz), 7.0-7.2 (m, 4H), 7.3-7.6 (m, 4H), 8.65 (d, 1H, J=7 Hz), 9.99 (s, 1H), 12.38 (s, 1H).

MS: 391.26 [M+H]$^+$

Diastereomer B $^1$H NMR (DMSO-d$_6$, 400 MHz): δ=0.86 (t, 3H, J=7 Hz), 1.30 (d, 3H, J=7 Hz), 1.3-1.6 (m, 4H), 2.3-2.6 (m, 4H), 4.46 (quint, 1H, J=7 Hz), 7.0-7.2 (m, 2H), 7.11 (d, 2H, J=8 Hz), 7.3-7.6 (m, 2H), 7.49 (d, 2H, J=8 Hz), 8.67 (d, 1H, J=7 Hz), 10.00 (s, 1H), 12.40 (s, 1H).

MS: 391.23 [M+H]$^+$

Example 2

Trans-2-(1H-benzo[d]imidazol-2-yl)-N-(1-oxo-1-((4-propylphenyl)amino)propan-2-yl) cyclopropane-1-carboxamide

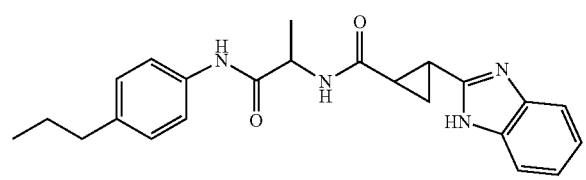 [SMILES: CCCc1ccc(NC(=O)C(C)NC(=O)C2CC2c2nc3ccccc3[nH]2)cc1]

Diastereomer A (upper spot on TLC (chloroform/methanol=10/1), white powders, 7 mg, 4%) and Diastereomer B (lower spot on TLC (chloroform/methanol=10/1), white powders, 14 mg, 7%) of a title compound were obtained in the same manner as in Example 1, by using trans-(2-(1H-benzo[d]imidazol-2-yl) cyclopropane-1-carbonyl)-D-alanine (137 mg, 0.50 mmol) synthesized in Reference Example 2 and 4-propylaniline (169 µL, 1.0 mmol).

Diastereomer A $^1$H NMR (DMSO-d$_6$, 400 MHz): δ=0.87 (t, 3H, J=7 Hz), 1.29 (d, 3H, J=7 Hz), 1.3-1.7 (m, 4H), 2.3-2.6 (m, 4H), 4.45 (quint, 1H, J=7 Hz), 7.0-7.2 (m, 2H), 7.12 (d, 2H, J=9 Hz), 7.3-7.6 (m, 2H), 7.51 (d, 2H, J=9 Hz), 8.65 (d, 1H, J=7 Hz), 9.99 (s, 1H), 12.39 (s, 1H).

MS: 391.24 [M+H]$^+$

Diastereomer B $^1$H NMR (DMSO-d$_6$, 400 MHz): δ=0.86 (t, 3H, J=7 Hz), 1.30 (d, 3H, J=7 Hz), 1.3-1.6 (m, 4H), 2.3-2.6 (m, 4H), 4.4-4.5 (m, 1H), 7.0-7.2 (m, 2H), 7.11 (d, 2H, J=8 Hz), 7.3-7.6 (m, 2H), 7.49 (d, 2H, J=8 Hz), 8.67 (d, 1H, J=7 Hz), 10.00 (s, 1H), 12.40 (s, 1H).

MS: 391.24 [M+H]+

Example 3

Trans-2-(1H-benzo[d]imidazol-2-yl)-N-(1-((4-isopropoxyphenyl)amino)-1-oxopropan-2-yl) cyclopropane-1-carboxamide

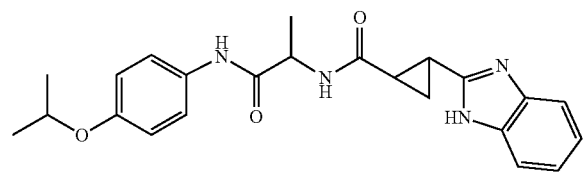 [SMILES: CC(C)Oc1ccc(NC(=O)C(C)NC(=O)C2CC2c2nc3ccccc3[nH]2)cc1]

A title compound (white powders, 11 mg, 52%) was obtained in the same manner as in Example 1, by using trans-(2-(1H-benzo[d]imidazol-2-yl) cyclopropane-1-carbonyl)-D-alanine (14 mg, 0.05 mmol) synthesized in Reference Example 1-2 and 4-isopropoxyaniline (15 µL, 0.10 mmol).

$^1$H NMR (DMSO-d$_6$, 400 MHz): δ=1.27 (d, 6H, J=6 Hz), 1.32 (d, 3H, J=7 Hz), 1.4-1.6 (m, 2H), 2.3-2.5 (m, 2H), 4.4-4.6 (m, 2H), 6.89 (d, 2H, J=9 Hz), 7.1-7.2 (m, 2H), 7.4-7.6 (m, 4H), 8.67 (d, 1H, J=7 Hz), 9.95 (s, 1H). 1H cannot be observed.

MS: 407.23 [M+H]+

Example 4

Trans-2-(1H-benzo[d]imidazol-2-yl)-N-(1-oxo-1-((4-(trifluoromethyl)phenyl)amino)propan-2-yl) cyclopropane-1-carboxamide

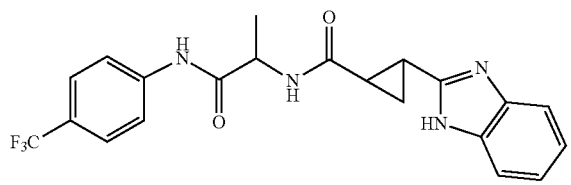 [SMILES: CC(NC(=O)C1CC1c1nc2ccccc2[nH]1)C(=O)Nc1ccc(C(F)(F)F)cc1]

Diastereomer A (upper spot on TLC (chloroform/methanol=10/1), white powders, 37 mg, 9%) and Diastereomer B (lower spot on TLC (chloroform/methanol=10/1), white powders, 44 mg, 11%) of a title compound were obtained in the same manner as in Example 1, by using trans-(2-(1H-benzo[d]imidazol-2-yl) cyclopropane-1-carbonyl)-D-alanine (273 mg, 1.0 mmol) synthesized in Reference Example 1-2 and 4-(trifluoromethyl)aniline (251 µL, 2.0 mmol).

Diastereomer A $^1$H NMR (DMSO-d$_6$, 400 MHz): δ=1.3-1.6 (m, 2H), 1.32 (d, 3H, J=7 Hz), 2.3-2.5 (m, 2H), 4.46 (quint, 1H, J=7 Hz), 7.0-7.2 (m, 2H), 7.3-7.6 (m, 2H), 7.68 (d, 2H, J=9 Hz), 7.83 (d, 2H, J=9 Hz), 8.73 (d, 1H, J=7 Hz), 10.46 (s, 1H), 12.38 (s, 1H).

MS: 417.19 [M+H]+

Diastereomer B $^1$H NMR (DMSO-d$_6$, 400 MHz): δ=1.3-1.6 (m, 2H), 1.32 (d, 3H, J=7 Hz), 2.3-2.5 (m, 2H), 4.47 (quint, 1H, J=8 Hz), 7.0-7.2 (m, 2H), 7.3-7.6 (m, 2H), 7.68 (d, 2H, J=9 Hz), 7.81 (d, 2H, J=9 Hz), 8.74 (d, 1H, J=7 Hz), 10.47 (s, 1H), 12.41 (s, 1H).

MS: 417.18 [M+H]+

Example 5

Trans-2-(1H-benzo[d]imidazol-2-yl)-N-(1-oxo-1-((6-(trifluoromethyl)pyridin-3-yl)amino)propan-2-yl) cyclopropane-1-carboxamide

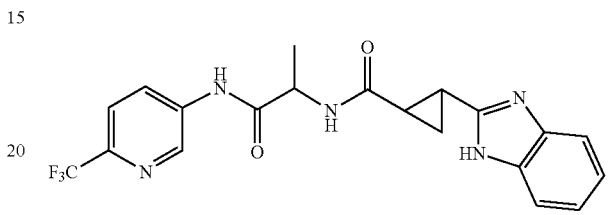

Diastereomer A (upper spot on TLC (ethyl acetate/methanol=100/3), white powders, 4 mg, 5%) and Diastereomer B (lower spot on TLC (ethyl acetate/methanol=100/3), white powders, 6 mg, 7%) of a title compound were obtained in the same manner as in Example 1, by using trans-(2-(1H-benzo[d]imidazol-2-yl) cyclopropane-1-carbonyl)-D-alanine (55 mg, 0.20 mmol) synthesized in Reference Example 1-2 and 6-(trifluoromethyl)pyridin-3-amine (322 mg, 2.0 mmol).

Diastereomer A $^1$H NMR (DMSO-d$_6$, 400 MHz): δ=1.3-1.6 (m, 2H), 1.34 (d, 3H, J=7 Hz), 2.3-2.5 (m, 2H), 4.47 (quint, 1H, J=7 Hz), 7.0-7.2 (m, 2H), 7.3-7.6 (m, 2H), 7.88 (d, 1H, J=9 Hz), 8.35 (dd, 1H, J=2, 9 Hz), 8.79 (d, 1H, J=7 Hz), 8.91 (d, 1H, J=2 Hz), 10.76 (s, 1H), 12.40 (s, 1H).

MS: 418.17 [M+H]+

Diastereomer B $^1$H NMR (DMSO-d$_6$, 400 MHz): δ=1.3-1.5 (m, 2H), 1.35 (d, 3H, J=7 Hz), 2.3-2.5 (m, 2H), 4.4-4.6 (m, 1H), 7.0-7.2 (m, 2H), 7.3-7.5 (m, 2H), 7.87 (d, 1H, J=9 Hz), 8.2-8.4 (m, 1H), 8.82 (d, 1H, J=7 Hz), 8.89 (d, 1H, J=2 Hz), 10.75 (s, 1H), 12.38 (s, 1H).

MS: 418.18 [M+H]+

Example 6

Trans-2-(1H-benzo[d]imidazol-2-yl)-N-(1-((4-cyanophenyl)amino)-1-oxopropan-2-yl) cyclopropane-1-carboxamide

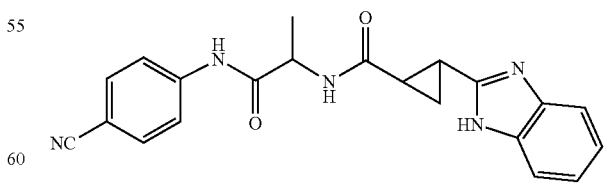

Diastereomer A (upper spot on TLC (ethyl acetate/methanol=40/1), white powders, 2 mg, 5%) and Diastereomer B (lower spot on TLC (ethyl acetate/methanol=40/1), white powders, 3 mg, 8%) of a title compound were obtained in the same manner as in Example 1, by using trans-(2-(1H-benzo

[d]imidazol-2-yl) cyclopropane-1-carbonyl)-D-alanine (27 mg, 0.10 mmol) synthesized in Reference Example 1-2 and 4-aminobenzonitrile (24 mg, 0.20 mmol).

Diastereomer A $^1$H NMR (DMSO-d$_6$, 400 MHz): δ=1.3-1.6 (m, 2H), 1.31 (d, 3H, J=7 Hz), 2.3-2.5 (m, 2H), 4.45 (quint, 1H, J=7 Hz), 7.0-7.2 (m, 2H), 7.3-7.6 (m, 2H), 7.7-7.9 (m, 4H), 8.78 (d, 1H, J=7 Hz), 10.58 (s, 1H), 12.40 (s, 1H).

MS: 374.18 [M+H]$^+$

Diastereomer B $^1$H NMR (DMSO-d$_6$, 400 MHz): δ=1.3-1.5 (m, 2H), 1.32 (d, 3H, J=7 Hz), 2.3-2.5 (m, 2H), 4.46 (quint, 1H, J=7 Hz), 7.0-7.2 (m, 2H), 7.3-7.6 (m, 2H), 7.7-7.9 (m, 4H), 8.79 (d, 1H, J=7 Hz), 10.59 (s, 1H), 12.42 (s, 1H).

MS: 374.18 [M+H]$^+$

Example 7

Trans-2-(1H-benzo[d]imidazol-2-yl)-N-(1-((4-(tert-butyl)phenyl)amino)-1-oxopropan-2-yl) cyclopropane-1-carboxamide

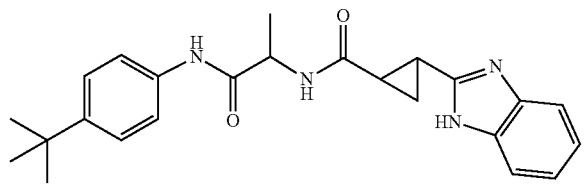 [SMILES: CC(NC(=O)C1CC1c1nc2ccccc2[nH]1)C(=O)Nc1ccc(C(C)(C)C)cc1]

Diastereomer A (upper spot on TLC (ethyl acetate/methanol=100/1), white powders, 28 mg, 70%) and Diastereomer B (lower spot on TLC (ethyl acetate/methanol=100/1), white powders, 8 mg, 20%) of a title compound were obtained in the same manner as in Example 1, by using trans-(2-(1H-benzo[d]imidazol-2-yl) cyclopropane-1-carbonyl)-D-alanine (27 mg, 0.10 mmol) synthesized in Reference Example 1-2 and 4-(tert-butyl)aniline (19 μL, 0.20 mmol).

Diastereomer A $^1$H NMR (DMSO-d$_6$, 400 MHz): δ=1.26 (s, 9H), 1.29 (d, 3H, J=7 Hz), 1.3-1.6 (m, 2H), 2.3-2.5 (m, 2H), 4.46 (quint, 1H, J=7 Hz), 7.0-7.2 (m, 2H), 7.3-7.5 (m, 2H), 7.32 (d, 2H, J=8 Hz), 7.52 (d, 2H, J=8 Hz), 8.64 (d, 1H, J=7 Hz), 9.99 (s, 1H), 12.38 (s, 1H).

MS: 405.25 [M+H]$^+$

Diastereomer B $^1$H NMR (DMSO-d$_6$, 400 MHz): δ=1.25 (s, 9H), 1.30 (d, 3H, J=7 Hz), 1.3-1.6 (m, 2H), 2.3-2.5 (m, 2H), 4.4-4.6 (m, 1H), 7.0-7.2 (m, 2H), 7.3-7.5 (m, 2H), 7.31 (d, 2H, J=8 Hz), 7.50 (d, 2H, J=8 Hz), 8.67 (d, 1H, J=7 Hz), 10.01 (s, 1H), 12.42 (s, 1H).

MS: 405.25 [M+H]$^+$

Example 8

Trans-2-(1H-benzo[d]imidazol-2-yl)-N-(1-(methyl (4-(trifluoromethyl)phenyl)amino)-1-oxopropan-2-yl) cyclopropane-1-carboxamide

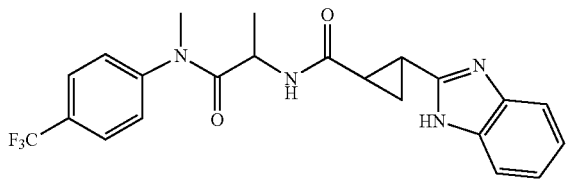 [SMILES: CC(NC(=O)C1CC1c1nc2ccccc2[nH]1)C(=O)N(C)c1ccc(C(F)(F)F)cc1]

Diastereomer A (upper spot on TLC (ethyl acetate/methanol=100/1), white powders, 8 mg, 12%) and Diastereomer B (lower spot on TLC (ethyl acetate/methanol=100/1), white powders, 8 mg, 12%) of a title compound were obtained in the same manner as in Example 1, by using trans-(2-(1H-benzo[d]imidazol-2-yl) cyclopropane-1-carbonyl)-D-alanine (41 mg, 0.15 mmol) synthesized in Reference Example 1-2 and N-methyl-4-(trifluoromethyl)aniline (26 mg, 0.15 mmol).

Diastereomer A $^1$H NMR (DMSO-d$_6$, 400 MHz): δ=1.0-1.6 (m, 5H), 2.2-2.6 (m, 2H), 3.1-3.5 (m, 3H), 4.1-4.5 (m, 1H), 7.0-7.2 (m, 2H), 7.3-8.0 (m, 6H), 8.6-8.8 (m, 1H), 12.40 (s, 1H).

MS: 431.18 [M+H]+

Diastereomer B $^1$H NMR (DMSO-d$_6$, 400 MHz): δ=1.0-1.6 (m, 5H), 2.1-3.5 (m, 5H), 3.9-4.5 (m, 1H), 7.0-7.2 (m, 2H), 7.3-8.0 (m, 6H), 8.5-8.7 (m, 1H), 12.2-12.4 (m, 1H).

MS: 431.18 [M+H]$^+$

Example 9

Trans-2-(1H-benzo[d]imidazol-2-yl)-N-(1-((4-(methylsulfonyl)benzyl)amino)-1-oxopropan-2-yl) cyclopropane-1-carboxamide

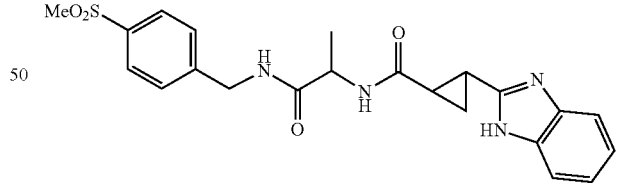

A title compound (white powders, 18 mg, 41%) was obtained in the same manner as in Example 1, by using trans-(2-(1H-benzo[d]imidazol-2-yl) cyclopropane-1-carbonyl)-D-alanine (27 mg, 0.10 mmol) synthesized in Reference Example 1-2 and (4-(methylsulfonyl)phenyl)methanamine (37 mg, 0.20 mmol).

$^1$H NMR (DMSO-d$_6$, 400 MHz): δ=1.24 (d, 3H, J=7 Hz), 1.3-1.6 (m, 2H), 2.3-2.5 (m, 2H), 3.19 (s, 3H), 4.2-4.4 (m, 3H), 7.0-7.2 (m, 2H), 7.3-7.6 (m, 4H), 7.8-8.0 (m, 2H), 8.5-8.7 (m, 2H), 12.37 (s, 1H).

MS: 441.20 [M+H]$^+$

Example 10 tert-Butyl trans-3-(2-(2-(1H-benzo[d]imidazol-2-yl)cyclopropane-1-carboxamido)propanamido)azetidine-1-carboxylate

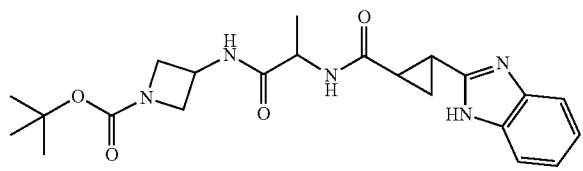 [SMILES: CC(NC(=O)C1CC1c1nc2ccccc2[nH]1)C(=O)NC1CN(C(=O)OC(C)(C)C)C1]

A title compound (white powders, 4 mg, 18%) was obtained in the same manner as in Example 1, by using trans-(2-(1H-benzo[d]imidazol-2-yl) cyclopropane-1-carbonyl)-D-alanine (14 mg, 0.05 mmol) synthesized in Reference Example 1-2 and tut-butyl 3-aminoazetidine-1-carboxylate (17 mg, 0.10 mmol). $^1$H NMR (DMSO-$d_6$, 400 MHz): δ=1.19 (d, 3H, J=7 Hz), 1.3-1.6 (m, 2H), 1.38 (s, 9H), 2.3-2.5 (m, 2H), 3.6-3.8 (m, 2H), 4.0-4.1 (m, 2H), 4.24 (quint, 1H, J=7 Hz), 4.3-4.5 (m, 1H), 7.0-7.2 (m, 2H), 7.3-7.6 (m, 2H), 8.52 (d, 1H, J=7 Hz), 8.60 (d, 1H, J=7 Hz), 12.37 (s, 1H).

MS: 428.26 [M+H]$^+$

Example 11 tert-Butyl trans-4-(2-(2-(1H-benzo[d]imidazol-2-yl)cyclopropane-1-carboxamido)propanamido)piperidine-1-carboxylate

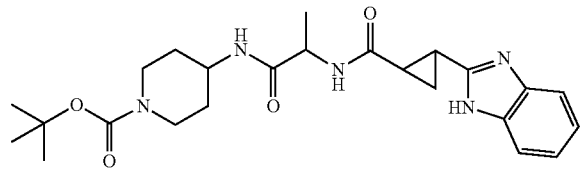 [SMILES: CC(NC(=O)C1CC1c1nc2ccccc2[nH]1)C(=O)NC1CCN(C(=O)OC(C)(C)C)CC1]

A title compound (white powders, 80 mg, 87%) was obtained in the same manner as in Example 1, by using trans-(2-(1H-benzo[d]imidazol-2-yl) cyclopropane-1-carbonyl)-D-alanine (55 mg, 0.20 mmol) synthesized in Reference Example 1-2 and tert-butyl 4-aminopiperidine-1-carboxylate (48 mg, 0.24 mmol).

$^1$H NMR (DMSO-$d_6$, 400 MHz): δ=1.1-1.8 (m, 6H), 1.18 (d, 3H, J=7 Hz), 1.40 (s, 9H), 2.3-2.5 (m, 2H), 2.7-3.0 (m, 2H), 3.5-3.9 (m, 3H), 4.28 (quint, 1H, J=7 Hz), 7.0-7.2 (m, 2H), 7.3-7.6 (m, 2H), 7.91 (d, 1H, J=8 Hz), 8.47 (d, 1H, J=8 Hz), 12.38 (s, 1H).

MS: 456.28 [M+H]+

Example 12

Trans-2-(1H-benzo[d]imidazol-2-yl)-N-(1-oxo-1-(piperidin-4-ylamino)propan-2-yl) cyclopropane-1-carboxamide hydrochloride

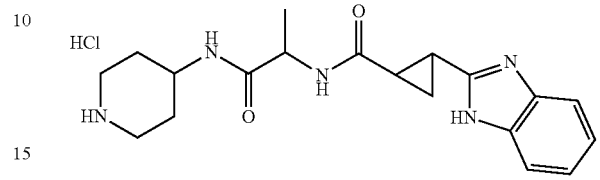

2 M Hydrochloric acid in methanol (10 mL) was added to tert-butyl trans-4-(2-(2-(1H-benzo[d]imidazol-2-yl) cyclopropane-1-carboxamido)propanamido)piperidine-1-carboxylate (75 mg, 0.16 mmol) synthesized in Example 11, followed by stirring at room temperature for 24 hours. A solvent was distilled off under reduced pressure to obtain a title compound (white powders, 64 mg, 98%).

$^1$H NMR (DMSO-$d_6$, 400 MHz): δ=1.20 (d, 3H, J=7 Hz), 1.5-1.7 (m, 3H), 1.8-2.0 (m, 3H), 2.5-2.8 (m, 2H), 2.8-3.0 (m, 2H), 3.2-3.9 (m, 3H), 4.30 (quint, 1H, J=7 Hz), 7.4-7.5 (m, 2H), 7.6-7.8 (m, 2H), 8.20 (d, 1H, J=7 Hz), 8.6-8.8 (m, 3H). 1H cannot be observed.

MS: 356.23 [M+H]$^+$

Example 13

Trans-2-(1H-benzo[d]imidazol-2-yl)-N-(1-oxo-1-((1-propionylpiperidin-4-yl)amino)propan-2-yl)cyclopropane-1-carboxamide

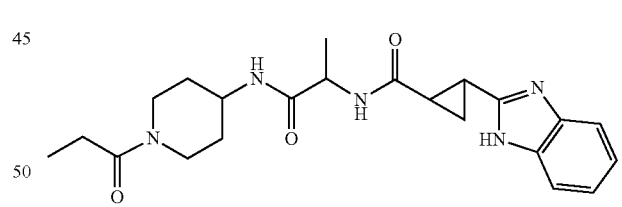

A title compound (white powders, 14 mg, 56%) was obtained in the same manner as in Example 1, by using trans-2-(1H-benzo[d]imidazol-2-yl)-N-(1-oxo-1-(piperidin-4-ylamino)propan-2-yl) cyclopropane-1-carboxamide hydrochloride (24 mg, 0.06 mmol) synthesized in Example 12 and propionic acid (7 μL, 0.09 mmol).

$^1$H NMR (DMSO-$d_6$, 400 MHz): δ=0.97 (t, 3H, J=8 Hz), 1.17 (d, 3H, J=7 Hz), 1.1-1.9 (m, 6H), 2.2-2.5 (m, 4H), 2.6-2.8 (m, 1H), 3.0-3.2 (m, 1H), 3.7-3.9 (m, 2H), 4.1-4.4 (m, 2H), 7.0-7.2 (m, 2H), 7.3-7.6 (m, 2H), 7.91 (d, 1H, J)=8 Hz), 8.47 (d, 1H, J=7 Hz), 12.36 (s, 1H).

MS: 412.25 [M+H]$^+$

Example 14

Trans-2-(1H-benzo[d]imidazol-2-yl)-N-(1-oxo-1-((4-(trifluoromethyl)benzyl)amino)propan-2-yl) cyclopropane-1-carboxamide

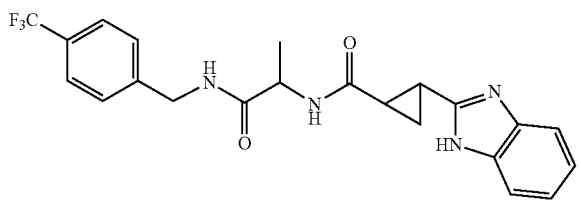 [SMILES: CC(NC(=O)C1CC1c1nc2ccccc2[nH]1)C(=O)NCc1ccc(C(F)(F)F)cc1]

A title compound (white powders, 27 mg, 34%) was obtained in the same manner as in Example 1, by using trans-(2-(1H-benzo[d]imidazol-2-yl) cyclopropane-1-carbonyl)-D-alanine (50 mg, 0.18 mmol) synthesized in Reference Example 1-2 and (4-(trifluoromethyl)phenyl)methanamine (32 mg, 0.18 mmol).

$^1$H NMR (DMSO-d$_6$, 400 MHz): δ=1.24 (d, 3H, J=7 Hz), 1.3-1.6 (m, 2H), 2.3-2.5 (m, 2H), 4.3-4.4 (m, 3H), 7.0-7.2 (m, 2H), 7.3-7.5 (m, 2H), 7.46 (d, 2H, J=8 Hz), 7.69 (d, 2H, J=8 Hz), 8.5-8.7 (m, 2H), 12.38 (brs, 1H).

MS: 431.18 [M+H]$^+$

Example 15

Trans-2-(1H-benzo[d]imidazol-2-yl)-N-(1-oxo-1-(((6-(trifluoromethyl)pyridin-3-yl)methyl)amino) propan-2-yl) cyclopropane-1-carboxamide

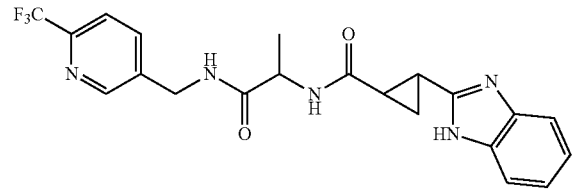 [SMILES: CC(NC(=O)C1CC1c1nc2ccccc2[nH]1)C(=O)NCc1ccc(C(F)(F)F)nc1]

A title compound (white solid, 55 mg, 68%) was obtained in the same manner as in Example 1, by using trans-(2-(1H-benzo[d]imidazol-2-ye cyclopropane-1-carbonyl)-D-alanine (47 mg, 0.17 mmol) synthesized in Reference Example 1-2 and (6-(trifluoromethyl)pyridin-3-yl)methanamine (30 mg, 0.17 mmol).

$^1$H NMR (DMSO-d$_6$, 400 MHz): δ=1.24 (d, 3H, J=7 Hz), 1.4-1.6 (m, 2H), 2.3-2.5 (m, 2H), 4.30 (quint, 1H, J=7 Hz), 4.41 (d, 2H, J=6 Hz), 7.0-7.2 (m, 2H), 7.3-7.5 (m, 2H), 7.8-8.0 (m, 2H), 8.5-8.7 (m, 3H), 12.38 (s, 1H).

MS: 432.15 [M+H]$^+$

Example 16

Trans-2-(1H-benzo[d]imidazol-2-yl)-N-(1-((4-chlorophenyl)amino)-1-oxopropan-2-yl) cyclopropane-1-carboxamide

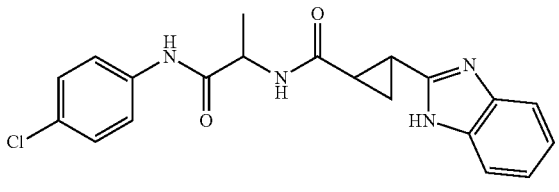 [SMILES: CC(NC(=O)C1CC1c1nc2ccccc2[nH]1)C(=O)Nc1ccc(Cl)cc1]

Diastereomer A (upper spot on TLC (ethyl acetate), white powders, 11 mg, 15%) and Diastereomer B (lower spot on TLC (ethyl acetate), white powders, 11 mg, 15%) of a title compound were obtained in the same manner as in Example 1, by using trans-(2-(1H-benzo[d]imidazol-2-yl) cyclopropane-1-carbonyl)-D-alanine (55 mg, 0.20 mmol) synthesized in Reference Example 1-2 and 4-chloroaniline (51 mg, 0.40 mmol).

Diastereomer A $^1$H NMR (DMSO-d$_6$, 400 MHz): δ=1.28 (d, 3H, J=7 Hz), 1.39 (ddd, 1H, J=3, 6, 9 Hz), 1.49 (ddd, 1H, J=3, 6, 9 Hz), 2.34 (ddd, 1H, J=4, 6, 9 Hz), 2.42 (ddd, 1H, J=4, 6, 9 Hz), 4.42 (quint, 1H, J=7 Hz), 7.0-7.2 (m, 2H), 7.3-7.5 (m, 4H), 7.6-7.7 (m, 2H), 8.67 (d, 1H, J=7 Hz), 10.21 (s, 1H), 12.38 (s, 1H).

MS: 383.10 [M+H]$^+$

Diastereomer B $^1$H NMR (DMSO-d$_6$, 400 MHz): δ=1.31 (d, 3H, J=7 Hz), 1.3-1.5 (m, 2H), 2.3-2.5 (m, 2H), 4.45 (quint, 1H, J=7 Hz), 7.0-7.2 (m, 2H), 7.3-7.5 (m, 4H), 7.6-7.7 (m, 2H), 8.71 (d, 1H, J=7 Hz), 10.24 (s, 1H), 12.41 (s, 1H).

MS: 383.11 [M+H]$^+$

Example 17

Trans-2-(1H-benzo[d]imidazol-2-yl)-N-(1-oxo-1-(pyrazin-2-ylamino)propan-2-yl) cyclopropane-1-carboxamide

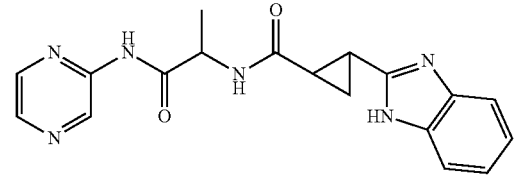 [SMILES: CC(NC(=O)C1CC1c1nc2ccccc2[nH]1)C(=O)Nc1cnccn1]

A title compound (white powders, 44 mg, 83%) was obtained in the same manner as in Example 1, by using trans-2-(1H-benzo[d]imidazol-2-yl) cyclopropane-1-carboxylic acid (36 mg, 0.18 mmol) and 2-amino-N-(pyrazin-2-yl)propanamide (25 mg, 0.15 mmol).

$^1$H NMR (DMSO-d$_6$, 400 MHz): δ=1.2-1.6 (m, 5H), 2.3-2.5 (m, 2H), 4.5-4.7 (m, 1H), 7.0-7.2 (m, 2H), 7.3-7.6 (m, 2H), 8.3-8.5 (m, 2H), 8.6-8.8 (m, 1H), 9.2-9.4 (m, 1H), 10.8-11.0 (m, 1H), 12.3-12.5 (m, 1H).

MS: 351.17 [M+H]$^+$

Example 18

Trans-2-(1H-benzo[d]imidazol-2-yl)-N-(1-((5-bromopyrazin-2-yl)amino)-1-oxopropan-2-yl) cyclopropane-1-carboxamide

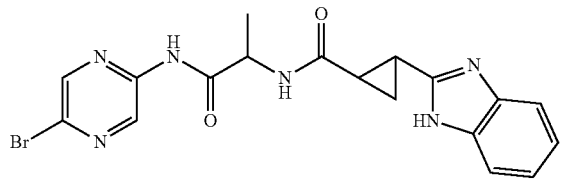 [SMILES: CC(NC(=O)C1CC1c1nc2ccccc2[nH]1)C(=O)Nc1cnc(Br)cn1]

Diastereomer A (upper spot on TLC (ethyl acetate), white powders, 39 mg, 15%) and Diastereomer B (lower spot on TLC (ethyl acetate), white powders, 4 mg, 2%) of a title compound were obtained in the same manner as in Example 1, by using trans-2-(1H-benzo[d]imidazol-2-yl) cyclopropane-1-carboxylic acid (121 mg, 0.60 mmol) and 2-amino-N-(5-bromopyrazin-2-yl)propanamide.

Diastereomer A
$^1$H NMR (DMSO-$d_6$, 400 MHz): δ=1.32 (d, 3H, J=7 Hz), 1.3-1.6 (m, 2H), 2.3-2.5 (m, 2H), 4.57 (quint, 1H, J=7 Hz), 7.0-7.2 (m, 2H), 7.3-7.6 (m, 2H), 8.63 (d, 1H, J=1 Hz), 8.71 (d, 1H, J=6 Hz), 9.14 (d, 1H, J=1 Hz), 11.11 (s, 1H), 12.39 (s, 1H).
MS: 431.07 [M+H]$^+$ Diastereomer B
$^1$H NMR (DMSO-$d_6$, 400 MHz): 3=1.32 (d, 3H, J=7 Hz), 1.3-1.6 (m, 2H), 2.3-2.5 (m, 2H), 4.57 (quint, 1H, J=7 Hz), 7.0-7.2 (m, 2H), 7.3-7.5 (m, 2H), 8.63 (d, 1H, J=2 Hz), 8.73 (d, 1H, J=7 Hz), 9.12 (d, 1H, J=1 Hz), 11.11 (s, 1H), 12.40 (s, 1H).
MS: 431.09 [M+H]$^+$

Example 19

Trans-1-(2-(1H-benzo[d]imidazol-2-yl) cyclopropane-1-carbonyl)-N-(4-(trifluoromethyl)phenyl)pyrrolidine-2-carboxamide

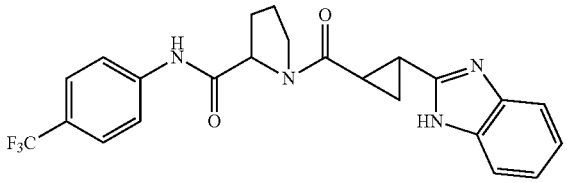 [SMILES: O=C(Nc1ccc(C(F)(F)F)cc1)C1CCCN1C(=O)C1CC1c1nc2ccccc2[nH]1]

Diastereomer A (upper spot on TLC (chloroform/2M ammonia in methanol=20/1), white powders, 35 mg, 52%) and Diastereomer B (lower spot on TLC (chloroform/2M ammonia in methanol=20/1), white powders, 22 mg, 33%) of a title compound were obtained in the same manner as in Example 1, by using trans-2-(1H-benzo[d]imidazol-2-yl) cyclopropane-1-carboxylic acid (40 mg, 0.20 mmol) and N-(4-(trifluoromethyl)phenyl)pyrrolidine-2-carboxamide (39 mg, 0.15 mmol).

Diastereomer A
$^1$H NMR (DMSO-$d_6$, 400 MHz): δ=1.3-1.6 (m, 2H), 1.8-2.6 (m, 6H), 3.3-3.9 (m, 2H), 4.4-4.6 (m, 0.8H), 4.7-4.8 (m, 0.2H), 7.0-7.2 (m, 2H), 7.3-7.6 (m, 2H), 7.6-7.9 (m, 4H), 10.43 (s, 0.8H), 10.64 (s, 0.2H), 12.47 (s, 1H).
MS: 443.15 [M+H]$^+$ Diastereomer B
$^1$H NMR (DMSO-$d_6$, 400 MHz): δ=1.3-1.7 (m, 2H), 1.8-2.5 (m, 6H), 3.3-3.9 (m, 2H), 4.4-4.6 (m, 0.6H), 4.6-4.8 (m, 0.4H), 6.8-7.0 (m, 0.6H), 7.0-7.2 (m, 3.4H), 7.3-7.6 (m, 2H), 7.69 (d, 1H, J=9 Hz), 7.81 (d, 1H, J=9 Hz), 10.39 (s, 0.4H), 10.44 (s, 0.6H), 12.29 (s, 0.4H), 12.41 (s, 0.6H).
MS: 443.15 [M+H]$^+$

Example 20

Trans-2-(1H-benzo[d]imidazol-2-yl)-N-(2-oxo-2-((4-(trifluoromethyl)phenyl)amino)ethyl) cyclopropane-1-carboxamide

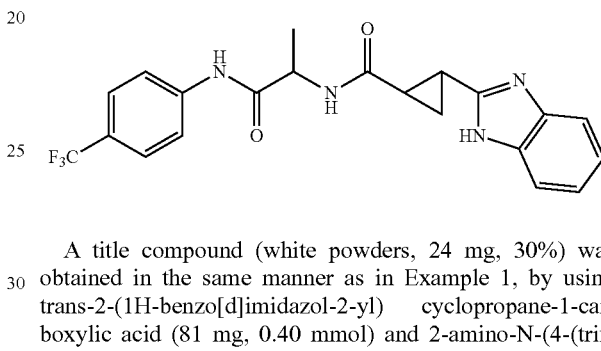

A title compound (white powders, 24 mg, 30%) was obtained in the same manner as in Example 1, by using trans-2-(1H-benzo[d]imidazol-2-yl) cyclopropane-1-carboxylic acid (81 mg, 0.40 mmol) and 2-amino-N-(4-(trifluoromethyl)phenyl)acetamide (44 mg, 0.20 mmol).
$^1$H NMR (DMSO-$d_6$, 400 MHz): δ=1.4-1.6 (m, 2H), 2.3-2.6 (m, 2H), 3.99 (m, 2H), 7.0-7.2 (m, 2H), 7.3-7.6 (m, 2H), 7.68 (d, 2H, J=9 Hz), 7.80 (d, 2H, J=9 Hz), 8.74 (t, 1H, J=6 Hz), 10.44 (s, 1H), 12.41 (s, 1H).
MS: 403.18 [M+H]$^+$

Example 21

Trans-1-(2-(1H-benzo[d]imidazol-2-yl) cyclopropane-1-carboxamido)-N-(4-(trifluoromethyl)phenyl) cyclopropane-1-carboxamide

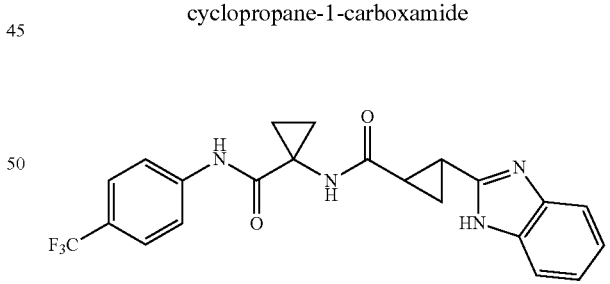

A title compound (white powders, 59 mg, 69%) was obtained in the same manner as in Example 1, by using trans-2-(1H-benzo[d]imidazol-2-yl) cyclopropane-1-carboxylic acid (81 mg, 0.40 mmol) and 1-amino-N-(4-(trifluoromethyl)phenyl) cyclopropane-1-carboxamide (49 rug, 0.20 mmol).
$^1$H NMR (DMSO-$d_6$, 400 MHz): δ=0.9-1.1 (m, 2H), 1.3-1.6 (m, 4H), 2.3-2.6 (m, 2H), 7.0-7.2 (m, 2H), 7.3-7.6 (m, 2H), 7.67 (d, 2H, J=9 Hz), 7.86 (d, 2H, J=8 Hz), 8.87 (s, 1H), 9.92 (s, 1H), 12.43 (s, 1H).
MS: 429.16 [M+H]$^+$

Example 22

1-((1S, 2S)-2-(1H-Benzo[d]imidazol-2-yl) cyclopropane-1-carboxamido)-N-(3-(trifluoromethyl)phenyl) cyclopropane-1-carboxamide

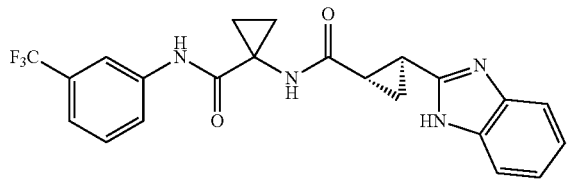 [SMILES: O=C(NC1(C(=O)Nc2cccc(C(F)(F)F)c2)CC1)[C@H]1C[C@@H]1c1nc2ccccc2[nH]1]

A title compound (white powders, 11 mg, 27%) was obtained in the same manner as in Example 1, by using (1S, 2S)-2-(1H-benzo[d]imidazol-2-yl) cyclopropane-1-carboxylic acid (20 mg, 0.10 mmol) synthesized in Reference Example 7-2 and 1-amino-N-(3-(trifluoromethyl)phenyl) cyclopropane-1-carboxamide (50 mg, 0.20 mmol).

$^1$H NMR (DMSO-$d_6$, 400 MHz): δ=0.9-1.1 (m, 2H), 1.3-1.6 (m, 4H), 2.3-2.4 (m, 1H), 2.4-2.5 (m, 1H), 7.0-7.2 (m, 2H), 7.3-7.5 (m, 3H), 7.54 (t, 1H, J=8 Hz), 7.93 (d, 1H, J=8 Hz), 8.07 (s, 1H), 8.86 (s, 1H), 9.92 (s, 1H), 12.43 (s, 1H).

MS: 429.15 [M+H]$^+$

Example 23

(1S, 2S)-2-(1H-Benzo[d]imidazol-2-yl)-N-(2-oxo-1-(4-(trifluoromethyl)phenyl)pyrrolidin-3-yl) cyclopropane-1-carboxamide

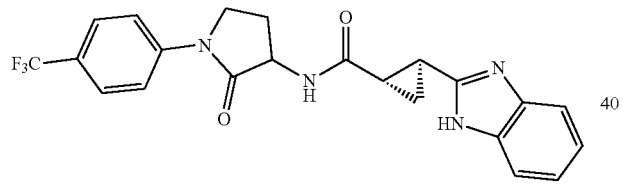

Diastereomer A (upper spot on TLC (ethyl acetate/methanol=19/1), white powders, 3 mg, 28%) and Diastereomer B (lower spot on TLC (ethyl acetate/methanol=19/1), white powders, 2 mg, 18%) of a title compound were obtained in the same manner as in Example 1, by using (1S, 2S)-2-(1H-benzo[d]imidazol-2-yl) cyclopropane-1-carboxylic acid (4 mg, 0.02 mmol) synthesized in Reference Example 7-2 and 3-amino-1-(4-(trifluoromethyl)phenyl)pyrrolidin-2-one (6 mg, 0.02 mmol).

Diastereomer A $^1$H NMR (CD$_3$OD, 400 MHz): δ=1.6-1.8 (m, 2H), 2.0-2.2 (m, 1H), 2.3-2.4 (m, 1H), 2.5-2.7 (m, 2H), 3.92 (dd, 2H, J=4, 9 Hz), 4.72 (dd, 1H, J=9, 10 Hz), 7.2-7.3 (m, 2H), 7.4-7.6 (m, 2H), 7.69 (d, 2H, J=9 Hz), 7.90 (d, 2H, J=9 Hz). 2H cannot be observed.

MS: 429.17 [M+H]$^+$

Diastereomer B $^1$H NMR (CD$_3$OD, 400 MHz): δ=1.6-1.8 (m, 2H), 2.0-2.2 (m, 1H), 2.3-2.4 (m, 1H), 2.5-2.8 (m, 2H), 3.9-4.0 (m, 2H), 4.78 (dd, 1H, J=9, 10 Hz), 7.2-7.4 (m, 2H), 7.5-7.6 (m, 2H), 6.81 (d, 2H, J=9 Hz), 8.89 (d, 2H, J=9 Hz). 2H cannot be observed.

MS: 429.18 [M+H]$^+$

Example 24

1-((1S, 2S)-2-(1H-Benzo[d]imidazol-2-yl) cyclopropane-1-carboxamido)-N-(4-(trifluoromethoxy)phenyl) cyclopropane-1-carboxamide

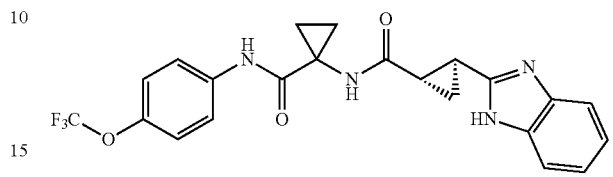

A title compound (white powders, 28 mg, 64%) was obtained in the same manner as in Example 1, by using (1S, 2S)-2-(1H-benzo[d]imidazol-2-yl) cyclopropane-1-carboxylic acid (20 mg, 0.10 mmol) synthesized in Reference Example 7-2 and 1-amino-N-(4-trifluoromethoxy)phenyl) cyclopropane-1-carboxamide (55 mg, 0.20 mmol).

$^1$H NMR (DMSO-$d_6$, 400 MHz): δ=0.9-1.1 (m, 2H), 1.3-1.6 (m, 4H), 2.3-2.4 (m, 1H), 2.4-2.5 (m, 1H), 7.0-7.2 (m, 2H), 7.3-7.5 (m, 2H), 7.31 (d, 2H, J=9 Hz), 7.71 (d, 2H, J=9 Hz), 8.82 (s, 1H), 9.76 (s, 1H), 12.42 (s, 1H).

MS: 445.17 [M+H]$^+$

Example 25

1-((1S, 2S)-2-(1H-Benzo[d]imidazol-2-yl) cyclopropane-1-carboxamido)-N-(2-(trifluoromethyl)phenyl) cyclopropane-1-carboxamide

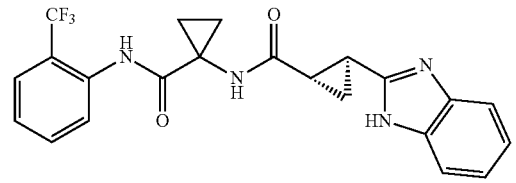 [SMILES: O=C(NC1(C(=O)Nc2ccccc2C(F)(F)F)CC1)[C@H]1C[C@@H]1c1nc2ccccc2[nH]1]

A title compound (white powders, 1 mg, 3%) was obtained in the same manner as in Example 1, by using (1S, 2S)-2-(1H-benzo[d]imidazol-2-yl) cyclopropane-1-carboxylic acid (16 mg, 0.08 mmol) synthesized in Reference Example 7-2 and 1-amino-N-(2-(trifluoromethyl)phenyl cyclopropane-1-carboxamide (20 mg, 0.08 mmol).

$^1$H NMR (CDCl$_3$, 400 MHz): δ=1.1-1.3 (m, 4H), 1.7-1.9 (m, 2H), 2.4-2.5 (m, 1H), 2.7-2.8 (m, 1H), 7.01 (s, 1H), 7.18 (t, 1H, J=8 Hz), 7.2-7.3 (m, 2H), 7.4-7.6 (m, 4H), 8.30 (d, 1H, J=8 Hz), 8.68 (s, 1H), 10.02 (brs, 1H).

MS: 429.16 [M+H]$^+$

Example 26

1-((1S, 2S)-2-(1H-Benzo[d]imidazol-2-yl) cyclopropane-1-carboxamido)-N-(4-(trifluoromethyl)phenyl) cyclopropane-1-carboxamide

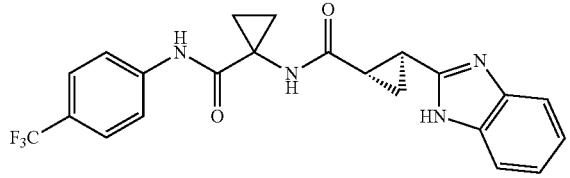 [SMILES: O=C(NC1(C(=O)Nc2ccc(C(F)(F)F)cc2)CC1)[C@H]1C[C@@H]1c1nc2ccccc2[nH]1]

A title compound (white powders, 204 mg, 75%) was obtained in the same manner as in Example 1, by using (1S, 2S)-2-(1H-benzo[d]imidazol-2-yl) cyclopropane-1-carboxylic acid (255 mg, 1.26 mmol) synthesized in Reference Example 7-2 and 1-amino-N-(4-(trifluoromethyl)phenyl) cyclopropane-1-carboxamide (154 mg, 0.63 mmol).

1H NMR (DMSO-$d_6$, 400 MHz): δ=0.9-1.1 (m, 2H), 1.4-1.6 (m, 4H), 2.3-2.4 (m, 1H), 2.4-2.5 (m, 1H), 7.0-7.2 (m, 2H), 7.44 (brs, 2H), 7.67 (d, 2H, J=9 Hz), 7.85 (d, 2H, J=9 Hz), 8.85 (s, 1H), 9.91 (s, 1H), 12.43 (brs, 1H).

MS: 429.14 [M+H]$^+$

Example 27

1-((1S, 2S)-2-(1-Ethyl-1H-benzo[d]imidazol-2-yl) cyclopropane-1-carboxamido)-N-(6-(trifluoromethyl)pyridin-3-yl) cyclopropane-1-carboxamide

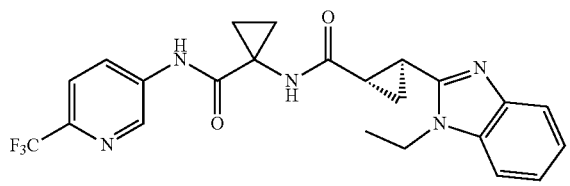 [SMILES: CCn1c([C@H]2C[C@@H]2C(=O)NC2(C(=O)Nc3ccc(C(F)(F)F)nc3)CC2)nc2ccccc21]

A title compound (white powders, 27 mg, 44%) was obtained in the same manner as in Example 1, by using (1S, 2S)-2-(1-ethyl-1H-benzo[d]imidazol-2-yl) cyclopropane-1-carboxylic acid (31 mg, 0.13 mmol) synthesized in Reference Example 8-2 and 1-amino-N-(6-(trifluoromethyl)pyridin-3-yl) cyclopropane-1-carboxamide (49 mg, 0.20 mmol).

1H NMR (CD$_3$OD, 400 MHz): δ=1.17 (dd, 2H, J=5, 9 Hz), 1.42 (d, 3H, J=7 Hz), 1.5-1.8 (m, 4H), 2.39 (ddd, 1H, J=4, 6, 10 Hz), 2.68 (ddd, 1H, J=4, 6, 10 Hz), 4.39 (q, 2H, J=7 Hz), 7.2-7.3 (m, 2H), 7.4-7.6 (m, 2H), 7.77 (d, 1H, J=9 Hz), 8.32 (dd, 1H, J=2, 9 Hz), 8.87 (d, 1H, J=2 Hz). 2H cannot be observed.

MS: 458.19 [M+H]$^+$

Example 28

1-((1S, 2S)-2-(1H-Benzo[d]imidazol-2-yl) cyclopropane-1-carboxamido)-N-(2-fluoro-4-(trifluoromethyl)phenyl) cyclopropane-1-carboxamide

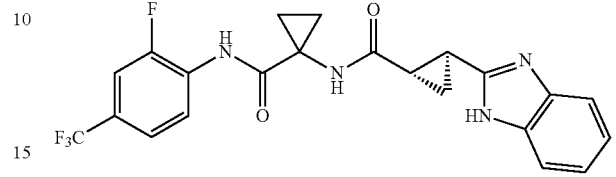

A title compound (white powders, 64 mg, 82%) was obtained in the same manner as in Example 1, by using (1S, 2S)-2-(1H-benzo[d]imidazol-2-yl) cyclopropane-1-carboxylic acid (71 mg, 0.35 mmol) synthesized in Reference Example 7-2 and 1-amino-N-(2-fluoro-4-(trifluoromethyl) phenyl) cyclopropane-1-carboxamide (46 mg, 0.18 mmol) synthesized in Reference Example 3-2.

1H NMR (CD$_3$OD, 400 MHz): δ=1.17 (dd, 2H, J=5, 8 Hz), 1.59 (dd, 2H, J=5, 8 Hz), 1.6-1.7 (m, 2H), 2.34 (ddd, 1H, J=4, 6, 10 Hz), 2.6-2.7 (m, 1H), 7.1-7.3 (m, 2H), 7.4-7.6 (m, 4H), 8.0-8.2 (m, 1H). 3H cannot be observed.

MS: 447.17 [M+H]$^+$

Example 29

1-((1S, 2S)-2-(1H-Benzo[d]imidazol-2-yl) cyclopropane-1-carboxamido)-N-(5-(trifluoromethyl)pyridin-3-yl) cyclopropane-1-carboxamide

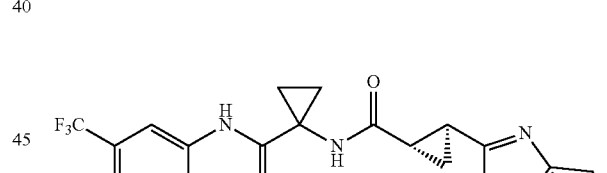

A title compound (white powders, 24 mg, 64%) was obtained in the same manner as in Example 1, by using (1S, 2S)-2-(1H-benzo[d]imidazol-2-yl) cyclopropane-1-carboxylic acid (33 mg, 0.16 mmol) synthesized in Reference Example 7-2 and 1-amino-N-(5-(trifluoromethyl)pyridin-3-yl) cyclopropane-1-carboxamide (20 mg, 0.08 mmol) synthesized in Reference Example 4-2.

1H NMR (CD$_3$OD, 400 MHz): δ=1.0-1.2 (m, 2H), 1.5-1.7 (m, 4H), 2.34 (ddd, 1H, J=4, 7, 11 Hz), 2.5-2.7 (m, 1H), 7.19 (ddd, 2H, J=4, 4, 10 Hz), 7.4-7.5 (m, 2H), 8.47 (dd, 1H, J=2, 2 Hz), 8.58 (d, 1H, J=2 Hz), 8.96 (d, 1H, J=2 Hz). 3H cannot be observed.

MS: 430.17 [M+H]$^+$

Example 30

(1S, 2S)-2-(1H-Benzo[d]imidazol-2-yl)-N-(2-(isopropyl (6-(trifluoromethyl)pyridin-3-yl)amino)-2-oxoethyl) cyclopropane-1-carboxamide

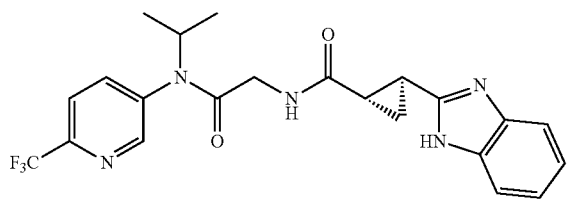 [SMILES: CC(C)N(C(=O)CNC(=O)[C@H]1C[C@@H]1c1nc2ccccc2[nH]1)c1ccc(C(F)(F)F)nc1]

A title compound (white powders, 40 mg, 48%) was obtained in the same manner as in Example 1, by using (1S, 2S)-2-(1H-benzo[d]imidazol-2-yl) cyclopropane-1-carboxylic acid (75 mg, 0.37 mmol) synthesized in Reference Example 7-2 and 2-amino-N-isopropyl-N-(6-(trifluoromethyl)pyridin-3-yl)acetamide (49 mg, 0.19 mmol) synthesized in Reference Example 5.

1H NMR (DMSO-$d_6$, 400 MHz): δ=1.02 (d, 6H, J=6 Hz), 1.36 (ddd, 1H, J=4, 6, 9 Hz), 1.4-1.5 (m, 1H), 2.3-2.4 (m, 2H), 3.3-3.4 (m, 2H), 4.7-4.9 (m, 1H), 7.0-7.2 (m, 2H), 7.3-7.5 (m, 2H), 8.0-8.2 (m, 2H), 8.54 (t, 1H, J=6 Hz), 8.73 (s, 1H), 12.37 (s, 1H).

MS: 446.20 [M+H]$^+$

Example 31

1-((1S, 2S)-2-(1H-Benzo[d]imidazol-2-yl) cyclopropane-1-carboxamido)-N-(4-fluoro-3-(trifluoromethyl)phenyl) cyclopropane-1-carboxamide

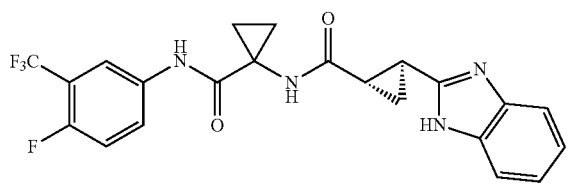 [SMILES: O=C(NC1(C(=O)Nc2ccc(F)c(C(F)(F)F)c2)CC1)[C@H]1C[C@@H]1c1nc2ccccc2[nH]1]

A title compound (white powders, 39 mg, 45%) was obtained in the same manner as in Example 1, by using (1S, 2S)-2-(1H-benzo[d]imidazol-2-yl) cyclopropane-1-carboxylic acid (77 mg, 0.38 mmol) synthesized in Reference Example 7-2 and 1-amino-N-(4-fluoro-3-(trifluoromethyl)phenyl) cyclopropane-1-carboxamide (50 mg, 0.19 mmol).

1H NMR (DMSO-$d_6$, 400 MHz): δ=0.9-1.1 (m, 2H), 1.4-1.6 (m, 4H), 2.3-2.6 (m, 2H), 7.0-7.2 (m, 2H), 7.3-7.5 (m, 3H), 7.9-8.0 (m, 1H), 8.09 (dd, 1H, J=2, 7 Hz), 8.85 (d, 1H, J=9 Hz), 9.94 (d, 1H, J=7 Hz), 12.42 (s, 1H).

MS: 447.16 [M+H]$^+$

Example 32

(1S, 2S)-2-(1H-Benzo[d]imidazol-2-yl)-N-(1-((4-fluoro-3-(trifluoromethyl)phenyl)amino)-3-methoxy-1-oxopropan-2-yl) cyclopropane-1-carboxamide

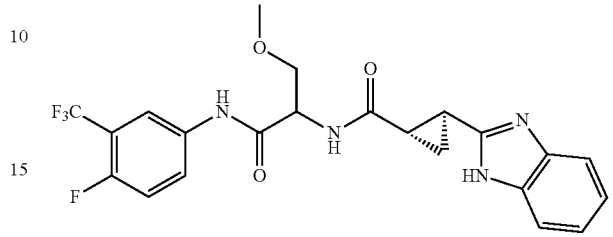

Diastereomer A (upper spot on TLC (ethyl acetate), white powders, 32 mg, 28%) and Diastereomer B (lower spot on TLC (ethyl acetate), white powders, 11 mg, 9%) of a title compound were obtained in the same manner as in Example 1, by using (1S, 2S)-2-(1H-benzo[d]imidazol-2-yl) cyclopropane-1-carboxylic acid (76 mg, 0.38 mmol) synthesized in Reference Example 7-2 and 2-amino-N-(4-fluoro-3-(trifluoromethyl)phenyl)-3-methoxypropanamide (70 mg, 0.25 mmol).

Diastereomer A

1H NMR (DMSO-$d_6$, 400 MHz): δ=1.3-1.6 (m, 2H), 2.4-2.5 (m, 2H), 3.26 (s, 3H), 3.5-3.7 (m, 2H), 4.6-4.7 (m, 1H), 7.0-7.2 (m, 2H), 7.4-7.6 (m, 3H), 7.8-7.9 (m, 1H), 8.14 (dd, 1H, J=3, 6 Hz), 8.78 (d, 1H, J=7 Hz), 10.58 (s, 1H), 12.38 (s, 1H).

MS: 465.16 [M+H]$^+$

Diastereomer B

1H NMR (DMSO-$d_6$, 400 MHz): δ=1.4-1.6 (m, 2H), 2.3-2.5 (m, 2H), 3.28 (s, 3H), 3.5-3.7 (m, 2H), 4.6-4.7 (m, 1H), 7.0-7.2 (m, 2H), 7.3-7.6 (m, 3H), 7.8-7.9 (m, 1H), 8.12 (dd, 1H, J=3, 6 Hz), 8.81 (d, 1H, J=7 Hz), 10.60 (s, 1H), 12.39 (s, 1H).

MS: 465.17 [M+H]$^+$

Example 33

(1S, 2S)-2-(1H-Benzo[d]imidazol-2-yl)-N-(5-oxo-1-(6-(trifluoromethyl)pyridin-3-yl)pyrrolidin-3-yl) cyclopropane-1-carboxamide

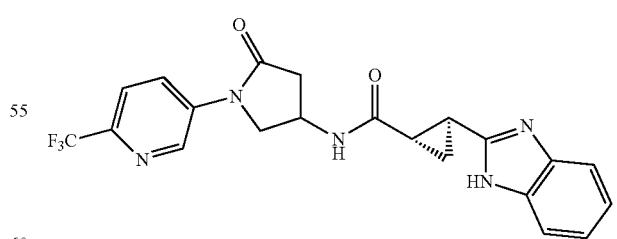

Trifluoroacetic acid (1 mL) was added to tert-butyl (5-oxo-1-(6-(trifluoromethyl)pyridin-3-yl)pyrrolidin-3-yl) carbamate (9 mg, 0.03 mmol) synthesized in Reference Example 6, followed by stirring at room temperature for 20 minutes. A saturated aqueous sodium hydrogen carbonate solution was added to a reaction liquid, and then extraction was performed with ethyl acetate. A separated organic layer was dried over anhydrous sodium sulfate, an insoluble substance was filtered, and then a solvent was distilled off under reduced pressure to obtain a crude product (light yellow oil, 20 mg) of 4-amino-1-(6-(trifluoromethyl)pyridin-3-yl)pyrrolidin-2-one.

Diastereomer A (upper spot on TLC (ethyl acetate/methanol=9/1), white powders, 2 mg, 17%) and Diastereomer B (lower spot on TLC (ethyl acetate/methanol=9/1), white powders, 4 mg, 43%) of a title compound were obtained in the same manner as in Example 1, by using the obtained crude product (20 mg) and (1S, 2S)-2-(1H-benzo[d]imidazol-2-yl) cyclopropane-1-carboxylic acid (10 mg, 0.05 mmol) synthesized in Reference Example 7-2.

Diastereomer A

1H NMR (CD$_3$OD, 400 MHz): δ=1.6-1.7 (m, 2H), 2.2-2.3 (m, 1H), 2.5-2.7 (m, 2H), 3.05 (dd, 1H, J=8, 17 Hz), 3.85 (dd, 1H, J=3, 10 Hz), 4.31 (dd, 1H, J=5, 10 Hz), 4.6-4.7 (m, 1H), 7.1-7.2 (m, 2H), 7.4-7.5 (m, 2H), 7.83 (d, 1H, J=9 Hz), 8.30 (dd, 1H, J=3, 9 Hz), 9.09 (d, 1H, J=3 Hz). 2H cannot be observed.

MS: 430.14 [M+H]$^+$

Diastereomer B

1H NMR (CD$_3$OD, 400 MHz): δ=L6-1.7 (m, 2H), 2.2-2.3 (m, 1H), 2.5-2.7 (m, 2H), 3.06 (dd, 1H, J=8, 17 Hz), 3.84 (dd, 1H, J=3, 11 Hz), 4.31 (dd, 1H, J=6, 11 Hz), 4.6-4.7 (m, 1H), 7.1-7.2 (m, 2H), 7.4-7.5 (m, 2H), 7.82 (d, 1H, J=9 Hz), 8.30 (dd, 1H, J=2, 9 Hz), 9.07 (d, 1H, J=2H). 2H cannot be observed.

MS: 430.14 [M+H]$^+$

Example 34

1-((1S, 2S)-2-(5-Chloro-1H-benzo[d]imidazol-2-yl) cyclopropane-1-carboxamido)-N-(4-fluoro-3-(trifluoromethyl)phenyl) cyclopropane-1-carboxamide

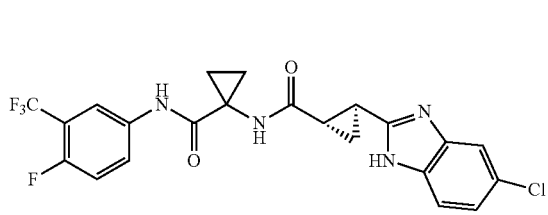 [SMILES: O=C(NC1(C(=O)Nc2ccc(F)c(C(F)(F)F)c2)CC1)[C@H]1C[C@@H]1c1nc2cc(Cl)ccc2[nH]1]

A title compound (white powders, 16 mg, 43%) was obtained in the same manner as in Example 1, by using (1S, 2S)-2-(5-chloro-1H-benzo[d]imidazol-2-yl) cyclopropane-1-carboxylic acid (36 mg, 0.15 mmol) synthesized in Reference Example 9-2 and 1-amino-N-(4-fluoro-3-(trifluoromethyl)phenyl) cyclopropane-1-carboxamide (20 mg, 0.08 mmol).

1H NMR (DMSO-d$_6$, 400 MHz): δ=0.9-1.1 (m, 2H), 1.4-1.6 (m, 4H), 2.3-2.6 (m, 2H), 7.14 (dd, 1H, J=2, 8 Hz), 7.4-7.6 (m, 3H), 7.9-8.0 (m, 1H), 8.08 (dd, 1H, J=2, 7 Hz), 8.90 (s, 1H), 9.96 (s, 1H). 1H cannot be observed.

MS: 481.08 [M+H]$^+$

Example 35

1-((1S, 2S)-2-(1H-Benzo[d]imidazol-2-yl) cyclopropane-1-carboxamido)-N-(3,5-dichlorophenyl) cyclopropane-1-carboxamide

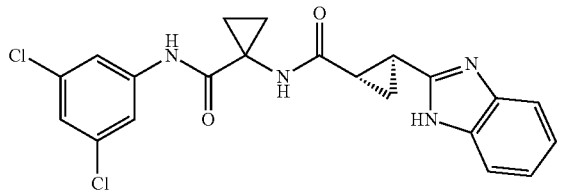 [SMILES: O=C(NC1(C(=O)Nc2cc(Cl)cc(Cl)c2)CC1)[C@H]1C[C@@H]1c1nc2ccccc2[nH]1]

A title compound (white powders, 3 mg, 9%) was obtained in the same manner as in Example 33, by using tert-butyl (1-(3,5-dichlorophenyl)carbamoyl)cyclopropyl) carbamate (32 mg, 0.08 mmol) and (1S, 2S)-2-(1H-benzo[d]imidazol-2-yl) cyclopropane-1-carboxylic acid (40 mg, 0.17 mmol) synthesized in Reference Example 7-2.

1H NMR (CD$_3$OD, 400 MHz): δ=1.0-1.2 (m, 2H), 1.5-1.7 (m, 4H), 2.3-2.4 (m, 1H), 2.5-2.7 (m, 1H), 7.1-7.3 (m, 3H), 7.4-7.6 (m, 2H), 7.63 (d, 2H, J=1 Hz). 3H cannot be observed.

MS: 429.07 [M+H]$^+$

Example 36

1-((1S, 2S)-2-(1H-Benzo[d]imidazol-2-yl) cyclopropane-1-carboxamido)-N-(3-(trifluoromethyl)phenyl) cyclobutane-1-carboxamide

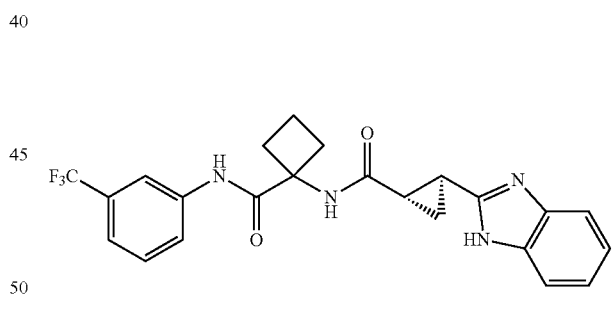

A title compound (white powders, 24 mg, 33%) was obtained in the same manner as in Example 1, by using (1S, 2S)-2-(1H-benzo[d]imidazol-2-yl) cyclopropane-1-carboxylic acid (58 mg, 0.27 mmol) synthesized in Reference Example 7-2 and 1-amino-N-(3-(trifluoromethyl)phenyl) cyclobutane-1-carboxamide (41 mg, 0.16 mmol).

1H NMR (DMSO-d$_6$, 400 MHz): δ=1.3-1.6 (m, 2H), 1.7-2.0 (m, 2H), 2.14 (dt, 2H, J=10, 17 Hz), 2.41 (t, 2H, J=7 Hz), 2.5-2.7 (m, 2H), 7.0-7.2 (m, 2H), 7.3-7.6 (m, 4H), 7.88 (d, 1H, J=9 Hz), 8.12 (s, 1H), 8.97 (s, 1H), 9.82 (s, 1H), 12.41 (s, 1H).

MS: 443.17 [M+H]$^+$

Example 37

(1S, 2S)-2-(1H-Benzo[d]imidazol-2-yl)-N—((R)-4-methyl-1-oxo-1-((3-(trifluoromethyl)phenyl)amino)pentan-2-yl) cyclopropane-1-carboxamide

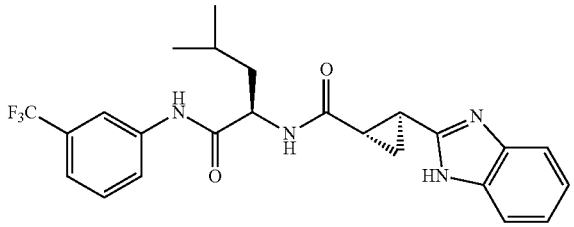 [SMILES: CC(C)C[C@@H](NC(=O)[C@H]1C[C@@H]1c1nc2ccccc2[nH]1)C(=O)Nc1cccc(C(F)(F)F)c1]

A title compound (white powders, 101 mg, 75%) was obtained in the same manner as in Example 1, by using (1S, 2S)-2-(1H-benzo[d]imidazol-2-yl) cyclopropane-1-carboxylic acid (104 mg, 0.44 mmol) synthesized in Reference Example 7-2 and (R)-2-amino-4-methyl-N-(3-(trifluoromethyl)phenyl)pentanamide (81 mg, 0.29 mmol).

1H NMR (DMSO-$d_6$, 400 MHz): δ=0.90 (t, 6H, J=6 Hz), 1.3-1.7 (m, 5H), 2.3-2.5 (m, 2H), 4.47 (ddd, 1H, J=6, 8, 10 Hz), 7.0-7.2 (m, 2H), 7.3-7.5 (m, 3H), 7.57 (t, 1H, J=8 Hz), 7.83 (d, 1H, J=9 Hz), 8.14 (s, 1H), 8.64 (d, 1H, J=7 Hz), 10.50 (s, 1H), 12.38 (s, 1H).

MS: 459.20 [M+H]$^+$

Example 38

Trans-2-(1H-benzo[d]imidazol-2-yl)-N-(1-oxo-1-((3-(trifluoromethyl)phenyl)amino)propan-2-yl) cyclopropane-1-carboxamide

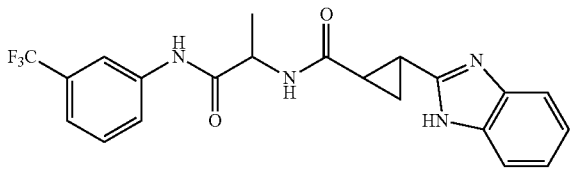 [SMILES: CC(NC(=O)C1CC1c1nc2ccccc2[nH]1)C(=O)Nc1cccc(C(F)(F)F)c1]

Diastereomer A (upper spot on TLC (hexane/ethyl acetate=1/4), light yellow powders, 10 mg, 4%) and Diastereomer B (lower spot on TLC (hexane/ethyl acetate=1/4), white powders, 13 mg, 6%) of a title compound were obtained in the same manner as in Example 1, by using trans-(2-(1H-benzo[d]imidazol-2-yl) cyclopropane-1-carbonyl)-D-alanine (150 mg, 0.55 mmol) synthesized in Reference Example 1-2 and 3-(trifluoromethyl)aniline (136 µL, 1.10 mmol).

Diastereomer A $^1$H NMR (DMSO-$d_6$, 400 MHz): δ=1.32 (d, 3H, J=7 Hz), 1.41 (ddd, 1H, J=4, 6, 9 Hz), 1.50 (ddd, 1H, J=4, 6, 9 Hz), 2.3-2.5 (m, 2H), 4.44 (quint, 1H, J=7 Hz), 7.0-7.2 (m, 2H), 7.3-7.5 (m, 3H), 7.56 (t, 1H, J=8 Hz), 7.80 (d, 1H, J=9 Hz), 8.12 (s, 1H), 8.68 (d, 1H, J=7 Hz), 10.40 (s, 1H), 12.35 (s, 1H).

MS: 417.15 [M+H]$^+$

Diastereomer B $^1$H NMR (DMSO-$d_6$, 400 MHz): δ=1.3-1.5 (m, 5H), 2.42 (t, 2H, J=7 Hz), 4.44 (quint, 1H, J=7 Hz), 7.0-7.2 (m, 2H), 7.3-7.5 (m, 3H), 7.55 (t, 1H, J=8 Hz), 7.79 (d, 1H, J=8 Hz), 8.10 (s, 1H), 8.70 (d, 1H, J=7 Hz), 10.41 (s, 1H), 12.37 (s, 1H).

MS: 417.16 [M+H]+

Example 39

(1S, 2S)-2-(1H-Benzo[d]imidazol-2-yl)-N-(2-oxo-2-((3-(trifluoromethyl)phenyl)amino)ethyl) cyclopropane-1-carboxamide

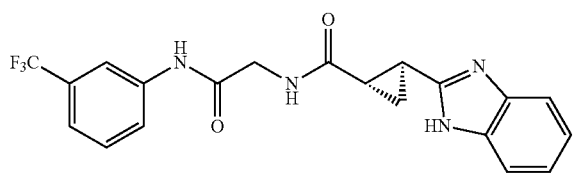 [SMILES: O=C(CNC(=O)[C@H]1C[C@@H]1c1nc2ccccc2[nH]1)Nc1cccc(C(F)(F)F)c1]

A title compound (white powders, 47 mg, 67%) was obtained in the same manner as in Example 33, by using tert-butyl (2-oxo-2-((3-(trifluoromethyl)phenyl)amino)ethyl)carbamate (55 mg, 0.17 mmol) and (1S, 2S)-2-(1H-benzo[d]imidazol-2-yl) cyclopropane-1-carboxylic acid (61 mg, 0.26 mmol) synthesized in Reference Example 7-2.

1H NMR (DMSO-$d_6$, 400 MHz): δ=1.4-1.6 (m, 2H), 2.3-2.5 (m, 2H), 3.9-4.1 (m, 2H), 7.0-7.2 (m, 2H), 7.3-7.5 (m, 3H), 7.56 (t, 1H, J=8 Hz), 7.77 (d, 1H, J=8 Hz), 8.09 (s, 1H), 8.71 (d, 1H, J=6 Hz), 10.38 (s, 1H), 12.38 (s, 1H).

MS: 403.15 [M+H]$^+$

Example 40

1-((1S, 2S)-2-(1-Cyclopropyl-1H-benzo[d]imidazol-2-yl) cyclopropane-1-carboxamido)-N-(3-(trifluoromethyl)phenyl) cyclopropane-1-carboxamide

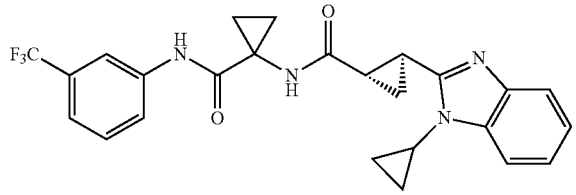 [SMILES: O=C(NC1(C(=O)Nc2cccc(C(F)(F)F)c2)CC1)[C@H]1C[C@@H]1c1nc2ccccc2n1C1CC1]

A title compound (white powders, 33 mg, 86%) was obtained in the same manner as in Example 1, by using (1S, 2S)-2-(1-cyclopropyl-1H-benzo[d]imidazol-2-yl) cyclopropane-1-carboxylic acid (40 mg, 0.17 mmol) synthesized in Reference Example 10-2 and 1-amino-N-(3-(trifluoromethyl)phenyl) cyclopropane-1-carboxamide (20 mg, 0.083 mmol).

1H NMR (DMSO-$d_6$, 400 MHz): δ=0.9-1.7 (m, 11H), 2.2-2.3 (m, 1H), 2.73 (ddd, 1H, J=4, 6, 9 Hz), 7.1-7.6 (m, 6H), 7.99 (d, 1H, J=8 Hz), 8.03 (s, 1H), 8.81 (s, 1H), 9.90 (s, 1H).

MS: 469.18 [M+H]$^+$

Example 41

1-((1S, 2S)-2-(1H-Benzo[d]imidazol-2-yl) cyclopropane-1-carboxamido)-N-(2-fluoro-3-(trifluoromethyl)phenyl) cyclopropane-1-carboxamide

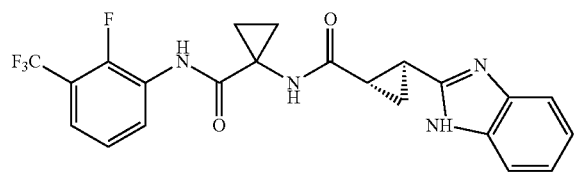 [SMILES: O=C(NC1(C(=O)Nc2cccc(C(F)(F)F)c2F)CC1)[C@H]1C[C@@H]1c1nc2ccccc2[nH]1]

A title compound (white powders, 10 mg, 69%) was obtained in the same manner as in Example 33, by using tert-butyl (1-((2-fluoro-3-(trifluoromethyl)phenyl)carbamoyl)cyclopropyl)carbamate (12 mg, 0.033 mmol) synthesized in Reference Example 11 and (1S, 2S)-2-(1H-benzo[d]imidazol-2-yl) cyclopropane-1-carboxylic acid (14 mg, 0.067 mmol) synthesized in Reference Example 7-2.

1H NMR (DMSO-$d_6$, 400 MHz): δ=1.03 (dd, 2H, J=5, 8 Hz), 1.3-1.6 (m, 4H), 2.2-2.6 (m, 2H), 7.0-7.2 (m, 2H), 7.3-7.5 (m, 3H), 7.58 (t, 1H, J=7 Hz), 7.85 (d, 1H, J=7 Hz), 8.99 (s, 1H), 9.67 (s, 1H), 12.40 (s, 1H).

MS: 447.14 [M+H]$^+$

Example 42

1-((1S, 2S)-2-(1H-Benzo[d]imidazol-2-yl) cyclopropane-1-carboxamido)-N-(3-fluoro-5-(trifluoromethyl)phenyl) cyclopropane-1-carboxamide

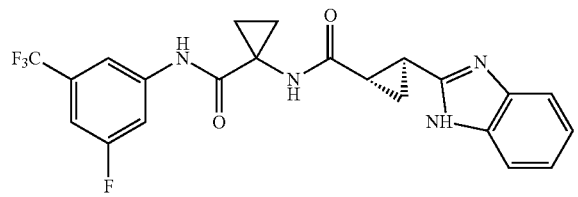 [SMILES: O=C(NC1(C(=O)Nc2cc(F)cc(C(F)(F)F)c2)CC1)[C@H]1C[C@@H]1c1nc2ccccc2[nH]1]

A title compound (white powders, 19 mg, 62%) was obtained in the same manner as in Example 33, by using tert-butyl (1-((3-fluoro-5-(trifluoromethyl)phenyl)carbamoyl)cyclopropyl)carbamate (25 mg, 0.068 mmol) synthesized in Reference Example 12 and (1S, 2S)-2-(1H-benzo[d]imidazol-2-yl) cyclopropane-1-carboxylic acid (27 mg, 0.14 mmol) synthesized in Reference Example 7-2.

1H NMR (DMSO-$d_6$, 400 MHz): δ=0.9-1.1 (m, 2H), 1.4-1.6 (m, 4H), 2.34 (ddd, 1H, J=4, 6, 9 Hz), 2.4-2.6 (m, 1H), 7.0-7.2 (m, 2H), 7.3-7.5 (m, 3H), 7.9-8.0 (m, 2H), 8.87 (s, 1H), 10.08 (s, 1H), 12.42 (s, 1H).

MS: 447.13 [M+H]$^+$

Example 43

1-((1S, 2S)-2-(1H-Benzo[d]imidazol-2-yl) cyclopropane-1-carboxamido)-N-(3-(trifluoromethoxy)phenyl) cyclopropane-1-carboxamide

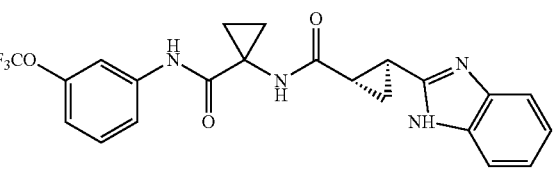

A title compound (white powders, 33 mg, 44%) was obtained in the same manner as in Example 1, by using (1S, 2S)-2-(1H-benzo[d]imidazol-2-yl) cyclopropane-1-carboxylic acid (34 mg, 0.17 mmol) synthesized in Reference Example 7-2 and 1-amino-N-(3-(trifluoromethoxy)phenyl) cyclopropane-1-carboxamide (67 mg, 0.25 mmol).

1H NMR (DMSO-$d_6$, 400 MHz): δ=0.9-1.1 (m, 2H), 1.3-1.6 (m, 4H), 2.3-2.6 (m, 2H), 7.0-7.2 (m, 3H), 7.4-7.5 (m, 3H), 7.62 (dd, 1H, J=1, 8 Hz) 7.78 (s, 1H), 8.79 (s, 1H), 9.80 (s, 1H), 12.44 (s, 1H).

MS: 445.15 [M+H]$^+$

Example 44

Pharmacological Test 1
(Test Method)
(1) Construction of Human Cav3.2 Channel Expressing Stable Cell Line A sequence in which a HindIII site and a kozak sequence (GCCACC) was provided on a 5' side of a human Cav3.2 channel open reading frame (ORF) gene and a KpnI site was provided on a 3' side thereof was incorporated into pcDNA3.1(+) (Thermo Fisher Scientific #V790-20), and the resultant was transfected into a HEK293 cell (ATCC No. CRL-1573) according to a protocol of FuGENE (registered trademark) HD Transfection Reagent (Promega #E2311).

(2) Method of Measuring Intracellular Calcium Concentration

The human Cav3.2 channel expressing stable cell line prepared by the test method (1) was seeded in a 96-well plate using a Dulbecco's modified Eagle's medium (DMEM medium) containing 10% fetal bovine serum (FBS), followed by culturing 37° C. for 48 hours under a 5% $CO_2$ condition. Thereafter, the medium was removed, and each well washed with an A buffer was treated with 80 μL of a fluorescent dye solution containing a liquid mixture of 22 μg of a calcium fluorescent indicator Fluo-4 AM (Dojindo Molecular Technologies, Inc., #F311), 20 μL of dimethyl sulfoxide (DMSO), 1 μL of 10% Pluronic F-127 (Thermo Fisher Scientific #P6866), and 4 mL of the A buffer. After being left to stand for 45 minutes at room temperature under a light shielding condition, the cells were washed with a B buffer. In DMSO having the same final concentration as the test compound as a negative control, and the test compound dissolved in DMSO to have a final concentration of 0.1%, each test compound concentration solution containing the B buffer was added to each well. The cells were left to stand for additional 15 minutes at room temperature under a light shielding condition, and were measured using microplate reader EnVision (PerkinElmer Co., Ltd.) by the following method. First, after measuring background fluorescence in each well, an ionophore was added, and baseline fluorescence was measured. Thereafter, B buffer containing added KCl at a concentration of 83.8 mM was added to each well, and an increase in fluorescence due to calcium influx caused by the stimulation was measured for 10 seconds. Inhibition percentage was calculated from the maximum fluorescence increase value from the baseline, and an $IC_{50}$ value was calculated by plotting a logarithmic value of the test compound concentration and inhibition activity. The measurement was performed by observing fluorescence of 510 nm emitted when the cells were irradiated with excitation light of 485 nm.

(Buffer Composition)

A buffer: 140 mM NaCl, 5 mM KCl, 1 mM $MgCl_2$, 0.5 mM $CaCl_2$, 10 mM Glucose, 10 mM HEPES, pH 7.3

B buffer: potassium equilibrium potential: −92 mV (Test Results)

The test results are shown in Tables 1 to 3.

TABLE 1

| Test compound | Cav3.2 channel inhibitory action | Test compound | Cav3.2 channel inhibitory action |
|---|---|---|---|
| Example 1A | +++ | Example 1B | +++ |
| Example 2A | +++ | Example 2B | + |
| Example 3 | ++ | | |
| Example 4A | +++ | Example 4B | +++ |
| Example 5A | +++ | Example 5B | +++ |
| Example 6A | ++ | Example 6B | ++ |
| Example 7A | +++ | Example 7B | +++ |
| Example 8A | +++ | Example 8B | ++ |
| Example 9 | + | | |
| Example 10 | + | | |
| Example 11 | ++ | | |
| Example 12 | ++ | | |
| Example 13 | + | | |
| Example 14 | +++ | | |
| Example 15 | ++ | | |
| Example 16A | +++ | Example 16B | ++ |
| Example 17 | + | | |
| Example 18A | +++ | Example 18B | + |
| Example 19A | ++ | Example 19B | ++ |
| Example 20 | +++ | | |
| Example 21 | +++ | | |
| Example 22 | ++++ | | |

TABLE 2

| Test compound | Cav3.2 channel inhibitory action | Test compound | Cav3.2 channel inhibitory action |
|---|---|---|---|
| Example 23A | ++ | Example 23B | +++ |
| Example 24 | ++++ | | |
| Example 25 | ++ | | |
| Example 26 | ++++ | | |
| Example 27 | ++++ | | |
| Example 28 | +++ | | |
| Example 29 | ++ | | |
| Example 30 | + | | |
| Example 31 | ++++ | | |
| Example 32A | +++ | Example 32B | +++ |
| Example 33A | ++ | Example 33B | ++ |
| Example 34 | ++++ | | |
| Example 35 | +++ | | |

TABLE 3

| Test compound | Cav3.2 channel inhibitory action | Test compound | Cav3.2 channel inhibitory action |
|---|---|---|---|
| Example 36 | ++++ | | |
| Example 37 | +++ | | |
| Example 38A | ++++ | Example 38B | ++++ |
| Example 39 | ++++ | | |
| Example 40 | ++++ | | |
| Example 41 | +++ | | |
| Example 42 | +++ | | |
| Example 43 | ++++ | | |

$IC_{50} \leq 0.1$ μM; ++++, $0.1$ μM$<IC_{50} \leq 1$ μM; +++, $1$ μM$<IC_{50} \leq 10$ μM; ++, $10$ μM$<IC_{50}$; +

As is clear from Tables 1 to 3, the compound of the present invention was found to have an excellent voltage-dependent T-type calcium channel inhibitory action.

Example 45

Pharmacological Test 2

(Test Method)

Electrophysiological Evaluation

The human Cav3.2 channel expressing stable cell line prepared by the test method (1) of Example 36 was seeded in a 10-cm dish using a DMEM medium containing 10% FBS, followed by culturing 37° C. for 24 hours under a 5% $CO_2$ condition. The cells were detached using Accutase, and suspended in ice-cooled extracellular fluid for use. A Cav3.2 channel current was measured using an automated patch clamp system (Port-a-Patch; Nanion Technologies, EPC-10; HEKA Elektronik GmbH, Patchmaster; HEKA Elektronik GmbH) and buffers shown below, by a whole-cell patch-clamp method. The measurement of the Cav3.2 channel current was performed at room temperature, a measurement condition was a holding potential of −80 mV, a depolarization potential was −20 mV, a depolarization time was 100 msec, and a depolarization frequency was 10 sec. The Cav3.2 channel current was a peak value of an inward current observed at the time of depolarization to −20 mV.

The test compound was obtained by diluting a DMSO solution 1000 times with extracellular fluid to prepare a solution having a target concentration. The test compound was applied using an external perfusion system (Nanion Technologies) until the Cav3.2 channel current was stabilized, and a maximum of five concentrations from the low concentration side were cumulatively applied. An inhibition rate of the test compound was calculated from a change rate between a current value immediately before application of the test compound and the Cav3.2 channel current after application of the test compound (in a condition of holding potential of −80 mV, a concentration of the test compound was 0.3 μM, and in a condition of holding potential of −100 mV, a concentration of the test compound was 3 μM).

(Buffer Composition)

Extracellular fluid: 135 mM NaCl, 4 mM KCl, 1 mM $MgCl_2$, 5 mM $CaCl_2$, 5 mM D-Glucose, 10 mM HEPES, pH 7.4

Electrode internal fluid: 10 mM NaCl, 10 mM HEPES, 50 mM CsCl, 60 mM Cs-Fluoride, 20 mM EGTA, pH 7.2

(Test Results)

The test results are shown in Table 4.

TABLE 4

| Test compound | Cav3.2 channel current inhibition rate in test compound of 0.3 µM (holding potential of −80 mV) (%) | Cav3.2 channel current inhibition rate in test compound of 3 µM (holding potential of −100 mV) (%) |
|---|---|---|
| RQ-00311651 | 17 | 14 |
| Example 1A | 86 | NT |
| Example 4A | 43 | 38 |
| Example 4B | 23 | NT |
| Example 5A | 74 | 32 |
| Example 7A | 30 | NT |
| Example 18A | 46 | NT |
| Example 20 | 39 | 32 |
| Example 21 | 51 | 41 |
| Example 22 | 95 | NT |
| Example 24 | 68 | NT |
| Example 26 | 84 | NT |

Not tested; NT

RQ-00311651: See Patent Document 5

As is clear from Table 4, the compound of the present invention was found to have an excellent voltage-dependent T-type calcium channel inhibitory action.

Example 46

Pharmacological Test 3

(Test Method)

Mechanical Allodynia in Mouse Partial Sciatic Nerve Ligation (PSNL) Model

A mouse PSNL model was prepared according to a method of Seltzer et al. A mouse was anesthetized by inhalation with isoflurane. A femoral region of the mouse was shaved and disinfected with isodine. Skin on a femur of the mouse was incised, fascia just below the skin was cut off, and muscle heads of musculus biceps femoris were divided. After confirmation of sciatic nerves just below the muscle, and the sciatic nerves were separated without damage. ½ to ⅓ of the sciatic nerve was penetrated by a needle with 8-0 silk and ligated. The skin was sutured and the mouse was reared for about 7 days. In surgery of a sham control mouse, only confirmation of the sciatic nerves was performed and then the skin was sutured.

A pain threshold was measured after moving the mice to a cage for measurement and waiting for the exploratory behavior to disappear. Regarding the pain threshold (paw withdrawal filament ((g)), soles of the mice were stimulated with von Frey filaments (Sttoelting Co.: TOUCH-TEST SENSORY EVLUATOR) having different stimulation intensities, and the presence or absence of avoidance response was observed. A 50% threshold was calculated by an up down method with reference to a method of Chaplan et al. (Quantitative assessment of tactile allodynia in the rat paw. J neurosci Methods, 53, 1994, 55 to 63).

In drug efficacy evaluation, the compound described in Example 5A or Example 26 was orally administered to PSNL, and the effect on pain threshold was observed through a von Frey filament test.

(Test Results)

Figure 2:
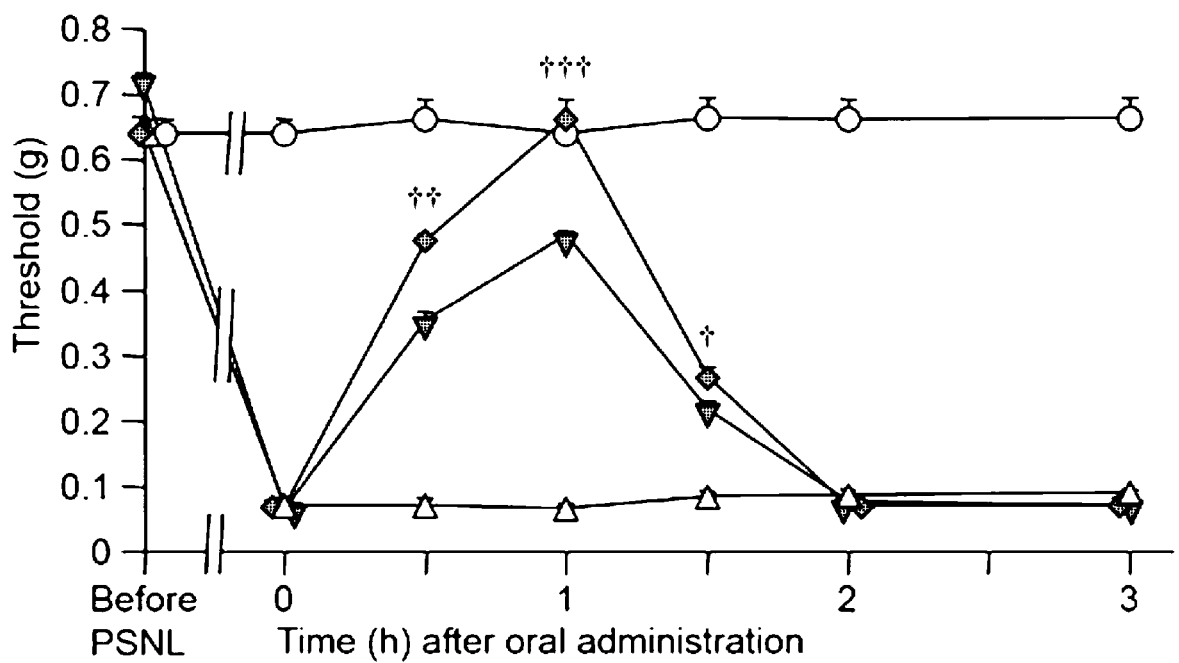
FIG. 2 shows test results of allodynia in a PSNL model using a compound described in Example 26.

The results are shown in FIGS. 1 and 2.

As is clear from FIG. 1, by orally administering 30 mg/kg of the compound described in Example 5A, mechanical allodynia was statistically significantly suppressed compared to the vehicle group.

As is clear from FIG. 2, by orally administering 30 mg/kg of the compound described in Example 26, mechanical allodynia was statistically significantly suppressed compared to the vehicle group.

INDUSTRIAL APPLICABILITY

The compounds of the present invention can be used as a therapeutic agent for pain.

DESCRIPTION OF THE REFERENCE SYMBOLS

In FIG. 1, ○ represents Sham+Vehicle.

In FIG. 1, ● represents PSNL+Vehicle.

In FIG. 1, ■ represents PSNL+20 mg/kg of the compound described in Example 5A.

In FIG. 1, ▲ represents PSNL+30 mg/kg of the compound described in Example 5A.

In FIG. 2, ○ represents Sham+Vehicle.

In FIG. 2, Δ represents PSNL+Vehicle.

In FIG. 2, ▼ represents PSNL+20 mg/kg of the compound described in Example 26.

In FIG. 2, ♦ represents PSNL+20 mg/kg of the compound described in Example 26.

The invention claimed is:

1. A compound represented by the following General Formula (I), a tautomer, a stereoisomer, or a pharmaceutically acceptable salt of the compound, or a solvate thereof,

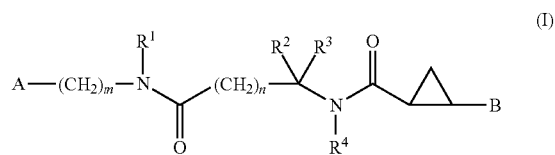

in the formula,

A represents a benzene ring which may have a substituent; a 4- to 6-membered heterocyclic ring having one to three same or different heteroatoms selected from an oxygen atom, a sulfur atom, and a nitrogen atom, and a carbon atom, as a ring-constituting atom; or a hetero-fused ring consisting of the heterocyclic ring, and a benzene ring or a 6-membered heteroaryl ring having one or two nitrogen atoms and a carbon atom, in which the heterocyclic ring and the hetero-fused ring may have a substituent, and are bonded to $(CH_2)_m$ via a carbon atom constituting these rings;

B represents a hetero-fused ring consisting of a 5- or 6-membered heteroaryl ring having one to three same or different heteroatoms selected from an oxygen atom, a sulfur atom, and a nitrogen atom, and a carbon atom, as a ring-constituting atom, and a benzene ring or a 6-membered heteroaryl ring having one or two nitrogen atoms and a carbon atom, in which the hetero-fused ring may have a substituent, and are bonded to a cyclopropyl group via a carbon atom constituting these rings;

$R^1$ represents a hydrogen atom or an alkyl group having 1 to 6 carbon atoms, or forms $(CH_2)_p$ together with $R^2$, in which p represents 1, 2, or 3;

$R^2$ and $R^3$ may be the same as or different from each other, and each represents a hydrogen atom, an alkyl group having 1 to 6 carbon atoms, or an alkyl group having 1 to 6 carbon atoms which is substituted with an alkoxy group having 1 to 6 carbon atoms, or $R^2$ and $R^3$ together form $CH_2$—X—$CH_2$, in which X represents a bond, $CH_2$, $CH_2CH_2$, $CH_2CH_2CH_2$, or $CH_2N(R^5)CH_2$, in which $R^5$ represents a hydrogen atom or an alkyl group having 1 to 6 carbon atoms;

$R^4$ represents a hydrogen atom or an alkyl group having 1 to 6 carbon atoms, or forms $(CH_2)_q$ together with $R^3$, in which q represents 2, 3, or 4;

m represents 0, 1, or 2; and n represents 0 or 1.

2. The compound, a tautomer, a stereoisomer, or a pharmaceutically acceptable salt of the compound, or a solvate thereof according to claim 1, wherein A is a benzene ring which may have a substituent, or a 4- to 6-membered heterocyclic ring which may have a substituent and has one or two nitrogen atoms and a carbon atom, as a ring-constituting atom.

3. The compound, a tautomer, a stereoisomer, or a pharmaceutically acceptable salt of the compound, or a solvate thereof according to claim 1, wherein A is a benzene ring which may have a substituent, or a heterocyclic ring which is selected from a pyridyl group, a pyrazinyl group, an azetidinyl group, a pyrrolidinyl group, and a piperidinyl group, which may have a substituent.

4. The compound, a tautomer, a stereoisomer, or a pharmaceutically acceptable salt of the compound, or a solvate thereof according to claim 1, wherein A is a phenyl group, or a heterocyclic ring which is selected from a pyridyl group, a pyrazinyl group, an azetidinyl group, a pyrrolidinyl group, and a piperidinyl group, which may be substituted with one to five same or different substituents selected from a halogen atom, a hydroxy group, a cyano group, a carboxy group, an amino group, a nitro group, an alkyl group having 1 to 6 carbon atoms, an alkoxy group having 1 to 6 carbon atoms, an alkyl group having 1 to 6 carbon atoms which is substituted with one to three halogen atoms, an alkoxy group having 1 to 6 carbon atoms which is substituted with one to three halogen atoms, an (alkoxy group having 1 to 6 carbon atoms) carbonyl group, an acyl group having 1 to 7 carbon atoms, an alkylsulfonyl group having 1 to 6 carbon atoms, a carbamoyl group which may be substituted with one or two alkyl groups having 1 to 6 carbon atoms, and a 4- to 6-membered cyclic aminocarbonyl group.

5. The compound, a tautomer, a stereoisomer, or a pharmaceutically acceptable salt of the compound, or a solvate thereof according to claim 1, wherein B is a hetero-fused ring which may be substituted with a substituent and consists of a 5-membered heteroaryl ring having one or two nitrogen atoms and a carbon atom, as a ring-constituting atom, and a benzene ring.

6. The compound, a tautomer, a stereoisomer, or a pharmaceutically acceptable salt of the compound, or a solvate thereof according to claim 1, wherein B is a benzimidazol-2-yl group, an indol-3-yl group, a benzoxazol-2-yl group, or an indazol-6-yl group, which may be substituted with one to five same or different substituents selected from a halogen atom, a hydroxy group, a cyano group, a carboxy group, an amino group, a nitro group, an alkyl group having 1 to 6 carbon atoms, an alkoxy group having 1 to 6 carbon atoms, an alkyl group having 1 to 6 carbon atoms which is substituted with one to three halogen atoms, an alkoxy group having 1 to 6 carbon atoms which is substituted with one to three halogen atoms, an (alkoxy group having 1 to 6 carbon atoms) carbonyl group, an acyl group having 1 to 7 carbon atoms, an alkylsulfonyl group having 1 to 6 carbon atoms, a carbamoyl group which may be substituted with one or two alkyl groups having 1 to 6 carbon atoms, and a 4- to 6-membered cyclic aminocarbonyl group.

7. The compound, a tautomer, a stereoisomer, or a pharmaceutically acceptable salt of the compound, or a solvate thereof according to claim 1, wherein B is a benzimidazol-2-yl group.

8. The compound, a tautomer, a stereoisomer, or a pharmaceutically acceptable salt of the compound, or a solvate thereof according to claim 1, wherein $R^1$ is a hydrogen atom.

9. The compound, a tautomer, a stereoisomer, or a pharmaceutically acceptable salt of the compound, or a solvate thereof according to claim 1, wherein $R^2$ and $R^3$ may be the same as or different from each other, and each represents a hydrogen atom or an alkyl group having 1 to 6 carbon atoms.

10. The compound, a tautomer, a stereoisomer, or a pharmaceutically acceptable salt of the compound, or a solvate thereof according to claim 1, wherein $R^2$ and $R^3$ together form $CH_2CH_2$ or $CH_2CH_2CH_2$.

11. The compound, a tautomer, a stereoisomer, or a pharmaceutically acceptable salt of the compound, or a solvate thereof according to claim 1, wherein $R^4$ is a hydrogen atom.

12. The compound, a tautomer, a stereoisomer, or a pharmaceutically acceptable salt of the compound, or a solvate thereof according to claim 1, wherein m is 0.

13. The compound, a tautomer, a stereoisomer, or a pharmaceutically acceptable salt of the compound, or a solvate thereof according to claim 1, wherein n is 0.

14. A compound, a tautomer, a stereoisomer, or a pharmaceutically acceptable salt of the compound, or a solvate thereof, wherein the compound is selected from the group consisting of:

(1 S, 2S)-2-(1H-benzo[d]imidazol-2-yl)-N—((R)-1-oxo-1-((4-propylphenyl)amino)propan-2-yl) cyclopropane-1-carboxamide, (1 S, 2S)-2-(1H-benzo[d]imidazol-2-yl)-N—((S)-1-oxo-1-((4-propylphenyl)amino)propan-2-yl) cyclopropane-1-carboxamide, (1R, 2R)-2-(1H-benzo[d]imidazol-2-yl)-N—((R)-1-oxo-1-((4-propylphenyl)amino)propan-2-yl) cyclopropane-1-carboxamide, (1R, 2R)-2-(1H-benzo[d]imidazol-2-yl)-N—((S)-1-oxo-1-((4-propylphenyl)amino)propan-2-yl) cyclopropane-1-carboxamide, (1 S, 2S)-2-(1H-benzo[d]imidazol-2-yl)-N—((R)-1-((4-isopropoxyphenyl)amino)-1-oxopropan-2-yl) cyclopropane-1-carboxamide, (1S, 2S)-2-(1H-benzo[d]imidazol-2-yl)-N—((S)-1-(4-isopropoxyphenyl)amino)-1-oxopropan-2-yl) cyclopropane-1-carboxamide, (1S, 2S)-2-(1H-benzo[d]imidazol-2-yl)-N—((R)-1-oxo-1-((4-(trifluoromethyl)phenyl)amino)propan-2-yl) cyclopropane-1-carboxamide, (1S, 2S)-2-(1H-benzo[d]imidazol-2-yl)-N—((S)-1-oxo-1-((4-(trifluoromethyl)phenyl)amino)propan-2-yl) cyclopropane-1-carboxamide, (1S, 2S)-2-(1H-benzo[d]imidazol-2-yl)-N—((R)-1-oxo-1-((6-(trifluoromethyl)pyridin-3-yl)amino)propan-2-yl) cyclopropane-1-carboxamide, (1S, 2S)-2-(1H-benzo[d]imidazol-2-yl)-N—((S)-1-oxo-1-((6-(trifluoromethyl)pyridin-3-yl)amino)propan-2-yl) cyclopropane-1-carboxamide, (1S, 2S)-2-(1H-benzo[d]imidazol-2-yl)-N—((R)-1-((4-cyanophenyl)amino)-1-oxopropan-2-yl) cyclopropane-1-carboxamide, (1S, 2S)-2-(1H-benzo[d]imidazol-2-yl)-N—((S)-1-(4-cyanophenyl)amino)-1-oxopropan-2-yl) cyclopropane-1-carboxamide, (1S, 2S)-2-(1H-benzo[d]imidazol-2-yl)-N—((R)-1-((4-(tert-butyl)phenyl)amino)-1-oxopropan-2-yl) cyclopropane-1-carboxamide, (1S, 2S)-2-(1H-benzo[d]imidazol-2-yl)-N—((S)-1-((4-(tert-butyl)phenyl)amino)-1-oxopropan-2-yl) cyclopropane-1-carboxamide, (1S, 2S)-2-(1H-benzo[d]imidazol-2-yl)-N—((R)-1-(methyl(4-(trifluoromethyl)phenyl)amino)-1-oxopropan-2-yl) cyclopropane-1-carboxamide, (1S, 2S)-2-(1H-benzo[d]imidazol-2-yl)-N—((S)-1-(methyl(4-(trifluoromethyl)phenyl)amino)-1-oxopropan-2-yl) cyclopropane-1-carboxamide, (1S, 2S)-2-(1H-benzo[d]imidazol-2-yl)-N—((R)-1-((4-(methylsulfonyl)benzyl)amino)-1-oxopropan-2-yl) cyclopropane-1-carboxamide, (1S, 2S)-2-(1H-benzo[d]imidazol-2-yl)-N—((S)-1-((4-(methylsulfonyl)benzyl)amino)-1-oxopropan-2-yl) cyclopropane-1-carboxamide, tert-butyl 3-((R)-2-((1S, 2S)-2-(1H-benzo[d]imidazol-2-yl) cyclopropane-1-carboxamido)propanamido) azetidine-1-carboxylate, tert-butyl 3-((S)-2-((1S, 2S)-2-(1H-benzo[d]imidazol-2-yl) cyclopropane-1-carboxamido)propanamido) azetidine-1-carboxylate, tert-butyl 4-((R)-2-((1S, 2S)-2-(1H-benzo[d]imidazol-2-yl) cyclopropane-1-carboxamido)propanamido) piperidine-1-carboxylate, tert-butyl 4-((S)-2-((1S, 2S)-2-(1H-benzo[d]imidazol-2-yl) cyclopropane-1-carboxamido)propanamido) piperidine-1-carboxylate, (1S, 2S)-2-(1H-benzo[d]imidazol-2-yl)-N—((R)-1-oxo-1-(piperidin-4-ylamino)propan-2-yl) cyclopropane-1-carboxamide, (1S, 2S)-2-(1H-benzo[d]imidazol-2-yl)-N—((S)-1-oxo-1-(piperidin-4-ylamino)propan-2-yl) cyclopropane-1-carboxamide, (1S, 2S)-2-(1H-benzo[d]imidazol-2-yl)-N—((R)-1-oxo-1-((1-propionylpiperidin-4-yl)amino)propan-2-yl) cyclopropane-1-carboxamide, (1S, 2S)-2-(1H-benzo[d]imidazol-2-yl)-N—((S)-1-oxo-1-((1-propionylpiperidin-4-yl)amino)propan-2-yl) cyclopropane-1-carboxamide, (1S, 2S)-2-(1H-benzo[d]imidazol-2-yl)-N—((R)-1-oxo-1-((4-(trifluoromethyl)benzyl)amino)propan-2-yl) cyclopropane-1-carboxamide, (1S, 2S)-2-(1H-benzo[d]imidazol-2-yl)-N—((S)-1-oxo-1-((4-(trifluoromethyl)benzyl)amino)propan-2-yl) cyclopropane-1-carboxamide, (1S, 2S)-2-(1H-benzo[d]imidazol-2-yl)-N—((R)-1-oxo-1#(6-(trifluoromethyl)pyridin-3-yl)methyl)amino)propan-2-yl) cyclopropane-1-carboxamide, (1S, 2S)-2-(1H-benzo[d]imidazol-2-yl)-N—((S)-1-oxo-1-(((6-(trifluoromethyl)pyridin-3-yl)methyl)amino) propan-2-yl) cyclopropane-1-carboxamide, (1S, 2S)-2-(1H-benzo[d]imidazol-2-yl)-N—((R)-1-((4-chlorophenyl)amino)-1-oxopropan-2-yl) cyclopropane-1-carboxamide, (1S, 2S)-2-(1H-benzo[d]imidazol-2-yl)-N—((S)-1-(4-chlorophenyl)amino)-1-oxopropan-2-yl) cyclopropane-1-carboxamide, (1S, 2S)-2-(1H-benzo[d]imidazol-2-yl)-N—((R)-1-oxo-1-(pyrazin-2-ylamino)propan-2-yl) cyclopropane-1-carboxamide, (1S, 2S)-2-(1H-benzo[d]imidazol-2-yl)-N—((S)-1-oxo-1-(pyrazin-2-ylamino)propan-2-yl) cyclopropane-1-carboxamide, (1R, 2R)-2-(1H-benzo[d]imidazol-2-yl)-N—((R)-1-oxo-1-(pyrazin-2-ylamino)propan-2-yl) cyclopropane-1-carboxamide, (1R, 2R)-2-(1H-benzo[d]imidazol-2-yl)-N—((S)-1-oxo-1-(pyrazin-2-ylamino)propan-2-yl) cyclopropane-1-carboxamide, (1S, 2S)-2-(1H-benzo[d]imidazol-2-yl)-N—((R)-1#5-bromopyrazin-2-yl)amino)-1-oxopropan-2-yl) cyclopropane-1-carboxamide, (1S, 2S)-2-(1H-benzo[d]imidazol-2-yl)-N—((S)-1-((5-bromopyrazin-2-yl)amino)-1-oxopropan-2-yl) cyclopropane-1-carboxamide, (1R, 2R)-2-(1H-benzo[d]imidazol-2-yl)-N—((R)-1-((5-bromopyrazin-2-yl)amino)-1-oxopropan-2-yl) cyclopropane-1-carboxamide, (1R, 2R)-2-(1H-benzo[d]imidazol-2-yl)-N—((S)-1-((5-bromopyrazin-2-yl)amino)-1-oxopropan-2-yl) cyclopropane-1-carboxamide, (R)-1-((1S, 2S)-2-(1H-benzo[d]imidazol-2-yl) cyclopropane-1-carbonyl)-N-(4-(trifluoromethyl)phenyl) pyrrolidine-2-carboxamide, (S)-1-((1S, 2S)-2-(1H-benzo[d]imidazol-2-yl) cyclopropane-1-carbonyl)-N-(4-(trifluoromethyl)phenyl) pyrrolidine-2-carboxamide, (R)-1-((1R, 2R)-2-(1H-benzo[d]imidazol-2-yl) cyclopropane-1-carbonyl)-N-(4-(trifluoromethyl)phenyl) pyrrolidine-2-carboxamide, (S)-1-((1R, 2R)-2-(1H-benzo[d]imidazol-2-yl) cyclopropane-1-carbonyl)-N-(4-(trifluoromethyl)phenyl) pyrrolidine-2-carboxamide, (1S, 2S)-2-(1H-benzo[d]imidazol-2-yl)-N-(2-oxo-2-((4-(trifluoromethyl)phenyl)amino)ethyl) cyclopropane-1-carboxamide, (1R, 2R)-2-(1H-benzo[d]imidazol-2-yl)-N-(2-oxo-2-((4-(trifluoromethyl)phenyl)amino)ethyl) cyclopropane-1-carboxamide, 1-((1S, 2S)-2-(1H-benzo[d]imidazol-2-yl) cyclopropane-1-carboxamido)-N-(4-(trifluoromethyl)phenyl) cyclopropane-1-carboxamide, 1-((1R, 2R)-2-(1H-benzo[d]imidazol-2-yl) cyclopropane-1-carboxamido)-N-(4-(trifluoromethyl)phenyl) cyclopropane-1-carboxamide, 1-((1S, 2S)-2-(1H-benzo[d]imidazol-2-yl) cyclopropane-1-carboxamido)-N-(3-(trifluoromethyl)phenyl) cyclopropane-1-carboxamide, (1S, 2S)-2-(1H-benzo[d]imidazol-2-yl)-N—((R)-2-oxo-1-(4-(trifluoromethyl)phenyl)pyrrolidin-3-yl) cyclopropane-1-carboxamide, (1S, 2S)-2-(1H-benzo[d]imidazol-2-yl)-N—((S)-2-oxo-1-(4-(trifluoromethyl)phenyl)pyrrolidin-3-yl) cyclopropane-1-carboxamide, 1-((1S, 2S)-2-(1H-benzo[d]imidazol-2-yl) cyclopropane-1-carboxamido)-N-(4-(trifluoromethoxy)phenyl) cyclopropane-1-carboxamide, 1-((1S, 2S)-2-(1H-benzo[d]imidazol-2-yl) cyclopropane-1-carboxamido)-N-(2-(trifluoromethyl)phenyl) cyclopropane-1-carboxamide,
1-((1S, 2S)-2-(1-ethyl-1H-benzo[d]imidazol-2-yl) cyclopropane-1-carboxamido)-N-(6-(trifluoromethyl)pyridin-3-yl) cyclopropane-1-carboxamide,
1-((1S, 2S)-2-(1H-benzo[d]imidazol-2-yl) cyclopropane-1-carboxamido)-N-(2-fluoro-4-(trifluoromethyl)phenyl) cyclopropane-1-carboxamide,
1-((1S, 2S)-2-(1H-benzo[d]imidazol-2-yl) cyclopropane-1-carboxamido)-N-(5-(trifluoromethyl)pyridin-3-yl) cyclopropane-1-carboxamide,
(1S, 2S)-2-(1H-benzo[d]imidazol-2-yl)-N-(2-(isopropyl (6-(trifluoromethyl)pyridin-3-yl)amino)-2-oxoethyl) cyclopropane-1-carboxamide,
1-((1S, 2S)-2-(1H-benzo[d]imidazol-2-yl) cyclopropane-1-carboxamido)-N-(4-fluoro-3-(trifluoromethyl)phenyl) cyclopropane-1-carboxamide,
(1S, 2S)-2-(1H-benzo[d]imidazol-2-yl)-N—((R)-1-((4-fluoro-3-(trifluoromethyl)phenyl)amino)-3-methoxy-1-oxopropan-2-yl) cyclopropane-1-carboxamide,
(1S, 2S)-2-(1H-benzo[d]imidazol-2-yl)-N—((S)-1-((4-fluoro-3-(trifluoromethyl)phenyl)amino)-3-methoxy-1-oxopropan-2-yl) cyclopropane-1-carboxamide,
(1S, 2S)-2-(1H-benzo[d]imidazol-2-yl)-N—((R)-5-oxo-1-(6-(trifluoromethyl)pyridin-3-yl)pyrrolidin-3-yl) cyclopropane-1-carboxamide,
(1S, 2S)-2-(1H-benzo[d]imidazol-2-yl)-N—((S)-5-oxo-1-(6-(trifluoromethyl)pyridin-3-yl)pyrrolidin-3-yl) cyclopropane-1-carboxamide,
1-((1S, 2S)-2-(5-chloro-1H-benzo[d]imidazol-2-yl) cyclopropane-1-carboxamido)-N-(4-fluoro-3-(trifluoromethyl)phenyl) cyclopropane-1-carboxamide,
1-((1S, 2S)-2-(1H-benzo[d]imidazol-2-yl) cyclopropane-1-carboxamido)-N-(3,5-dichlorophenyl) cyclopropane-1-carboxamide,
1-((1S, 2S)-2-(1H-benzo[d]imidazol-2-yl) cyclopropane-1-carboxamido)-N-(3-(trifluoromethyl)phenyl) cyclobutane-1-carboxamide,
(1S, 2S)-2-(1H-benzo[d]imidazol-2-yl)-N—((R)-4-methyl-1-oxo-1-((3-(trifluoromethyl)phenyl)amino) pentan-2-yl) cyclopropane-1-carboxamide,
(1S, 2S)-2-(1H-benzo[d]imidazol-2-yl)-N—((R)-1-oxo-1-((3-(trifluoromethyl)phenyl)amino)propan-2-yl) cyclopropane-1-carboxamide,
(1S, 2S)-2-(1H-benzo[d]imidazol-2-yl)-N—((S)-1-oxo-1-((3-(trifluoromethyl)phenyl)amino)propan-2-yl) cyclopropane-1-carboxamide,
1-((1S, 2S)-2-(1H-benzo[d]imidazol-2-yl) cyclopropane-1-carboxamido)-N-(3-(trifluoromethyl)phenyl) cyclobutane-1-carboxamide,
(1S, 2S)-2-(1H-benzo[d]imidazol-2-yl)-N—((R)-4-methyl-1-oxo-1-((3-(trifluoromethyl)phenyl)amino) pentan-2-yl) cyclopropane-1-carboxamide,
(1S, 2S)-2-(1H-benzo[d]imidazol-2-yl)-N—((R)-1-oxo-1-((3-(trifluoromethyl)phenyl)amino)propan-2-yl) cyclopropane-1-carboxamide,
(1S, 2S)-2-(1H-benzo[d]imidazol-2-yl)-N—((S)-1-oxo-1-((3-(trifluoromethyl)phenyl)amino)propan-2-yl) cyclopropane-1-carboxamide,
(1S, 2S)-2-(1H-benzo[d]imidazol-2-yl)-N-(2-oxo-2-((3-(trifluoromethyl)phenyl)amino)ethyl) cyclopropane-1-carboxamide,
1-((1S, 2S)-2-(1-cyclopropyl-1H-benzo[d]imidazol-2-yl) cyclopropane-1-carboxamido)-N-(3-(trifluoromethyl) phenyl) cyclopropane-1-carboxamide,
1-((1S, 2S)-2-(1H-benzo[d]imidazol-2-yl) cyclopropane-1-carboxamido)-N-(2-fluoro-3-(trifluoromethyl)phenyl) cyclopropane-1-carboxamide,
1-((1S, 2S)-2-(1H-benzo[d]imidazol-2-yl) cyclopropane-1-carboxamido)-N-(3-fluoro-5-(trifluoromethyl)phenyl) cyclopropane-1-carboxamide, and
1-((1S, 2S)-2-(1H-benzo[d]imidazol-2-yl) cyclopropane-1-carboxamido)-N-(3-(trifluoromethoxy)phenyl) cyclopropane-1-carboxamide.

15. A pharmaceutical composition comprising:
the compound, a tautomer, a stereoisomer, or a pharmaceutically acceptable salt of the compound, or a solvate thereof according to claim 1, as an active ingredient, and an excipient.

16. A method of treating a disease associated with a T-type calcium channel, comprising:
administering an effective amount of the compound, a tautomer, a stereoisomer, or a pharmaceutically acceptable salt of the compound, or a solvate thereof according to claim 1 to a human in need thereof.

17. A method of treating acute pain, chronic pain, or neuropathic pain in a human, comprising:
administering an effective amount of the compound, a tautomer, a stereoisomer, or a pharmaceutically acceptable salt of the compound, or a solvate thereof according to claim 1 to a human in need thereof.

18. A pharmaceutical composition comprising:
the compound, a tautomer, a stereoisomer, or a pharmaceutically acceptable salt of the compound, or a solvate thereof according to claim 14, as an active ingredient, and an excipient.

19. A method of treating a disease associated with a T-type calcium channel, comprising:
administering an effective amount of the compound, a tautomer, a stereoisomer, or a pharmaceutically acceptable salt of the compound, or a solvate thereof according to claim 14 to a human in need thereof.

20. A method of treating acute pain, chronic pain, or neuropathic pain in a human, comprising:
administering an effective amount of the compound, a tautomer, a stereoisomer, or a pharmaceutically acceptable salt of the compound, or a solvate thereof according to claim 14 to a human in need thereof.

21. A compound, a tautomer, a stereoisomer, or a pharmaceutically acceptable salt of the compound, or a solvate thereof,
wherein the compound is selected from the group consisting of:
1-((1 S, 2S)-2-(1H-benzo[d]imidazol-2-yl) cyclopropane-1-carboxamido)-N-(4-(trifluoromethyl)phenyl) cyclopropane-1-carboxamide,
1-((1R, 2R)-2-(1H-benzo[d]imidazol-2-yl) cyclopropane-1-carboxamido)-N-(4-(trifluoromethyl)phenyl) cyclopropane-1-carboxamide,
1-((1 S, 2S)-2-(1H-benzo[d]imidazol-2-yl) cyclopropane-1-carboxamido)-N-(3-(trifluoromethyl)phenyl) cyclopropane-1-carboxamide,
1-((1 S, 2S)-2-(1H-benzo[d]imidazol-2-yl) cyclopropane-1-carboxamido)-N-(4-(trifluoromethoxy)phenyl) cyclopropane-1-carboxamide,
1-((1 S, 2S)-2-(1H-benzo[d]imidazol-2-yl) cyclopropane-1-carboxamido)-N-(2-(trifluoromethyl)phenyl) cyclopropane-1-carboxamide,
1-((1 S, 2S)-2-(1-ethyl-1H-benzo[d]imidazol-2-yl) cyclopropane-1-carboxamido)-N-(6-(trifluoromethyl)pyridin-3-yl) cyclopropane-1-carboxamide, 1-((1S, 2S)-2-(1H-benzo[d]imidazol-2-yl) cyclopropane-1-carboxamido)-N-(2-fluoro-4-(trifluoromethyl)phenyl) cyclopropane-1-carboxamide, 1-((1S, 2S)-2-(1H-benzo[d]imidazol-2-yl) cyclopropane-1-carboxamido)-N-(5-(trifluoromethyl)pyridin-3-yl) cyclopropane-1-carboxamide, 1-((1S, 2S)-2-(1H-benzo[d]imidazol-2-yl) cyclopropane-1-carboxamido)-N-(4-fluoro-3-(trifluoromethyl)phenyl) cyclopropane-1-carboxamide, 1-((1S, 2S)-2-(5-chloro-1H-benzo[d]imidazol-2-yl) cyclopropane-1-carboxamido)-N-(4-fluoro-3-(trifluoromethyl)phenyl) cyclopropane-1-carboxamide, 1-((1S, 2S)-2-(1H-benzo[d]imidazol-2-yl) cyclopropane-1-carboxamido)-N-(3,5-dichlorophenyl) cyclopropane-1-carboxamide, 1-((1S, 2S)-2-(1H-benzo[d]imidazol-2-yl) cyclopropane-1-carboxamido)-N-(3-(trifluoromethyl)phenyl) cyclobutane-1-carboxamide, 1-((1S, 2S)-2-(1-cyclopropyl-1H-benzo[d]imidazol-2-yl) cyclopropane-1-carboxamido)-N-(3-(trifluoromethyl)phenyl) cyclopropane-1-carboxamide, 1-((1S, 2S)-2-(1H-benzo[d]imidazol-2-yl) cyclopropane-1-carboxamido)-N-(2-fluoro-3-(trifluoromethyl)phenyl) cyclopropane-1-carboxamide, 1-((1S, 2S)-2-(1H-benzo[d]imidazol-2-yl) cyclopropane-1-carboxamido)-N-(3-fluoro-5-(trifluoromethyl)phenyl) cyclopropane-1-carboxamide, and 1-((1S, 2S)-2-(1H-benzo[d]imidazol-2-yl) cyclopropane-1-carboxamido)-N-(3-(trifluoromethoxy)phenyl) cyclopropane-1-carboxamide.

22. A compound, a tautomer, a stereoisomer, or a pharmaceutically acceptable salt of the compound, or a solvate thereof, wherein the compound is selected from the group consisting of:

1-((1R, 2R)-2-(1H-benzo[d]imidazol-2-yl) cyclopropane-1-carboxamido)-N-(4-(trifluoromethyl)phenyl) cyclopropane-1-carboxamide, 1-((1S, 2S)-2-(1-cyclopropyl-1H-benzo[d]imidazol-2-yl) cyclopropane-1-carboxamido)-N-(3-(trifluoromethyl) phenyl) cyclopropane-1-carboxamide, and 1-((1S, 2S)-2-(1-ethyl-1H-benzo[d]imidazol-2-yl) cyclopropane-1-carboxamido)-N-(6-(trifluoromethyl)pyridin-3-yl) cyclopropane-1-carboxamide.

* * * * *